(12) United States Patent
Ozaki et al.

(10) Patent No.: US 6,258,825 B1
(45) Date of Patent: Jul. 10, 2001

(54) 2-OXOIMIDAZOLE DERIVATIVES

(75) Inventors: Satoshi Ozaki; Hiroshi Kawamoto; Yoshiki Ito, all of Tsukuba; Kaori Hirano, Ami-machi; Kyoko Hayashi; Yoshikazu Iwasawa, both of Tsukuba, all of (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/424,114

(22) PCT Filed: May 27, 1998

(86) PCT No.: PCT/JP98/02335

§ 371 Date: Nov. 19, 1999

§ 102(e) Date: Nov. 19, 1999

(87) PCT Pub. No.: WO98/54168

PCT Pub. Date: Dec. 3, 1998

(30) Foreign Application Priority Data

May 30, 1997 (JP) .................................................... 9-157913
Jul. 2, 1997 (JP) .................................................... 9-191859

(51) Int. Cl.⁷ ........................ A61K 31/454; C07D 401/04
(52) U.S. Cl. .......................... 514/322; 546/199; 546/194; 514/318
(58) Field of Search ................................. 514/322, 318; 546/199, 194

(56) References Cited

U.S. PATENT DOCUMENTS

| | | | |
|---|---|---|---|
| 3,989,707 | 11/1976 | Janssen et al. | 260/293.6 |
| 4,080,328 | 3/1978 | Maruyama et al. | 260/293.6 |

FOREIGN PATENT DOCUMENTS

| | | |
|---|---|---|
| 48-18284 | 3/1973 | (JP) . |
| 51-13780 | 2/1976 | (JP) . |
| 51-128974 | 11/1976 | (JP) . |
| 53-2475 | 1/1978 | (JP) . |
| 7-503240 | 4/1995 | (JP) . |
| WO93/14758 | 8/1993 | (WO) . |
| WO96/13262 | 5/1996 | (WO) . |
| WO97/40035 | 10/1997 | (WO) . |

OTHER PUBLICATIONS

Sato, M. et al. : Psychotropic agents. Synthesis and psychotropic activity of conformationally restricted butyrophenone analogs. Chem. Pharm. Bull. vol. 27, pp. 119–128, 1979.*

* cited by examiner

Primary Examiner—C. S. Aulakh
(74) Attorney, Agent, or Firm—Wenderoth, Lind & Ponack, L.L.P.

(57) ABSTRACT

The present invention relates to a compound represented by Formula [I]

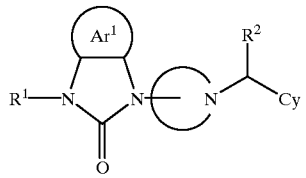

[I]

wherein

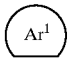

represents an aromatic carbo- or heterocyclic ring which may have a substituent; Cy represents a mono-, bi- or tricyclic aliphatic carbocyclic group having 3 to 20 carbon atoms, which may have a substituent;

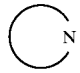

represents a mono- or bicyclic aliphatic nitrogen-containing heterocyclic group having 3 to 14 carbon atoms, which may have a substituent; $R^1$ represents a hydrogen atom, a lower alkenyl group, a lower alkynyl group, a cyclo(lower alkyl) group, an amino group, a lower alkylamino group, a di(lower alkyl)-amino group, a hydroxyl group, a lower alkoxy group, a carboxyl group, a lower alkoxycarbonyl group, a carbamoyl group, a lower alkylcarbamoyl group or a di(lower alkyl)carbamoyl group, or a lower alkyl group which may have a substituent; and $R^2$ represents a hydrogen atom or a lower alkyl group, a salt or ester thereof, a production process for the same, and an analgesic, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension, comprising an effective ingredient of the same.

17 Claims, No Drawings

2-OXOIMIDAZOLE DERIVATIVES

This application is a 371 of PCT/JP98/02335 filed May 27, 1998, now WO 98/54168 Mar. 12, 1998.

FIELD OF THE INVENTION

The present invention is useful in the medicinal field. More specifically, the 2-oxoimidazole derivative of the present invention has an action to inhibit nociceptin from binding to a nociceptin receptor ORL1 and is useful as an analgesic, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension.

BACKGROUND ART

Nociceptin (the same substance as orphanin FQ) is peptide comprising 17 amino acids and having a similar structure to that of opioid peptide. Nociceptin has an augmenting activity on reaction against nociceptive stimulation, an appetite stimulating activity, an activity for reducing a space learning ability, an antagonism against an analgesic action of a classic opiate agonist, a dopamine release inhibitory action, a water diuresis action, a vasodilative action, and a systemic blood pressure-lowering action, and it is considered to take part in controlling pain, appetite and memory learning through a nociceptin receptor ORL1 [refer to Nature, vol. 377, pp. 532 (1995); Society for Neuroscience, vol. 22, pp. 455 (1996);

NeuroReport, vol. 8, pp. 423 (1997); Eur. J. Neuroscience, vol. 9, pp. 194 (1997); Neuroscience, vol. 75, pp. 1 and 333 (1996); and Life Science, vol. 60, pp. PL15 and PL141 (1997)]. Further, it is known that morphine tolerance is reduced in a knockout mouse in which a nociceptin receptor ORL1 is deficient [Neuroscience Letters, vol. 237, pp. 136 (1997)].

Accordingly, it can be expected that a substance which specifically prevents nociceptin from binding to a nociceptin receptor ORL1 is useful as an analgesic against diseases accompanied with pains such as cancerous pain, postoperative pain, migraine, gout, chronic rheumatism, chronic pain and neuralgia, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension.

A compound which is structurally similar to the compound of the present invention is disclosed in International Publication WO96/13262 and the like. However, the compound of the present invention is neither specifically disclosed nor indicated, and an action to prevent nociceptin from binding to a nociceptin receptor ORL1 is not entirely described as well.

DISCLOSURE OF THE INVENTION

An object of the present invention is to provide an analgesic, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension, which are novel and have an action to prevent nociceptin from binding to a nociceptin acceptor ORL1.

The present inventors have found that a compound represented by Formula [I] has a high affinity to a nociceptin receptor and prevents the action of nociceptin, whereby it is useful as an analgesic against diseases accompanied with pains such as cancerous pain, postoperative pain, migraine, gout, chronic rheumatism, chronic pain and neuralgia, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension, and thus, they have completed the present invention:

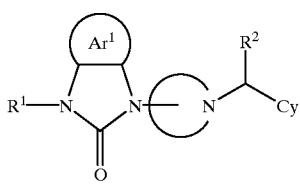

[wherein

represents an aromatic carbo- or heterocyclic ring which may have a substituent selected from the group consisting of a halogen atom, a lower alkyl group, an amino group, a lower alkylamino group, a di(lower alkyl)amino group, a hydroxyl group, a lower alkoxy group and a carboxyl group; $Ar^2$ represents an aromatic carbo- or heterocyclic group which may have a substituent selected from the group consisting of a halogen atom, a lower alkyl group, an amino group, a lower alkylamino group, a di(lower alkyl)amino group, a hydroxyl group, a lower alkoxy group and a carboxyl group; Cy represents a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, an amino group, a lower alkylamino group, a di(lower alkyl)amino group, a lower alkoxy group and a group represented by $-R^4$;

represents a mono- or bicyclic aliphatic nitrogen-containing heterocyclic group having 3 to 14 carbon atoms, which may have a substituent selected from the group consisting of a halogen atom, a lower alkylidene group, a lower alkenyl group, a lower alkynyl group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group, a di(lower alkyl)carbamoyl group and a group represented by —$R^3$; $R^1$ represents a hydrogen atom, a lower alkenyl group, a lower alkynyl group, a cyclo(lower alkyl) group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group or a di(lower alkyl)carbamoyl group, or a lower alkyl group which may have a substituent selected from the group consisting of a halogen atom, a cyclo(ower alkyl) group, an amino group, a lower alkylamino group, a di(lower alkyl) amino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group and a group represented by $Ar^2$; $R^2$ represents a hydrogen atom or a lower alkyl group; $R^3$ represents a lower alkyl group which may have a substituent selected from the group consisting of an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(oower alkyl)carbamoyl group, an aromatic heterocyclic group and a group represented by —$R^5$; $R^4$ represents a lower alkyl group which may have a substituent selected from the group consisting of a cycloalkyl group having 3 to 10 carbon atoms and an aromatic carbo- or heterocyclic group; and $R^5$ represents a lower alkylamino group, a di(lower alkyl)amino group or a lower alkoxy group, which may have an aromatic carbo- or heterocyclic group].

The present invention relates to the compound represented by Formula [I], salts or esters thereof, and a production process and uses thereof.

The symbols and the terms described in the present specification shall be explained.

The term [halogen atom] means a fluorine atom, a chlorine atom, a bromine atom and an iodine atom.

The term [lower alkyl group] means a linear or branched alkyl group having 1 to 6 carbon atoms and includes, for example, methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, and 1-ethyl-1-methylpropyl.

The term [lower alkylamino group] means an amino group mono-substituted with the lower alkyl groups described above and includes, for example, methylamino, ethylamino, propylamino, isopropylamino, butylamino, sec-butylamino and tert-butylamino.

The term [di(lower alkyl)amino group] means an amino group di-substituted with the lower alkyl groups described above and includes, for example, dimethylamino, diethylamino, ethylmethylamino, dipropylamino, methylpropylamino and diisopropylamino.

The term [lower alkoxy group] means an alkoxy group having the lower alkyl groups described above, that is, an alkoxy group having 1 to 6 carbon atoms and includes, for example, methoxy, ethoxy, propoxy, isopropoxy, butoxy, isobutoxy, tert-butoxy and pentyloxy.

The term [aromatic carbocyclic ring] means a benzene ring, a naphthalene ring or an anthracene ring.

The term [aromatic heterocyclic ring] means a 5-membered or 6-membered monocyclic aromatic heterocyclic ring containing at least one, preferably 1 to 3 hetero atoms which may be the same or different, and are selected from the group consisting of an oxygen atom, a nitrogen atom and a sulfur atom, or a condensed type aromatic heterocyclic ring formed by condensing the above monocyclic aromatic heterocyclic ring with the above aromatic carbocyclic ring or by condensing the above same or different monocyclic aromatic heterocyclic rings with each other and includes, for example, a pyrrole ring, a furan ring, a thiophene ring, an imidazole ring, a pyrazole ring, a thiazole ring, an isothiazole ring, an oxazole ring, an isoxazole ring, a triazole ring, a tetrazole ring, an oxadiazole ring, a thiadiazole ring, a pyridine ring, a pyrazine ring, a pyrimidine ring, a pyridazine ring, an indole ring, a benzofuran ring, a benzothiophene ring, a benzimidazole ring, a benzoxazole ring, a benzisoxazole ring, a benzothiazole ring, a benzisothiazole ring, an indazole ring, a purine ring, a quinoline ring, an isoquinoline ring, a phthalazine ring, a naphthyridine ring, a quinoxaline ring, a quinazoline ring, a cinnoline ring and a pteridine ring.

The term [aromatic carbocyclic group] means a group formed from the aromatic carbocyclic rings described above and includes phenyl, naphthyl and anthryl.

The term [aromatic heterocyclic group] means a group formed from the aromatic heterocyclic rings described above and includes, for example, pyrrolyl, furyl, thienyl, imidazolyl, pyrazolyl, thiazolyl, isothiazolyl, oxazolyl, isoxazolyl, triazolyl, tetrazolyl, oxadiazolyl, thiadiazolyl, pyridyl, pyrazinyl, pyrimidinyl, pyridazinyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl and pteridinyl.

The term [lower alkylidene group] means a linear or branched alkylidene group having 1 to 6 carbon atoms and includes, for example, methylene, ethylidene, propylidene, isopropylidene and butylidene.

The term [lower alkenyl group] means a linear or branched alkenyl group having 2 to 6 carbon atoms and includes, for example, vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl and 4-pentenyl.

The term [lower alkynyl group] means a linear or branched alkynyl group having 2 to 6 carbon atoms and includes, for example, ethynyl, 2-propynyl, 1-methyl-2-propynyl, 2-butynyl, 1-methyl-2-butynyl and 2-pentynyl.

The term [cyclo(lower alkyl) group] means a cycloalkyl group having 3 to 6 carbon atoms and includes cyclopropyl, cyclobutyl, cyclopentyl and cyclohexyl.

The term [mono-, bi- or tricyclic aliphatic carbocyclic group] is a saturated or unsaturated aliphatic carbocyclic group and means a mono-, bi or tricyclic group. It includes, for example, cyclopropyl, cyclobutyl, cyclopentyl, cyclohexyl, cycloheptyl, cyclooctyl, cyclononyl, cyclodecyl, cycloundecyl, cyclododecyl, 1-cyclopentenyl, 2-cyclopentenyl, 3-cyclopentenyl, 1-cyclohexenyl, 2-cyclohexenyl, 1,3-cyclohexadienyl, 1-cycloheptenyl, 2-cycloheptenyl, 1,3-cycloheptadienyl, 1-cyclooctenyl, 2-cyclooctenyl, 3-cyclooctenyl, 4-cyclooctenyl, 1,3-cyclooctadienyl, 1-cyclononenyl, 2-cyclononenyl, 3-cyclononenyl, 4-cyclononenyl, 1,3-cyclononadienyl, 1-cyclodecenyl, 2-cyclodecenyl, 3-cyclodecenyl, 4-cyclodecenyl, 1,3-cyclodecadienyl, 1-cycloundecenyl, 2-cycloundecenyl, 1,3-cycloundecadienyl, 1-cyclododecenyl, 2-cyclododecenyl, 1,3-cyclododecadienyl, bicyclo[3.2.1]oct-1-yl, bicyclo[3.2.1]oct-2-yl, bicyclo[3.2.1]oct-3-yl, bicyclo[3.2.1]oct-6-yl, bicyclo[3.2.1]oct-8-yl, bicyclo[4.4.0]dec-1-yl, bicyclo[4.4.0]dec-2-yl, bicyclo[4.4.0]dec-3-yl, tricyclo[3.2.1.1$^{3.7}$]non-1-yl, tricyclo[3.3.1.1$^{3.7}$]dec-1-yl and tricyclo[3.3.1.1$^{3.7}$]dec-2-yl.

The term [mono- or bicyclic aliphatic nitrogen-containing heterocyclic group] means a saturated aliphatic heterocyclic group containing at least one nitrogen atom as a ring atom and means a mono- or bicyclic group. It includes, for example, a group represented by:

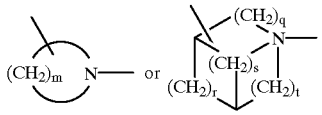

wherein m represents an integer of 3 to 9; q, r and t may be the same or different and represent an integer of 0 to 3; and s represents an integer of 1 to 4.

The term [lower alkoxycarbonyl group] means an alkoxycarbonyl group having the lower alkoxy groups described above, that is, means an alkoxycarbonyl group having 2 to 7 carbon atoms. It includes, for example, methoxycarbonyl, ethoxycarbonyl, propoxycarbonyl, isopropxycarbonyl, butoxycarbonyl, isobutoxycarbonyl, tert-butoxycarbonyl and pentyloxycarbonyl.

The term [lower alkylcarbamoyl group] means a carbamoyl group which is mono-substituted with the lower alkyl groups described above and includes, for example, methylcarbamoyl, ethylcarbamoyl, propylcarbamoyl, isopropylcarbamoyl, butylcarbamoyl, sec-butylcarbamoyl and tert-butylcarbamoyl.

The term [di(lower alkyl)carbamoyl group] means a carbamoyl group which is di-substituted with the lower alkyl groups described above and includes, for example, dimethylcarbamoyl, diethylcarbamoyl, ethylmethylcarbamoyl, dipropylcarbamoyl, methylpropylcarbamoyl and diisopropylcarbamoyl.

The term [lower alkylsulfonylamino group] means a sulfonylamino group having the lower alkyl groups described above and includes, for example, methylsulfonylamino, ethylsulfonylamino, propylsulfonylamino, isopropylsulfonylamino, butylsulfonylamino, sec-butylsulfonylamino and tert-butylsulfonylamino.

The term [(lower alkylamino)sulfonylamino group] means a sulfonylamino group having the lower alkylamino groups described above and includes, for example, (methylamino)sulfonylamino, (ethylamino)sulfonylamino, (propylamino)sulfonylamino, (isopropylamino)sulfonylamino, (butylamino)sulfonylamino, (secbutylamino)sulfonylamino and (tert-butylamino)sulfonylamino.

The term [(di-lower alkylamino)sulfonylamino group] means a sulfonylamino group having the di(lower alkyl)amino groups described above and includes, for example, (dimethylamino)sulfonylamino, (diethylamino)sulfonylamino, (ethylmethylamino)sulfonylamino, (dipropylamino)sulfonylamino, (methylpropylamino)sulfonylamino and (diisopropylamino)sulfonylamino.

The term [(lower alkylcarbamoyl)amino group] means an amino group which is mono-substituted with the lower alkylcarbamoyl groups described above and includes, for example, (methylcarbamoyl)amino, (ethylcarbamoyl)amino, (propylcarbamoyl)amino, (isopropylcarbamoyl)amino, (butylcarbamoyl)amino, (sec-butylcarbamoyl)amino and (tert-butylcarbamoyl)amino.

The term [(di-lower alkylcarbamoyl)amino group] means an amino group mono-substituted with the di(lower alkyl)carbamoyl groups described above and includes, for example, (dimethylcarbamoyl)amino, (diethylcarbamoyl)amino, (ethylmethylcarbamoyl)amino, (dipropylcarbamoyl)amino, (methylpropylcarbamoyl)amino and (diisopropylcarbamoyl)amino.

The term [lower alkylcarbamoyloxy group] means an oxy group having the lower alkylcarbamoyl groups described above and includes, for example, methylcarbamoyloxy, ethylcarbamoyloxy, propylcarbamoyloxy, isopropylcarbamoyloxy, butylcarbamoyloxy, sec-butylcarbamoyloxy and tert-butylcarbamoyloxy.

The term [di(lower alkyl)carbamoyloxy group] means an oxy group having the di(lower alkyl)carbamoyl groups described above and includes, for example, dimethylcarbamoyloxy, diethylcarbamoyloxy, ethylmethylcarbamoyloxy, dipropylcarbamoyloxy, methylpropylcarbamoyloxy and diisopropylcarbamoyloxy.

The term [cycloalkyl group having 3 to 10 carbon atoms] includes cyclopropyl, cyclobutyl, cyclopentyl, cyclohexyl, cycloheptyl, cyclooctyl, cyclononyl and cyclodecyl.

The term [salt] of the compound represented by Formula [I] means a conventional pharmaceutically acceptable salt and includes, for example, a base-addition salt of a carboxyl group when the compound has such a carboxyl group, and a acid-addition salt of an amino group when the compound has such an amino group, or of a basic heterocyclic ring when the compound has such a basic heterocyclic ring.

The above base-addition salt includes, for example, alkaline metal salts such as sodium salt and potassium salt; alkaline earth metal salts such as calcium salt and a magnesium salt; ammonium salts; and organic amine salts such as trimethylamine salt, triethylamine salt, dicyclohexyamine salt, ethanolamine salt, diethanolamine salt, triethanolamine salt, procaine salt and N,N'-dibenzylethylenediamine salt.

The above acid-addition salt includes, for example, inorganic acid salts such as hydrochloride, sulfate, nitrate, phosphate and perchlorate; organic acid salts such as maleate, fumarate, tartrate, citrate, ascorbate and trifluoroacetate; and sulfonates such as methanesulfonate, isethionate, bezenesulfonate and p-toluenesulfonate.

The term [ester] of the compound represented by Formula [I] means a conventional pharmaceutically acceptable ester of a carboxylic group if the compound has, for example, such a carboxylic group, and includes, for example, esters with lower alkyl groups such as methyl, ethyl, propyl, isopropyl, butyl, sec-butyl, tert-butyl, pentyl, isopentyl, neopentyl, cyclopropyl, cyclobutyl and cyclopentyl; esters with aralkyl groups such as benzyl and phenethyl; esters with lower alkenyl groups such as allyl and 2-butenyl; esters with lower alkoxyalkyl groups such as methoxymethyl, 2-methoxyethyl and 2-ethoxyethyl; esters with lower alkanoyloxyalkyl groups such as acetoxymethyl, pivaloyloxymethyl and 1-pivaloyloxyethyl; esters with lower alkoxycarbonylalkyl groups such as methoxycarbonylmethyl and isopropoxycarbonylmethyl; esters with lower carbooxyalkyl groups such as carboxymethyl; esters with lower alkoxycarbonyloxyalkyl groups such as 1-(ethoxycarbonyloxy)ethyl and 1-(cyclohexyloxycarbonyloxy)ethyl; esters with lower carbamoyloxyalkyl groups such as carbamoyloxymethyl; ester with phthalidyl; and esters with (5-substituted-2-oxo-1,3-dioxol-4-yl)methyl groups such as (5-methyl-2-oxo-1,3-dioxol-4-yl)methyl.

In order to more specifically disclose the compound of the present invention represented by the Formula [I] described above, various symbols used in Formula [I] shall be explained in further details with reference to the suitable specific examples thereof.

The compound of the present invention represented by Formula [I] has stereoisomers such as an optical isomer, a diastereoisomer and a geometrical isomer in a certain case, which are present depending on the forms of the substituents, and the compound of the present invention represented by Formula [I] includes all these stereoisomers and mixtures thereof.

In order to avoid unnecessary confusion in the present specification, a position number in the 2-oxoimidazole ring part of the compound of the present invention shall be settled as shown in the following formula [a] for the sake of convenience:

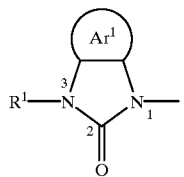

[a]

and the ring atoms of the aromatic carbo- or heterocyclic ring represented by

, which are not owned jointly by two or more rings, shall be numbered clockwise in order subsequently to the 2-oxoimidazole ring part described above.

Accordingly, when the aromatic carbo- or heterocyclic ring represented by

in the group represented by the formula [a] is a benzene ring, the position number of the above group is as shown in a formula [a']:

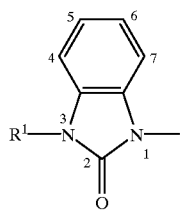

[a']

A compound represented by Formula [I-a] is included in the compound represented by Formula [I]:

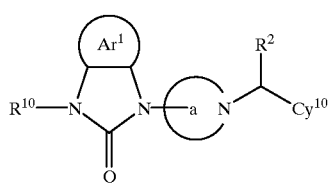

[I-a]

[wherein

represents an aromatic carbo- or heterocyclic ring which may have a substituent selected from the group consisting of a halogen atom, a lower alkyl group, an amino group, a lower alkylamino group, a di(lower alkyl)amino group, a hydroxyl group, a lower 2 alkoxy group and a carboxyl group; $Ar^2$ represents an aromatic carbo- or heterocyclic group which may have a substituent selected from the group consisting of a halogen atom, a lower alkyl group, an amino group, a lower alkylamino group, a di(lower alkyl)amino group, a hydroxyl group, a lower alkoxy group and a carboxyl group; $Cy^{10}$ represents a mono-, bi- or tricyclic aliphatic carbocyclic group having 3 to 20 carbon atoms, which may have a substituent selected from the group consisting of a halogen atom, a lower alkyl group, a lower alkylidene group, a lower alkenyl group, a lower alkynyl group, an amino group, a lower alkylamino group, a di(lower alkyl)amino group and a lower alkoxy group;

represents a mono- or bicyclic aliphatic nitrogen-containing heterocyclic group having 3 to 14 carbon atoms, which may have a substituent selected from the group consisting of a halogen atom, a lower alkenyl group, a lower alkynyl group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group, a di(lower alkyl) carbamoyl group and a group represented by —$R^{30}$; $R^{10}$ represents a hydrogen atom, a lower alkenyl group, a lower alkynyl group, a cyclo(lower alkyl) group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group or a di(lower alkyl)carbamoyl group, or a lower alkyl group which may have a substituent selected from the group consisting of a cyclo(lower alkyl) group, an amino group, a (lower alkyl)-amino group, a di(lower alkyl) amino group, a hydroxyl group, a lower alkoxy group, a carboxyl group, a lower alkoxycarbonyl group, a carbamoyl group, a lower alkylcarbamoyl group, a di(lower alkyl)-carbamoyl group and a group represented by —Ar²; R represents a hydrogen atom or a lower alkyl group; and R³⁰ represents a lower alkyl group which may have a substituent selected from the group consisting of an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group and a di(lower alkyl)carbamoyl group].

represents an aromatic carbo- or heterocyclic ring which may have a substituent selected from the group consisting of a halogen atom, a lower alkyl group, an amino group, a lower alkylamino group, a di(lower alkyl)amino group, a hydroxyl group, a lower alkoxy group and a carboxyl group, and it is subjected to ortho-condensation with the adjacent 2-oxoimidazole ring to form a condensed ring.

The term [an aromatic carbo- or heterocyclic ring which may have a substituent selected from the group consisting of a halogen atom, a lower alkyl group, an amino group, a lower alkylamino group, a di(lower alkyl)amino group, a hydroxyl group, a lower alkoxy group and a carboxyl group] means the non-substituted aromatic carbocyclic ring or aromatic heterocyclic ring described above, or the aromatic carbocyclic ring or aromatic heterocyclic ring described above which has a substituent in an optional substitutable position. The above substituents may be the same or different, and at least one, preferably one or two substituents can be selected from the group consisting of a halogen atom, a lower alkyl group, an amino group, a lower alkylamino group, a di(lower alkyl)amino group, a hydroxyl group, a lower alkoxy group and a carboxyl group.

Suitable examples of the halogen atom in the above substituents include a fluorine atom and a chlorine atom.

Suitable examples of the lower alkyl group in the above substituents include methyl and ethyl.

Suitable examples of the lower alkylamino group in the above substituent include methylamino and ethylamino.

Suitable examples of the di(lower alkyl)amino group in the above substituents include dimethylamino and diethylamino.

Suitable examples of the lower alkoxy group in the above substituents include methoxy, ethoxy and propoxy.

The above substituents are suitably a halogen atom and a lower alkyl group.

Suitable examples of the aromatic carbocyclic ring of

include a benzene ring, and suitable examples of the aromatic heterocyclic ring of

include a thiophene ring and a pyridine ring.

is suitably an aromatic carbocyclic ring which may have a substituent selected from the group consisting of a halogen atom, a lower alkyl group, an amino group, a lower alkylamino group, a di(lower alkyl)amino group, a hydroxyl group, a lower alkoxy group and a carboxyl group.

Accordingly,

includes, for example, a benzene ring, a 4-fluorobenzene ring, a 5-fluorobenzene ring, a 6-fluorobenzene ring, a 7-fluorobenzene ring, 4-chlorobenzene ring, a 5-chlorobenzene ring, a 6-chlorobenzene ring, a 7-chlorobenzene ring, 4-methylbenzene ring, a 5-methylbenzene ring, a 6-methylbenzene ring, a 7-methylbenzene ring, 4-methylaminobenzene ring, a 5-methylaminobenzene ring, a 6-methylaminobenzene ring, a 7-methylaminobenzene ring, 4-dimethylaminobenzene ring, a 5-dimethylaminobenzene ring, a 6-dimethylaminobenzene ring, a 7-dimethylaminobenzene ring, 4-methoxybenzene ring, a 5-methoxybenzene ring, a 6-methoxybenzene ring, a 7-methoxybenzene ring and a pyridine ring. Among them, a benzene ring and a 4-fluorobenzene ring are suitable.

In this case, the above position number shows the position number of the ring atom of the aromatic carbo- or heterocyclic ring, which is assigned when the above aromatic carbo- or heterocyclic ring is condensed with the 2-oxoimidazole ring.

Cy represents a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, an amino group, a lower alkylamino group, a di(lower alkyl)amino group, a lower alkoxy group and a group represented by —R⁴.

The term [a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, an amino group, a lower alkylamino group, a di(lower alkyl)amino group, a lower alkoxy group and a group represented by —R⁴] means the preceding non-substituted mono-, bi- or tricyclic aliphatic carbocyclic group having 3 to 20 carbon atoms or the preceding mono-, bi- or tricyclic aliphatic carbocyclic group having 3 to 20 carbon atoms, which has a substituent in an optional substitutable position. The above substituents may be the same or different, and at least one, preferably one or two substituents can be selected from the group consisting of a halogen atom, a lower alkylidene group, a lower alkenyl group, a lower alkynyl group, an amino group, a lower alkylamino group, a di(lower alkyl)amino group, a lower alkoxy group and a group represented by —R⁴.

Suitable examples of the halogen atom in the above substituents include a fluorine atom and a chlorine atom.

Suitable examples of the lower alkylidene group in the above substituents include methylene and ethylidene.

Suitable examples of the lower alkenyl group in the above substituents include vinyl, 1-propenyl and 2-propenyl.

Suitable examples of the lower alkynyl group in the above substituents include ethynyl and 2-propynyl.

Suitable examples of the lower alkylamino group in the above substituents include methylamino and ethylamino.

Suitable examples of the di(lower alkyl)amino group in the above substituents include dimethylamino and diethylamino.

Suitable examples of the lower alkoxy group in the above substituents include methoxy, ethoxy and propoxy.

$R^4$ represents a lower alkyl group which may have a substituent selected from the group consisting of a cycloalkyl group having 3 to 10 carbon atoms and an aromatic carbo- or heterocyclic group.

The term [a lower alkyl group which may have a substituent selected from the group consisting of a cycloalkyl group having 3 to 10 carbon atoms and an aromatic carbo- or heterocyclic group] means a non-substituted lower alkyl group or a lower alkyl group having a substituent in an optional substitutable position. The above substituents may be the same or different, and at least one, preferably one substituent can be selected from the group consisting of a cycloalkyl group having 3 to 10 carbon atoms and an aromatic carbo- or heterocyclic group.

Suitable examples of the cycloalkyl group having 3 to 10 carbon atoms in the above substituents include cyclohexyl, cycloheptyl and cyclooctyl.

Suitable examples of the aromatic carbocyclic group in the above substituents include phenyl.

Suitable examples of the aromatic heterocyclic group in the above substituents include furyl, thienyl and pyridyl.

Suitable examples of the lower alkyl group of $R^4$ include methyl, ethyl, propyl, isopropyl, butyl, sec-butyl, tert-butyl and pentyl.

Accordingly, $R^4$ includes, for example, methyl, ethyl, propyl, isopropyl, butyl, sec-butyl, tert-butyl, pentyl, cyclohexylmethyl, benzyl and pyridylmethyl, and among them, methyl, ethyl and propyl are suited.

A halogen atom, a lower alkylidene group and a group represented by —$R^4$ are suited to the substituent for Cy.

The mono-, bi- or tricyclic aliphatic carbocyclic group having 3 to 20 carbon atoms of Cy is preferably a group containing no benzene ring as a constitutional unit for the above aliphatic carbocyclic group and is suitably a mono-, bi- or tricyclic aliphatic carbocyclic group having 6 to 20, more preferably 8 to 12 carbon atoms. To be more specific, suitable examples thereof include, in addition to cyclohexyl, cycloheptyl, cyclooctyl, cyclononyl, cyclodecyl, 1-cyclooctenyl, 1-cyclononenyl, 1-cyclodecenyl, bicyclo[3.2.1]oct-3-yl, bicyclo[4.4.0]dec-2-yl, bicyclo[4.4.0]dec-3-yl, tricyclo[3.2.1.1$^{3.7}$]non-1-yl and tricyclo[3.3.1.1$^{3.7}$]dec-1-yl. In particular, cyclooctyl is preferred.

Accordingly, suitable examples of Cy include cyclopropyl, cyclobutyl, cyclopentyl, cyclohexyl, cycloheptyl, cyclooctyl, cyclononyl, cyclodecyl, cycloundecyl, cyclododecyl, 1-cyclopentenyl, 2-cyclopentenyl, 3-cyclopentenyl, 1-cyclohexenyl, 2-cyclohexenyl, 1,3-cyclohexadienyl, 1-cycloheptenyl, 2-cycloheptenyl, 1,3-cycloheptadienyl, 1-cyclooctenyl, 2-cyclooctenyl, 3-cyclooctenyl, 4-cyclooctenyl, 1,3-cyclooctadienyl, 1-cyclononenyl, 2-cyclononenyl, 3-cyclononenyl, 4-cyclononenyl, 1,3-cyclononadienyl, 1-cyclodecenyl, 2-cyclodecenyl, 3-cyclodecenyl, 4-cyclodecenyl, 1,3-cyclodecadienyl, 1-cycloundecenyl, 2-cycloundecenyl, 1,3-cycloundecadienyl, 1-cyclododecenyl, 2-cyclododecenyl, 1,3-cyclododecadienyl, bicyclo[3.2.1]oct-1-yl, bicyclo[3.2.1]oct-2-yl, bicyclo[3.2.1]oct-3-yl, bicyclo[3.2.1]oct-6-yl, bicyclo[3.2.1]oct-8-yl, bicyclo[4.4.0]dec-1-yl, bicyclo[4.4.0]dec-2-yl, bicyclo[4.4.0]dec-3-yl, tricyclo[3.2.1.1$^{3.7}$]non-1-yl, tricyclo[3.3.1.1$^{3.7}$]dec-1-yl, tricyclo-[3.3.1.1$^{7}$]dec-2-yl, 5,5-difluorocyclooctyl, 1-methylcyclooctyl, 2-methylcyclooctyl, 1-ethylcyclooctyl, 1-propylcyclooctyl, 2-methylenecyclooctyl, 1-cyclohexylmethylcyclooctyl and 1-benzylcyclooctyl. Among them, suited are cyclohexyl, cycloheptyl, cyclooctyl, cyclononyl, cyclodecyl, 1-cyclooctenyl, 1-cyclononenyl, 1-cyclodecenyl, bicyclo-[3.2.1]oct-3-yl, bicyclo[4.4.0]dec-2-yl, bicyclo[4.4.0]dec-3-yl, tricyclo[3.2.1.1$^{3.7}$]non-1-yl, tricyclo[3.2.1.1$^{3.7}$]dec-1-yl, 1-methylcyclooctyl, 2-methylcyclooctyl, 1-ethylcyclooctyl, 1-propylcyclooctyl and 2-methyleecyclooctyl.

represents a mono- or bicyclic aliphatic nitrogen-containing heterocyclic group having 3 to 14 carbon atoms, which may have a substituent selected from the group consisting of a halogen atom, a lower alkylidene group, a lower alkenyl group, a lower alkynyl group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group, a di(lower alkyl)carbamoyl group and a group represented by —$R^3$. It is bonded to the adjacent group represented by

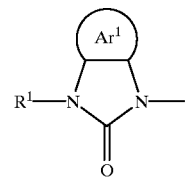

(wherein

and $R^1$ are synonymous with those described above) on an optional substitutable ring carbon atom and bonded to the group represented by

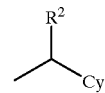

(wherein Cy and $R^2$ are synonymous with those described above) on a ring nitrogen atom.

The term [a mono- or bicyclic aliphatic nitrogen-containing heterocyclic group having 3 to 14 carbon atoms, which may have a substituent selected from the group consisting of a halogen atom, a lower alkylidene group, a lower alkenyl group, a lower alkynyl group, an amino group, a lower alkylamino group, a di(lower alkyl)-amino group, a hydroxyl group, a lower alkoxy group, a carboxyl group, a lower alkoxycarbonyl group, a carbamoyl group, a lower alkylcarbamoyl group, a di(lower alkyl)carbamoyl group and a group 3 represented by —$R^1$] means the preceding non-substituted mono- or bicyclic aliphatic nitrogen-containing heterocyclic group having 3 to 14 carbon atoms or the preceding mono- or bicyclic aliphatic nitrogen-containing heterocyclic group having 3 to 14 carbon atoms, which has a substituent in an optional substitutable position. The above substituents may be the same or different, and at least one, preferably one or two substituents can be selected from the group consisting of a mono- or bicyclic aliphatic nitrogen-containing heterocyclic group having 3 to 14 carbon atoms, which may have a substituent selected from the group consisting of a halogen atom, a lower alkylidene group, a lower alkenyl group, a lower alkynyl group, an amino group, a lower alkylamino group, a di(lower alkyl)-amino group, a hydroxyl group, a lower alkoxy group, a carboxyl group, a lower alkoxycarbonyl group, a carbamoyl group, a lower alkylcarbamoyl group, a di(lower alkyl) carbamoyl group and a group represented by —$R^3$.

Suitable examples of the halogen atom in the above substituents include a fluorine atom and a chlorine atom.

Suitable examples of the lower alkylidene group in the above substituents include methylene and ethylidene.

Suitable examples of the lower alkenyl group in the above substituents include vinyl, 1-propenyl and 2-propenyl.

Suitable examples of the lower alkynyl group in the above substituents include ethynyl and 2-propynyl.

Suitable examples of the lower alkylamino group in the above substituents include methylamino and ethylamino. Suitable examples of the di(lower alkyl)amino group in the above substituents include dimethylamino and diethylamino.

Suitable examples of the lower alkoxy group in the above substituents include methoxy, ethoxy and propoxy.

Suitable examples of the lower alkoxycarbonyl group in the above substituents include methoxycarbonyl and ethoxycarbonyl.

Suitable examples of the lower alkylcarbamoyl group in the above substituents include methylcarbamoyl and ethylcarbamoyl.

Suitable examples of the di(lower alkyl)carbamoyl group in the above substituents include dimethylcarbamoyl and diethylcarbamoyl.

$R^3$ represents a lower alkyl group which may have a substituent selected from the group consisting of an amino group, a lower alkylsulfonylamino group, an aminosulfonylamino group, a (lower alkylamino)sulfonylamino group, a (di-lower alkylamino)-sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group, an aromatic heterocyclic group and a group represented by —$R^5$.

The term [a lower alkyl group which may have a substituent selected from the group consisting of an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group, an aromatic heterocyclic group and a group represented by —$R^5$] means the preceding non-substituted lower alkyl group or the preceding lower alkyl group having a substituent in an optional substitutable position. The above substituents may be the same or different, and at least one, preferably one or two substituents can be selected from the group consisting of a lower alkyl group which may have a substituent selected from the group consisting of an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group, an aromatic heterocyclic group and a group represented by —$R^6$.

Suitable examples of the lower alkylsulfonylamino group in the above substituents include methylsulfonylamino and ethylsulfonylamino.

Suitable examples of the (lower alkylamino)sulfonylamino group in the above substituents include (methylamino)sulfonylamino and (ethylamino)sulfonylamino.

Suitable examples of the (di-lower alkylamino)sulfonylamino group in the above substituents include (dimethylamino)sulfonylamino and (diethylamino)sulfonylamino.

Suitable examples of the (lower alkylcarbamoyl)amino group in the above substituents include (methylcarbamoyl)amino and (ethylcarbamoyl)amino.

Suitable examples of the (di-lower alkylcarbamoyl)amino group in the above substituents include (dimethylcarbamoyl)amino and (diethylcarbamoyl)amino.

Suitable examples of the lower alkylcarbamoyloxy group in the above substituents include methylcarbamoyloxy and ethylcarbamoyloxy.

Suitable examples of the di(lower alkyl)carbamoyloxy group in the above substituents include dimethylcarbamoyloxy and diethylcarbamoyloxy.

Suitable examples of the lower alkoxycarbonyl group in the above substituents include methoxycarbonyl and ethoxycarbonyl.

Suitable examples of the lower alkylcarbamoyl group in the above substituents include methylcarbamoyl and ethylcarbamoyl.

Suitable examples of the di(lower alkyl)carbamoyl group in the above substituents include dimethylcarbamoyl and diethylcarbamoyl.

Suitable examples of the aromatic heterocyclic group in the above substituents include triazolyl and tetrazolyl.

$R^5$ represents a lower alkylamino group, a di(lower alkyl)amino group or a lower alkoxy group, which may have an aromatic carbo- or heterocyclic group.

The term [a lower alkylamino group, a di(lower alkyl)amino group or a lower alkoxy group, which may have an aromatic carbo- or heterocyclic group] means the preceding non-substituted lower alkylamino group, di(lower alkyl) amino group or lower alkoxy group, or the preceding lower alkylamino group, di(lower alkyl)amino group or lower alkoxy group, which has an aromatic carbo- or heterocyclic group as a substituent in an optional substitutable position.

A suitable example of the aromatic carbocyclic group in the above substituent includes phenyl, and a suitable example of the aromatic heterocyclic group in the above substituent includes pyridyl.

Suitable examples of the lower alkylamino group of $R^5$ include methylamino and ethylamino.

Suitable examples of the di(lower alkyl)amino group of $R^5$ include dimethylamino and diethylamino.

Suitable examples of the lower alkoxy group of $R^5$ include methoxy, ethoxy and propoxy.

Suited as $R^5$ is the preceding lower alkoxy group which has an aromatic carbo- or heterocyclic group as a substituent in an optional substitutable position.

Accordingly, $R^5$ includes, for example, methylamino, dimethylamino, benzylamino, benzyl(methyl)amino, methoxy, benzyloxy, 2-pyridylmethylamino, 3-pyridylmethylamino, 4-pyridylmethylamino, 2-pyridylmethyloxy, 3-pyridylmethyloxy and 4-pyridylmethyloxy. Among them, methoxy, benzyloxy and 3-pyridylmethyloxy are suited.

Suited as a substituent for $R^3$ are an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxycarbonyl group and a group represented by —$R^5$. More preferably suited are a lower alkylsulfonylamino group, an aminosulfonylamino group, a carbamoylamino group, a hydroxyl group and a group represented by —$R^5$.

Suitable examples of the lower alkyl group of $R^3$ include methyl, ethyl, propyl, isopropyl and isobutyl.

Accordingly, suitable examples of $R^3$ include methyl, ethyl, aminomethyl, 1-aminoethyl, 2-aminoethyl, 3-aminopropyl, methylaminomethyl, 1-methylaminoethyl, 2-methylaminoethyl, dimethylaminomethyl, 1-dimethylaminoethyl, 2-dimethylaminoethyl, 3-methylaminopropyl, 3-dimethylaminopropyl, (methylsulfonylamino)methyl, 2-(methylsulfonylamino)ethyl, (aminosulfonylamino)methyl, 2-(aminosulfonylamino)ethyl, [(dimethylaminosulfonyl) amino] methyl, 2-[(dimethylaminosulfonyl)amino] ethyl, (carbamoylamino)methyl, 2-(carbamoylamino)ethyl, hydroxymethyl, 1-hydroxyethyl, 2-hydroxyethyl, 1,2-dihydroxyethyl, 1-hydroxypropyl, 3-hydroxypropyl, methoxymethyl, 1-methoxyethyl, 2-methoxyethyl, carbamoyloxymethyl, 2-(carbamoyloxy)ethyl, carboxymethyl, 1-carboxyethyl, 2-carboxyethyl, methoxycarbonylmethyl, 1-methoxycarbonylethyl, 2-methoxycarbonylethyl, ethoxycarbonylmethyl, 1-ethoxycarbonylethyl, 2-ethoxycarbonylethyl, carbamoylmethyl, 1-carbamoylethyl, 2-carbamoylethyl, methylcarbamoylmethyl, 1-methylcarbamoylethyl, 2-methylcarbamoylethyl, dimethylcarbamoylmethyl, 1-dimethylcarbamoylethyl, 2-dimethylcarbamoylethyl, benzyloxymethyl, (2-pyridylmethyloxy)methyl, (3-pyridylmethyloxy)methyl and (4-pyridylmethyloxy) methyl. Among them, suited are methyl, hydroxymethyl, 1-hydroxyethyl, 1-hydroxypropyl, (methylsulfonylamino) methyl, (aminosulfonylamino)methyl, (carbamoylamino) methyl and (3-pyridylmethyloxy)methyl.

A lower alkoxycarbonyl soup and a group represented by —$R^3$ are suitable as a substituent for

The mono- or bicyclic aliphatic nitrogen-containing heterocyclic group having 3 to 14 carbon atoms of

includes, for example, a group represented by

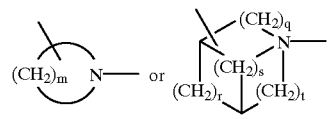

wherein m, q, r, t and s are synonymous with those described above. To be more specific, suited are, for example, 1,3-pyrrolidinediyl, 1,3-piperidinediyl, 1,4-piperidinediyl, 2-azabicyclo[2.2.2]octa-2, 5-diyl and 8-azabicyclo[4.3.0] nona-2,8-diyl. Among them, 1,4-piperidinediyl and 2-azabicyclo[2.2.2]octa-2,5-diyl are suitable.

Accordingly,

includes, for example, 1,3-pyrrolidinediyl, 1,3-piperidinediyl, -piperidinediyl, 2-azabicyclo[2.2.2]-octa-2, 5-diyl, 8-azabicyclo[4.3.0]nona-2,8-diyl, 3-methylene-1,4-piperidinediyl, 3-vinyl-1,4-piperidinediyl, 3-amino-1,4-piperidinediyl, 3-carboxy-1,4-piperidinediyl, 4-methoxycarbonyl-1,4-piperidinediyl, 2-ethoxycarbonyl-1, 4-piperidinediyl, 3-ethoxycarbonyl-1,4-piperidinediyl, 4-ethoxycarbonyl-1,4-piperidinediyl, 2,3-diethoxycarbonyl-1,4-piperidinediyl, 2,4-diethoxycarbonyl-1,4-piperidinediyl, 3,4-diethoxycarbonyl-1,4-piperidinediyl, 3-carbamoyl-1,4-piperidinediyl, 2-methyl-1,4-pyperidinediyl, 3-methyl-1,4-piperidinediyl, 4-methyl-1,4-piperidinediyl, 2,3-dimethyl-1, 4-piperidinediyl, 2,4-dimethyl-1,4-piperidinediyl, 3,3-dimethyl-1,4-piperidinediyl, 3,4-dimethyl-1,4 -piperidinediyl, 3,5-dimethyl-1,4-piperidinediyl, 3-ethyl-1, 4-piperidinediyl, 2-aminomethyl-1,4-piperidinediyl, 3-aminomethyl-1,4-piperidinediyl, 4-aminomethyl-1,4-piperidinediyl, 2,3-bis(aminomethyl)-1,4-piperidinediyl, 2,4-bis(aminomethyl)-1,4-piperidinediyl, 3,4-bis (aminomethyl)-1,4-piperidinediyl, 3-(2-aminoethyl)-1,4-piperidinediyl, 3-(3-aminopropyl)-1,4-piperidinediyl, 3-methylaminomethyl-1,4-piperidinediyl, 3-dimethylaminomethyl-1,4-piperidinediyl, 3-(2-dimethylaminoethyl)-1,4-piperidinediyl, 3-(3-methylaminopropyl)-1,4-piperidinediyl, 3-(3-dimethylaminopropyl)-1,4-piperidinediyl, 3-(methylsulfonylamino)methyl-1,4-piperidinediyl, 3-(aminosulfonylamino)methyl-1,4-piperidinediyl, 3-[(dimethylaminosulfonyl)amino]methyl-1,4-piperidinediyl, 3-(carbamoylamino)-methyl-1,4-piperidinediyl, 2-hydroxymethyl-1,4-piperidinediyl, 3-hydroxymethyl-1,4-piperidinediyl, 4-hydroxymethyl-1,4-piperidinediyl, 2,3-bis(hydroxymethyl)-1,4-piperidinediyl, 2,4-bis(hydroxymethyl)-1,4-piperidinediyl, 3,3-bis (hydroxymethyl)-1,4-piperidinediyl, 3,4-bis (hydroxymethyl)-1,4-piperidinediyl, 3,5-bis (hydroxymethyl)-1,4-piperidinediyl, 3-(1-hydroxyethyl)-1,4-piperidinediyl, 3-(2-hydroxyethyl)-1,4-pyperidinediyl, 3-(1,2-dihydroxyethyl)-1,4-piperidinediyl, 3-(1-hydroxypropyl)-1,4-piperidinediyl, 3-(3-hydroxypropyl)-1,4-piperidinediyl, 2-methoxymethyl-1,4-piperidinediyl, 3-methoxymethyl-1,4-piperidinediyl, 4-methoxymethyl-1,4-piperidinediyl, 2,3-bis(methoxymethyl)-1,4-piperidinediyl, 2,4-bis(methoxymethyl)-1,4-piperidinediyl, 3,4-bis(methoxymethyl)-1,4-piperidinediyl, 3-carbamoyloxymethyl-1,4-piperidinediyl, 3-(2-ethoxycarbonylethyl)-1,4-piperidinediyl, 3-benzyloxymethyl-1,4-piperidinediyl, 3-(2-pyridylmethyloxy)methyl-1,4-piperidinediyl, 3-(3-pyridylmethyloxy)methyl-1,4-piperidinediyl, 3-(4-pyridylmethyloxy)methyl-1,4-piperidinediyl and 3-(5-tetrazolylmethyl)-1,4-piperidinediyl. Among them, suited are 1,4-piperidinediyl, 2-azabicyclo[2.2.2]octa-2,5-diyl, 4-methoxycarbonyl-1,4-piperidinediyl, 3-methyl-1,4-piperidinediyl, 3-(methylsulfonylamino)methyl-1,4-piperidinediyl, 3-(aminosulfonylamino)methyl-1,4-piperidinediyl, 3-(carbamoylamino)methyl-1,4-piperidinediyl, 2-hydroxymethyl-1,4-piperidinediyl, 3-hydroxymethyl-1,4-piperidinediyl, 3-(1-hydroxyethyl)-1,4-piperidinediyl, 3-(1-hydroxypropyl)-1,4-piperidinediyl and 3-(3-pyridylmethyloxy)-methyl-1,4-piperidinediyl.

$R^1$ represents a hydrogen atom, a lower alkenyl group, a lower alkynyl group, a cyclo(lower alkyl) group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group or a di(lower alkyl)carbamoyl group, or a lower alkyl group which may have a substituent selected from the group consisting of a halogen atom, a cyclo(lower alkyl) group, an amino group, a lower alkylamino group, a di(lower alkyl)amino group, a (lower alkyl) sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl) carbamoyl group and a group represented by —$Ar^2$ Suitable examples of the lower alkenyl group represented by $R^1$ include vinyl, 1-propenyl and 2-propenyl.

Suitable examples of the lower alkynyl group represented by $R^1$ include ethynyl and 2-propynyl.

Suitable examples of the cyclo(lower alkyl) group represented by $R^1$ include cyclopropyl, cyclobutyl and cyclopentyl.

Suitable examples of the lower alkylamino group represented by $R^1$ include methylamino and ethylamino.

Suitable examples of the di(lower alkyl)amino group represented by $R^1$ include dimethylamino and diethylamino.

Suitable examples of the lower alkoxy group represented by $R^1$ include methoxy, ethoxy and propoxy.

Suitable examples of the lower alkoxycarbonyl group represented by $R^1$ include methoxycarbonyl and ethoxycarbonyl.

Suitable examples of the lower alkylcarbamoyl group represented by $R^1$ include methylcarbamoyl and ethylcarbamoyl.

Suitable examples of the di(lower alkyl)carbamoyl group represented by $R^1$ include dimethylcarbamoyl and diethylcarbamoyl.

The term [a lower alkyl group which may have a substituent selected from the group consisting of a halogen atom, a cyclo(lower alkyl) group, an amino group, a lower alkylamino group, a di(lower alkyl)amino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl) carbamoyl group and a group represented by —$Ar^2$] means the preceding non-substituted lower alkyl group or the preceding lower alkyl group having a substituent in an optional substitutable position. The above substituents may be the same or different, and at least one, preferably one or two substituents can be selected from the group consisting of a halogen atom, a cyclo(lower alkyl) group, an amino group, a lower alkylamino group, a di(lower alkyl)amino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)-amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl) carbamoyl group and a group represented by —$Ar^2$.

Suitable examples of the halogen atom in the above substituents include a fluorine atom and the like.

Suitable examples of the cyclo(lower alkyl) group in the above substituents include cyclopropyl and cyclobutyl.

Suitable examples of the lower alkylamino group in the above substituents include methylamino and ethylamino.

Suitable examples of the di(lower alkyl)amino group in the above substituents include dimethylamino and diethylamino.

Suitable examples of the lower alkylsulfonylamino group in the above substituents include methylsulfonylamino and ethylsulfonylamino.

Suitable examples of the (lower alkylamino) sulfonylamino group in the above substituents include (methylamino)sulfonylamino and (ethylamino) sulfonylamino.

Suitable examples of the (di-lower alkylamino) sulfonylamino group in the above substituents include (dimethylamino)sulfonylamino and (diethylamino) sulfonylamino.

Suitable examples of the (lower alkylcarbamoyl)amino group in the above substituents include (methylcarbamoyl) amino and (ethylcarbamoyl)amino.

Suitable examples of the (di-lower alkylcarbamoyl)amino group in the above substituents include (dimethylcarbamoyl)amino and (diethylcarbamoyl)amino.

Suitable examples of the lower alkoxy group in the above substituents include methoxy, ethoxy and propoxy.

Suitable examples of the lower alkylcarbamoyloxy group in the above substituents include methylcarbamoyloxy and ethylcarbamoyloxy.

Suitable examples of the di(lower alkyl)carbamoyloxy group in the above substituents include dimethylcarbamoyloxy and diethylcarbamoyloxy.

Suitable examples of the lower alkoxycarbonyl group in the above substituents include methoxycarbonyl and ethoxycarbonyl.

Suitable examples of the lower alkylcarbamoyl group in the above substituents include methylcarbamoyl and ethylcarbamoyl.

Suitable examples of the di(lower alkyl)carbamoyl group in the above substituents include dimethylcarbamoyl and diethylcarbamoyl.

$Ar^2$ represents an aromatic carbo- or heterocyclic group which may have a substituent selected from the group consisting of a halogen atom, a lower alkyl group, an amino group, a lower alkylamino group, a di(lower alkyl)amino group, a hydroxyl group, a lower alkoxy group and a carboxyl group.

The term [an aromatic carbo- or heterocyclic group which may have a substituent selected from the group consisting of a halogen atom, a lower alkyl group, an amino group, a lower alkylamino group, a di(lower alkyl)amino group, a hydroxyl group, a lower alkoxy group and a carboxyl group] means the non-substituted aromatic carbocyclic group or aromatic heterocyclic group described above, or the aromatic carbocyclic group or aromatic heterocyclic group described above which has a substituent in an optional substitutable position. The above substituents may be the same or different, and at least one, preferably one or two substituents can be selected from the group consisting of a halogen atom, a lower alkyl group, an amino group, a lower alkylamino group, a di(lower alkyl)amino group, a hydroxyl group, a lower alkoxy group and a carboxyl group.

Suitable examples of the halogen atom in the above substituents include a fluorine atom and a chlorine atom.

Suitable examples of the lower alkyl group in the above substituents include methyl and ethyl.

Suitable examples of the lower alkylamino group in the above substituent include methylamino and ethylamino.

Suitable examples of the di(lower alkyl)amino group in the above substituents include dimethylamino and diethylamino.

Suitable examples of the lower alkoxy group in the above substituents include methoxy, ethoxy and propoxy.

The above substituents are suitably a halogen atom and a lower alkyl group.

Suitable examples of the aromatic carbocyclic group of $Ar^2$ include phenyl, and suitable examples of the aromatic heterocyclic group of $Ar^2$ include pyridyl.

Accordingly, suitable examples of $Ar^2$ include phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-methylaminophenyl, 3-methylaminophenyl, 4-methylaminophenyl, 2-dimethylaminophenyl, 3-dimethylaminophenyl, 4-dimethylaminophenyl, 2-methoxyphenyl, 3-methoxyphenyl, 4-methoxyphenyl, 2-pyridyl, 3-pyridyl and 4-pyridyl. Among them, phenyl, 2-pyridyl, 3-pyridyl and 4-pyridyl are suitable.

Suitable examples of the substituent for the lower alkyl group of $R^1$ include a halogen atom, a cyclo(lower alkyl) group, an amino group, a lower alkylamino group, a di(lower alkyl)amino group, a (lower alkyl)sulfonylamino group, an aminosulfonylamino group, a (lower alkylamino)sulfonylamino group, a (di-lower alkylamino)sulfonylamino group, a carbamoylamino group, a hydroxyl group, a lower alkoxy group, a carboxyl group and a group represented by —$Ar^2$.

Suitable examples of the lower alkyl group of $R^1$ include methyl, ethyl, propyl, isopropyl and isobutyl.

Accordingly, suitable examples of the lower alkyl group represented by $R^1$ which may have the substituents described above include methyl, ethyl, propyl, isopropyl, isobutyl, 2-fluoroethyl, 2,2-difluoroethyl, 2,2,2-trifluoroethyl, cyclopropylmethyl, 2-aminoethyl, 2-methylaminoethyl, 2-dimethylaminoethyl, 2-diethylaminoethyl, 2-(methylsulfonylamino)ethyl, 2-(aminolsulfonylamino) ethyl, 2-[(dimethylaminosulfonyl)amino]ethyl, 2-(carbamoylamino)ethyl, 2-hydroxyethyl, 3-hydroxypropyl, methoxymethyl, 2-methoxyethyl, 2-(carbamoyloxy)ethyl, carboxymethyl, benzyl, 2-pyridylmethyl, 3-pyridylmethyl and 4-pyridylmethyl. Among them, suitable are methyl, ethyl, propyl, isopropyl, isobutyl, 2-fluoroethyl, 2,2-difluoroethyl, cyclopropylmethyl, 2-aminoethyl, 2-methylaminoethyl, 2-dimethylaminoethyl and 2-hydroxyethyl.

Suitable examples of R include a hydrogen atom or a lower alkyl group which may have a substituent selected from the group consisting of a halogen atom, a cyclo(lower alkyl) group, an amino group, a lower alkylamino group, a di(lower alkyl)amino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group and a group represented by —$Ar^2$.

Accordingly, suitable examples of $R^1$ include a hydrogen atom, 2-propenyl, 2-propynyl, cyclobutyl, cyclopentyl, dimethylamino, hydroxyl, methoxy, ethoxycarbonyl, methyl, ethyl, propyl, isopropyl, isobutyl, 2-fluoroethyl, 2,2-difluoroethyl, 2,2,2-trtifluoroethyl, cyclopropylmethyl, 2-aminoethyl, 2-methylaminoethyl, 2-dimethylaminoethyl, 2-diethylaminoethyl, 2-(methylsulfonylamino)ethyl, 2-(aminosulfonylamino)ethyl, 2-[(dimethylaminosulfonyl)amino]ethyl, 2-(carbamoylamino)ethyl, 2-hydroxyethyl, 3-hydroxyethyl, methoxymethyl, 2-methoxyethyl, 2-(carbamoyloxy)ethyl, carboxymethyl, benzyl, 2-pyridylmethyl, 3-pyridylmethyl and 4-pyridylmethyl. Among them, suitable are a hydrogen atom, 2-propynyl, hydroxyl, methyl, ethyl, propyl, isopropyl, isobutyl, 2-fluoroethyl, 2,2-difluoroethyl, cyclopropylmethyl, 2-aminoethyl, 2-methylaminoethyl, 2-dimethylaminoethyl and 2-hydroxyethyl.

$R^2$ represents a hydrogen atom or a lower alkyl group.

Suitable examples of $R^2$ include a hydrogen atom, methyl, ethyl and propyl, more preferably a hydrogen atom and methyl.

Next, the production process of the compound of the present invention shall be explained.

The compound of the present invention represented by Formula [I] can be produced, for example, by methods shown in the following production process 1, 2, 3, 4, 5, 6, 7, 8, 9 or 10.

Production Process 1

A compound represented by Formula [II]:

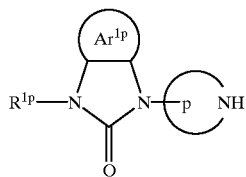

[wherein

represents an aromatic carbo- or heterocyclic ring which may have a substituent selected from the group consisting of a halogen atom, a lower alkyl group, a di(lower alkyl)amino group and a lower alkoxy group, and an amino group, a lower alkylamino group, a hydroxyl group and a carboxyl group, which may be protected; $Ar^{2p}$ represents an aromatic carbo- or heterocyclic group which may have a substituent selected from the group consisting of a halogen atom, a lower alkyl group, a di(lower alkyl)amino group and a lower alkoxy group, and an amino group, a lower alkylamino group, a hydroxyl group and a carboxyl group, which may be protected;

represents a mono- or bicyclic aliphatic nitrogen-containing herocyclic group having 3 to 14 carbon atoms, which may have a substituent selected from the group consisting of a halogen atom, a lower alkylidene group, a lower alkenyl group, a lower alkynyl group, a di(lower alkyl)amino group, a lower alkoxy group, a lower alkoxycarbonyl group, a di(lower alkyl)carbamoyl group and a group represented by —$R^{3p}$, and an amino group, a lower alkylamino group, a hydroxyl group, a carboxyl group, a carbamoyl group and a lower alkylcarbamoyl group, which may be protected; $R^{1p}$ represents a hydrogen atom, a lower alkenyl group, a lower alkynyl group, a cyclo(lower alkyl) group, a di(lower alkyl)amino group, a lower alkoxy group, a lower alkoxycarbonyl group or a di(lower alkyl)carbamoyl group, or an amino group, a lower alkylamino group, a hydroxyl group, a carboxyl group, a carbamoyl group or a lower alkylcarbamoyl group, which may be protected, or a lower alkyl group which may have a substituent selected from the group consisting of a halogen atom, a cyclo(lower alkyl) group, a di(lower alkyl)amino group, a lower alkoxy group, a di(lower alkyl)carbamoyloxy group, a lower alkoxycarbonyl group, a di(lower alkyl)carbamoyl group and a group represented by —$Ar^{2p}$, and an amino group, a lower alkylamino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a carboxyl group, a carbamoyl group and a lower alkylcarbamoyl group, which may be protected; $R^{3p}$ represents a lower alkyl group which may have a substituent selected from the group consisting of a di(lower alkyl)carbamoyloxy group, a lower alkoxycarbonyl group, a di(lower alkyl)carbamoyl group, an aromatic heterocyclic group and a group represented by —$R^{6p}$, and an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a carboxyl group, a carbamoyl group and a lower alkylcarbamoyl group, which may be protected; and $R^{5p}$ represents a lower alkylamino group which may be protected, a (dilower alkyl) amino group or a lower alkoxy group, which may have an aromatic carbo- or heterocyclic group] is reacted with a compound represented by Formula [III]

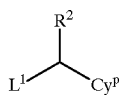

[wherein $Cy^p$ represents a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, a di(lower alkyl)amino group, a lower alkoxy group and a group represented by —$R^4$, and an amino group and a lower alkylamino group, which may be protected; $L^1$ represents a leaving group; and $R^2$ and $R^4$ are synonymous with those described above] to prepare a compound represented by Formula [IV]:

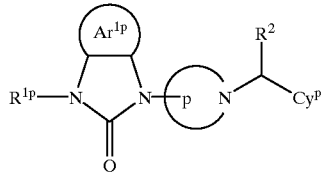

[wherein

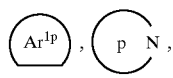

$Cy^p$, $R^{1p}$ and $R^2$ are synonymous with those described above], and the protective groups are removed if necessary, whereby the compound represented by Formula [I] can be obtained.

Examples of the leaving group represented by $L^1$ include a halogen atom such as a chlorine atom, a bromine atom or an iodine atom, an organic sulfonyl group such as methanesulfonyl, ethanesulfonyl and benzenesulfonyl, and an organic sulfonyloxy group such as methanesulfonyloxy, trifluoromethanesulfonyloxy and p-toluene-sulfonyloxy.

In the reaction described above, when an amino group, a hydroxyl group and a carboxyl group which do not take part in the reaction are present in the reaction substances, it is preferred that the above amino group, hydroxyl group and carboxyl group are suitably protected with a protective group for an amino group, a protective group for a hydroxyl group and a protective group for a carboxyl group and the reaction is then carried out and that the above protective groups are removed after finishing the reaction.

Preferred as the protective group for an amino group are an aralkyl group such as, for example, benzyl, p-methoxybenzyl, 3,4-dimethoxybenzyl, o-nitrobenzyl, p-nitrobenzyl, benzhydryl and trityl; a lower alkanoyl group such as, for example, formyl, acetyl, propionyl, butyryl and pivaloyl; an arylalkanoyl group such as, for example, phenylacetyl and phenoxyacetyl; a lower alkoxycarboyl group such as, for example, methoxycarbonyl, ethoxycarbonyl, propyloxycarbonyl and tert-butoxycarbonyl; an aralkyloxycarboyl group such as, for example, benzyloxycarbonyl, p-nitrobenzyloxycarbonyl and phenethyloxycarbonyl; a lower alkylsilyl group such as, for example, trimethylsilyl and tert-butyldimethylsilyl; for example, a phthaloyl group; and an aralkylidene group such as, for example, benzylidene, p-chlorobenzylidene and o-nitrobenzylidene. In particular, acetyl, pivaloyl, benzoyl, ethoxycarbonyl and tert-butoxycarbonyl are preferred.

Preferred as the protective group for a hydroxyl group are an alkylsilyl group such as, for example, trimethylsilyl and tertbutyldimethylsilyl; a lower alkoxymethyl group such as, for example, methoxymethyl and 2-methoxyethoxymethyl; for example, a tetrahydropyranyl group; for example, a trimethylsilylethoxymethyl group; an aralkyl group such as, for example, benzyl, p-methoxybenzyl, 2,3-dimethoxybenzyl, o-nitrobenzyl, p-nitrobenzyl and trityl; and an acyl group such as, for example, formyl and acetyl. In particular, methoxymethyl, tetrahydropyranyl, trityl, trimethylsilylethoxymethyl, tert-butyldimethylsilyl and acetyl are preferred.

Preferred as the protective group for a carboxyl group are a lower alkyl group such as, for example, methyl, ethyl, propyl, isopropyl and tert-butyl; a lower haloalkyl group such as, for example, 2,2,2-trichloroethyl; a lower alkenyl group such as, for example, 2-propenyl; and an aralkyl group such as, for example, benzyl, p-methoxybenzyl, p-nitrobenzyl, benzhydryl and trityl. In particular, methyl, ethyl, tert-butyl, 2-propenyl, benzyl, p-methoxybenzyl and benzhydryl are preferred.

The reaction of the compound represented by Formula [II] with the compound represented by Formula [III] is carried out usually in an inert solvent which does not exert an adverse effect on the reaction, wherein both of the compound [II] and the compound [III] are used in the same mole or either of them is used in slight excess mole.

Preferred as the above inert solvent are ethers such as, for example, tetrahydrofuran and dioxane; halogenated hydrocarbons such as, for example, methylene chloride and chloroform; and aprotic polar solvents such as, for example, dimethylformamide, N,N-dimethylacetamide and acetonitrile.

Further, the reaction described above is carried out preferably in the presence of a base, and preferred as the above base are organic bases such as, for example, triethylamine, diisopropylethylamine, pyridine, 4-dimethylaminopyridine and lithium diisopropylamide, or inorganic bases such as, for example, sodium hydride, sodium hydroxide, sodium carbonate, potassium carbonate and sodium hydrogencarbonate.

The use amount of the above base is one mole to excess mole, preferably 1 to 2 moles per mole of the compound represented by Formula [II].

The reaction temperature is usually −78 to 150° C., preferably a room temperature to 120° C.

The reaction time is usually 5 minutes to 7 days, preferably 30 minutes to 24 hours.

Usual work-ups are carried out after finishing the reaction, whereby the crude product of the compound represented by Formula [IV] can be obtained. The compound represented by Formula [IV] thus obtained is refined according to a conventional method or without refining, the removal reactions of the protective groups for an amino group, a hydroxyl group and a carboxyl group are carried out, if necessary, by suitably combining them, whereby the compound represented by Formula [I] can be produced.

The removal methods of the protective groups are different depending on the kinds of the protective groups and the stability of the objective compound [I] and carried out, for example, according to a method described in a literature [refer to Protective Groups in Organic Synthesis written by T. W. Greene, John Wiley & Sons Co., Ltd. (1981) (hereinafter referred to as literature P)] or a method in accordance with it, for example, solvolysis using an acid or a base, that is, a method in which 0.01 mole to over excess of an acid, preferably trifluoroacetic acid, formic acid, hydrochloric acid and the like, or equimole to over excess of a base, preferably potassium hydroxide, calcium hydroxide and the like are acted, chemical reduction using a metal hydride complex or catalytic reduction using a palladium-carbon catalyst and a Raney nickel catalyst.

Production Process 2

The compound represented by Formula [II]:

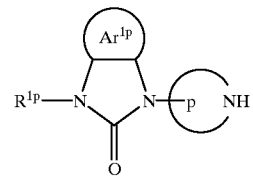

[II]

[wherein

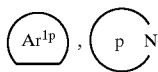

and $R^{1p}$ are synonymous with those described above] is react with a compound represented by Formula [V]:

$$OHC—Cy^p \quad [1]$$

[wherein $Cy^p$ is synonymous with that described above] to prepare a compound represented by Formula [VI]:

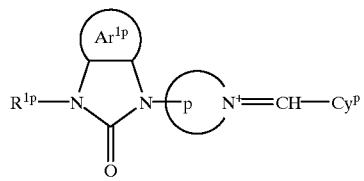

[VI]

[wherein

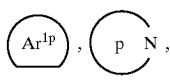

$Cy^p$ and $R^{1p}$ are synonymous with those described above], and then the protective groups are removed if necessary, after reducing the compound [VI], whereby the compound represented by Formula [I-1] can be obtained:

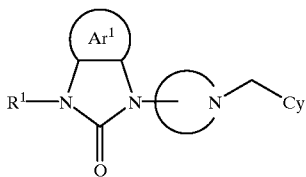

[wherein

Cy and $R^1$ are synonymous with those described above].

The production process 2 is a process for producing the compound in which $R^2$ in the formula is a hydrogen atom among the compounds of the present invention represented by Formula [I], that is, the compound represented by Formula [I-1].

The reaction of the compound represented by Formula [II] with the compound represented by Formula M is carried out usually using both in the same mole or either of them in slight excess mole.

The reaction is carried out usually in an inert solvent, and the above inert solvent includes alcohols such as, for example, methanol, ethanol and propanol; ethers such as, for example, ethyl ether, tetrahydrofuran and dioxane; halogenated hydrocarbons such as, for example, methylene chloride, chloroform and dichloroethane; aromatic hydrocarbons such as, for example, benzene, toluene, chlorobenzene and xylene; aprotic polar solvents such as, for example, dimethylformamide, ethyl acetate, acetonitrile and hexamethyl-phosphoric triamide; or mixed solvents thereof.

The reaction temperature is usually 0° C. to the boiling point of the solvent used for the reaction, preferably a room temperature to 100° C.

The reaction time is usually 5 minutes to 48 hours, preferably 10 minutes to 24 hours.

After finishing the reaction described above, the reaction solution is used for a reduction reaction in the subsequent step as it is or subjected to distillation, or separated from the compound represented by Formula [VI] is isolated using a conventional separating methods and can be subjected to the subsequent reduction reaction.

The above reduction reaction can be carried out by using a metal hydride complex such as, for example, lithium borohydride, sodium borohydride, sodium cyanoborohydride, sodium triacetoxyborohydride and lithium aluminumhydride, or by catalytic reduction using a palladium-carbon catalyst and a Raney nickel catalyst.

In particular, when used is a reducing agent which reduces preferentially imine, such as sodium cyanoborohydride and sodium triacetoxyborohydride, the compound represented by Formula [VI] can be subjected to reduction reaction as it is without isolating.

When a metal hydride complex is used as the reducing agent, the use amount of the reducing agent is usually 1 mole to excess mole, preferably 1 to 5 moles per mole of the imine described above.

In the above reduction reaction, depending on the kind of the reducing agent, there can suitably used as a solvent, inert solvents including alcohols such as, for example, methanol and ethanol; ethers such as, for example, dimethyl ether, ethyl ether, diisopropyl ether, dibutyl ether, dimethoxyethane, dioxane, tetrahydrofuran and diglyme; halogenated hydrocarbons such as, for example, methylene chloride, chloroform and dichloroethane; aliphatic hydrocarbons such as, for example, pentane, hexane, heptane and cyclohexane; and aromatic hydrocarbons such as, for example, benzene and toluene, or mixed solvents thereof.

The reaction temperature is usually -20 to 100° C., preferably 0° C. to a room temperature.

The reaction time is usually 5 minutes to 7 days, preferably 1 to 6 hours.

Usually, the hydrogen pressure in the catalytic reduction reaction is preferably an atmospheric pressure to 5 atm. The use amount of the catalyst is usually 1/100 time to once, preferably 1/100 to 1/10 time as much amount as the weight of the compound [VI] which is the starting material.

After finishing the reaction, usual work-up are carried out after removing the protective groups when they are present in the resulting product or as it is when the protective groups are not present in the resulting product, whereby the compound represented by Formula [I-1] can be produced.

The methods described in the preceding production process 1 can be applied as they are to removal of the protective groups and the work-up.

Production Process 3

A compound represented by Formula [VII]:

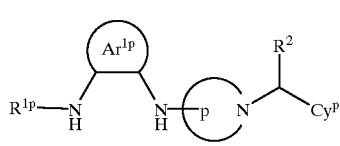

[wherein

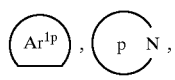

$Cy^p$, $R^{1p}$ and $R^2$ are synonymous with those described above] is reacted with a compound represented by Formula [VIII]:

$X^1$—CO—$X^2$ [VIII]

[wherein $X^1$ and $X^2$ may be the same or different and each represent an imidazolyl group, a methoxy group or an ethoxy group] to prepare the compound represented by Formula [IV]:

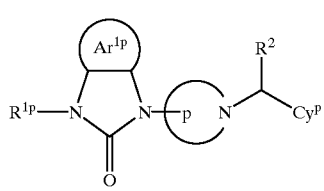

[wherein

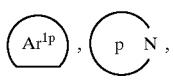

$Cy^p$, $R^{1p}$ and $R^2$ are synonymous with those described above], and the protective groups are removed if necessary, whereby the compound represented by Formula [I] can be obtained.

The reaction of the compound represented by Formula [VII] with the compound represented by Formula [VIII] is carried out usually using 1 mole to excess mole, preferably 1 to 2 moles of the compound represented by Formula [VIII] per mole of the compound represented by Formula [VII].

The reaction is carried out usually in an inert solvent, and suitable as the above inert solvent are, for example, methylene chloride, chloroform, tetrahydrofuran, ethyl ether, benzene, toluene and dimethylformamide, or mixed solvents thereof The reaction temperature is usually −78 to 100° C., preferably a room temperature to 80° C.

The reaction time is usually 5 minutes to 7 days, preferably 30 minutes to 24 hours.

Further, the reaction described above can be carried out in the presence of a base as the case required, and preferred as the above base are organic bases such as, for example, triethylamine, diisopropylethylamine, pyridine, 4-dimethylaminopyridine and lithium diisopropylamide, or inorganic bases such as, for example, sodium hydride, sodium hydroxide, sodium carbonate, potassium carbonate and sodium hydrogencarbonate.

The use amount of the above base is 2 moles to excess moles, preferably 2 to 3 moles per mole of the compound represented by Formula [VII].

After finishing the reaction, usual work-ups are carried out after removing the protective groups when they are present in the resulting product or as it is when the protective groups are not present in the resulting product, whereby the compound represented by Formula [I] can be produced.

The methods described in the preceding production process 1 can be applied as they are to removal of the protective groups and the work-up.

Production Process 4

A compound represented by Formula [IX]:

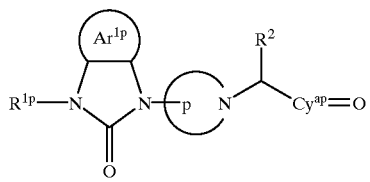

[IX]

[wherein $Cy^{ap}$ represents a mono-, bi- or tricyclic aliphatic carbocyclic group having 3 to 20 carbon atoms, which may have a substituent selected from the group consisting of a halogen atom, a lower alkenyl group, a lower alkynyl group, a di(lower alkyl)amino group, a lower alkoxy group and a group represented by —$R^4$, and an amino group and a lower alkylamino group, which may be protected; and

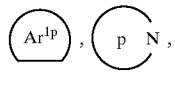

$R^{1p}$, $R^2$ and $R^4$ are synonymous with those described above] is reacted with a compound represented by Formula [X]:

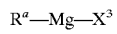

$R^a$—Mg—$X^3$       [XI]

[wherein Ra represents a lower alkyl group; and $X^3$ represents a halogen atom] or a compound represented by Formula [XI]:

$R^a$—Li       [XI]

[wherein $R^a$ is synonymous with that described above] to prepare a compound represented by Formula [XII]:

[XII]

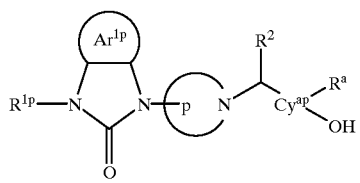

[wherein

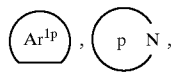

$Cy^{ap}$, $R^a$, $R^{1p}$ and $R^2$ are synonymous with those described above]. Then, the above compound [XII] is subjected to dehydration reaction to thereby prepare a compound represented by Formula [IV-2]:

[IV-2]

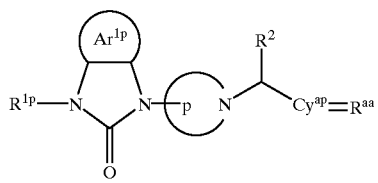

[wherein $R^{aa}$ represents a lower alkylidene group obtained by converting a carbon atom of $R^a$ bonded to $Cy^{ap}$ to a divalent group; and

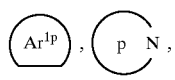

$Cy^p$, $R^{1p}$ and $R^2$ are synonymous with those described above], or a compound represented by Formula [IV-3]:

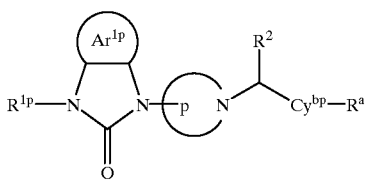

[IV-3]

[wherein $Cy^{bp}$ represents a mono-, bi- or tricyclic aliphatic carbocyclic group having 3 to 20 carbon atoms, which may have a substituent selected from the group consisting of a halogen atom, a lower alkenyl group, a lower alkynyl group, a di(lower alkyl)amino group, a lower alkoxy group and a group represented by —$R^4$, and an amino group and a lower alkylamino group, which may be protected, wherein a ring carbon atom to which $R^a$ is bonded forms a double bond with either of ring carbon atoms adjacent to the above carbon atom; and

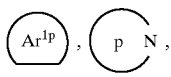

$R^a$, $R^{1p}$, $R^2$ and $R^4$ are synonymous with those described above], and the protective groups are removed if necessary, whereby there can be obtained, a compound represented by Formula [I-2]:

[I-2]

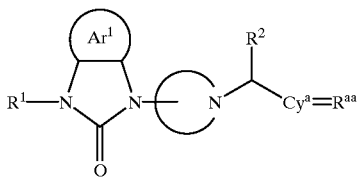

[wherein $Cy^a$ represents a mono-, bi- or tricyclic aliphatic carbocyclic group having 3 to 20 carbon atoms, which may have a substituent selected from the group consisting of a halogen atom, a lower alkenyl group, a lower alkynyl group, an amino group, a lower alkylamino group, a di(lower alkyl)amino group, a lower alkoxy group and a group represented by —$R^4$; and

$R^{aa}$, $R^1$, $R^2$ and $R^4$ are synonymous with those described above], or a compound represented by Formula [I-3]:

[I-3]

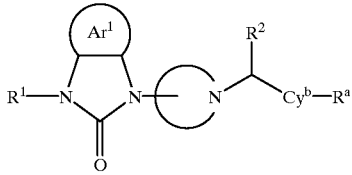

[wherein $Cy^b$ represents a mono-, bi- or tricyclic aliphatic carbocyclic group having 3 to 20 carbon atoms, which may have a substituent selected from the group consisting of a halogen atom, a lower alkenyl group, a lower alkynyl group, an amino group, a lower alkylamino group, a di(lower alkyl)amino group, a lower alkoxy group and a group represented by —$R^4$, wherein a ring carbon atom to which $R^a$ is bonded forms a double bond with ether of ring carbon atoms adjacent to the above carbon atom; and

$R^a$, $R^1$, $R^2$ and $R^4$ are synonymous with those described above].

The production process 4 is a process for producing the compound having a lower alkylidene group as a substituent on Cy in the formula or the compound having at least one double bond on Cy in the formula among the compounds of the present invention represented by Formula [I], that is, the compound represented by Formula [I-2] or the compound represented by Formula [I-3].

The reaction of the compound represented by Formula [IX] with the compound represented by Formula [X] or the compound represented by Formula [XI] is carried out usually using both in the same mole or either of them in slight excess mole. The reaction is carried out in an inert solvent which does not exert an adverse effect on the reaction.

Preferred as the above inert solvent are ethers such as, for example, ethyl ether, tetrahydrofuran and dioxane.

The reaction temperature is usually −100° C. to the boiling point of the solvent used for the reaction, preferably −70 to 50° C.

The reaction time is usually 5 minutes to 7 days, preferably 10 minutes to 24 hours.

The dehydration reaction of the compound [XII] can be carried out, for example, by reacting the compound [XII] with methanesulfonyl chloride in an inert solvent such as ethyl acetate in the presence of triethylamine to prepare corresponding mesylate and then reacting therewith a base such as triethylamine, 1,8-diazabicyclo[5.4.0]-7-undecene, sodium methoxide, sodium ethoxide and potassium tert-butoxide in an inert solvent such as tetrahydrofuran, methanol and ethanol.

After finishing the reaction, usual work-ups are carried out after removing the protective groups when they are present in the resulting product or as it is when the protective groups are not present in the resulting product, whereby the compound represented by Formula [I-2] or the compound represented by Formula [I-3] can be produced.

The methods described in the preceding production process 1 can be applied as they are to removal of the protective groups and the work-up.

Production Process 5

The compound represented by Formula [IV-2]:

[IV-2]

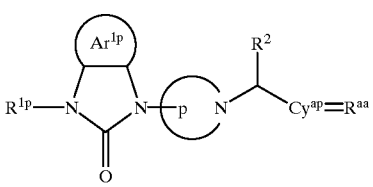

[wherein

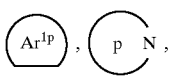

$Cy^{ap}$, $R^{aa}$, $R^{1p}$ and $R^2$ are synonymous with those described above] or the compound represented by Formula [IV-3]:

[IV-3]

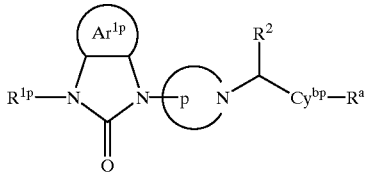

[wherein

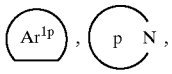

$Cy^{bp}$, $R^a$, $R^{1p}$ and $R^2$ are synonymous with those described above] is reduced to prepare a compound represented by Formula [IV-4]:

[IV-4]

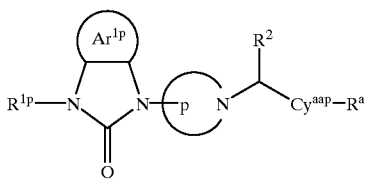

[wherein $Cy^{aap}$ represents a mono-, bi- or tricyclic aliphatic carbocyclic group having 3 to 20 carbon atoms, which may have a substituent selected from the group consisting of a halogen atom, a di(lower alkyl)amino group, a lower alkoxy group and a group represented by —$R^4$, and an amino group and a lower alkylamino group, which may be protected; and

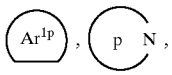

$R^a$, $R^{1p}$, $R^2$ and $R^4$ are synonymous with those described above], and the protective groups are removed if necessary, whereby there can be obtained, a compound represented by Formula [I-4]:

[I-4]

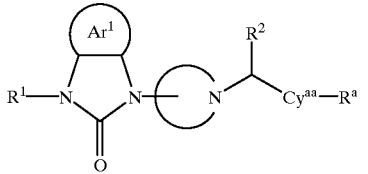

[wherein $Cy^{aa}$ represents a mono-, bi- or tricyclic aliphatic carbocyclic group having 3 to 20 carbon atoms, which may have a substituent selected from the group consisting of a halogen atom, an amino group, a lower alkylamino group, a di(lower alkyl)amino group, a lower alkoxy group and a group represented by —$R^4$; and

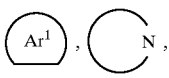

$R^a$, $R^1$, $R^2$ and $R^4$ are synonymous with those described above].

The production process 5 is a process for producing the compound having at least one lower alkyl group as a substituent on Cy in the formula among the compounds of the present invention represented by Formula [I], that is, the compound represented by Formula [I-4].

The reaction to reduce the compound represented by Formula [IV-2] or reduce the compound represented by Formula [IV-3] can be carried out usually in an inert solvent by catalytic reduction using a palladium-carbon catalyst, a Raney nickel catalyst or a platinum catalyst.

The above inert solvent includes, for example, alcohols such as methanol, ethanol and propanol, tetrahydrofuran, chloroform, acetic acid, or mixed solvents thereof.

The reaction temperature is usually –20 to 100° C., preferably 0° C. to a room temperature.

The reaction time is usually 5 minutes to 7 days, preferably 10 minutes to 24 hours.

Usually, the hydrogen pressure in the catalytic reduction reaction is preferably an atmospheric pressure to 5 atm. The use amount of the catalyst is usually 0.01 to 1 g, preferably 0.05 to 0.2 g per g of the compound [IV-2] or the compound [IV-3] which is the starting material.

After finishing the reaction, usual work-ups are carried out after removing the protective groups when they are present in the resulting product or as it is when the protective groups are not present in the resulting product, whereby the compound represented by Formula [I-4] can be produced.

The methods described in the preceding production process 1 can be applied as they are to removal of the protective groups and the work-up.

Production Process 6

A compound represented by Formula [IV-5]:

[IV-5]

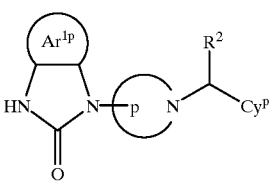

[wherein

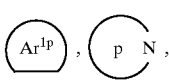

$Cy^p$ and $R^2$ are synonymous with those described above] is reacted with a compound represented by Formula [XIII]:

$R^{1ap}$—$L^2$ [XIII]

[wherein $R^{1ap}$ represents a lower alkenyl group, a lower alkynyl group, a cyclo(lower alkyl) group, a lower alkoxycarbonyl group or a di(lower alkyl)carbamoyl group, or a carboxyl group, a carbamoyl group or a lower alkylcarbamoyl group, which may be protected, or a lower alkyl group which may have a substituent selected from the group consisting of a halogen atom, a cyclo(lower alkyl) group, a di(lower alkyl)amino group, a lower alkoxy group, a di(lower alkyl)carbamoyloxy group, a lower alkoxycarbonyl group, a di(lower alkyl)carbamoyl group and a group represented by —Ar$^{2p}$, and an amino group, a lower alkylamino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a carboxyl group, a carbamoyl group and a lower alkylcarbamoyl group, which may be protected; L$^2$ represents a leaving group; and Ar$^{2p}$ is synonymous with that described above] to prepare a compound represented by Formula [IV-6]:

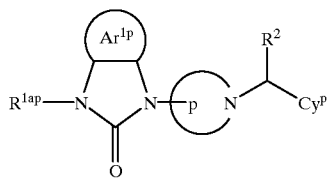

[IV-6]

[wherein

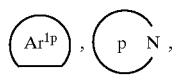

Cy$^p$, R$^{1ap}$ and R$^2$ are synonymous with those described above], and the protective groups are removed if necessary, whereby there can be obtained, a compound represented by Formula [I-5]:

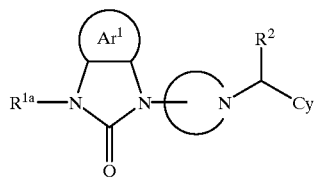

[I-5]

[wherein R$^{1a}$ represents a lower alkenyl group, a lower alkynyl group, a cyclo(lower alkyl) group, a carboxyl group, a lower alkoxycarbonyl group, a carbamoyl group, a lower alkylcarbamoyl group or a di(lower alkyl)carbamoyl group, or a lower alkyl group which may have a substituent selected from the group consisting of a halogen atom, a cyclo(lower alkyl) group, an amino group, a lower alkylamino group, a di(lower alkyl)amino group, a (lower alkyl)sulfonylamino group, an aminosulfonylamino group, a (lower alkylamino) sulfonylamino group, a (di-lower alkylamino)sulfonylamino group, a carbamoylamino group, a (lower alkylcarbamoyl) amino group, a (di-lower alkylcarbamoyl)amino group, a hydroxyl group, a lower alkoxy group, a carbamoyloxy group, a lower alkylcarbamoyloxy group, a di(lower alkyl) carbamoyloxy group, a carboxyl group, a lower alkoxycarbonyl group, a carbamoyl group, a lower alkylcarbamoyl group, a di(lower alkyl)carbamoyl group and a group represented by —Ar$^2$; and

Ar$^2$, Cy and R$^2$ are synonymous with those described above].

The production process 6 is a process for producing, among the compounds of the present invention represented by Formula [I], the compound in which R in the formula represents a lower alkenyl group, a lower alkynyl group, a cyclo(lower alkyl) group, a carboxyl group, a lower alkoxycarbonyl group, a carbamoyl group, a lower alkylcarbamoyl group or a di(lower alkyl)carbamoyl group, or a lower alkyl group which may have a substituent selected from the group consisting of a halogen atom, a cyclo(lower alkyl) group, an amino group, a lower alkylamino group, a di(lower alkyl) amino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group and a group represented by —Ar$^2$, that is, the compound represented by Formula [I-5].

The same leaving group as given for L$^1$ can be given for the leaving group represented by L$^2$.

The reaction of the compound represented by Formula [IV-5] with the compound represented by Formula [XIII] can be carried out according to the reaction of the compound represented by Formula [II] with the compound represented by Formula [III] in the production process 1 described above.

After finishing the reaction, usual work-ups are carried out after removing the protective groups when they are present in the resulting product or as it is when the protective groups are not present in the resulting product, whereby the compound represented by Formula [I-5] can be produced.

The methods described in the preceding production process 1 can be applied as they are to removal of the protective groups and the work-up.

Production Process 7

A compound represented by Formula [XIV]:

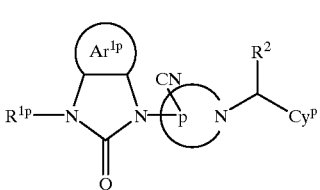

[XIV]

[wherein

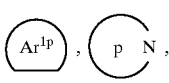

Cy$^p$, R$^{1p}$ and R$^2$ are synonymous with those described above] is hydrolyzed to prepare a compound represented by Formula [IV-7]:

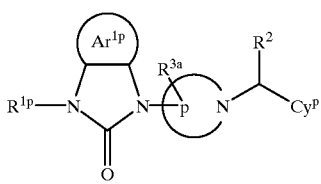

[IV-7]

[wherein $R^{3a}$ represents a carbamoyl group or a carboxyl group, and

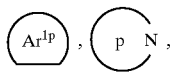

$Cy^p$, $R^{1p}$ and $R^2$ are synonymous with those described above], and when $R^{3a}$ is a carboxyl group, the above carboxyl group is converted, if necessary, to a lower alkoxycarbonyl group. Then, the protective groups are removed if necessary, whereby there can be obtained, a compound represented by Formula [I-6]:

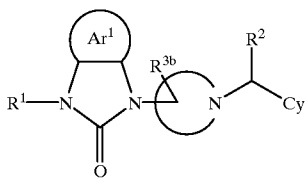

[I-6]

[wherein $R^{3a}$ represents a carbamoyl group, a carboxyl group or a lower alkoxycarbonyl group, and

Cy, $R^1$ and $R^2$ are synonymous with those described above].

The production process 7 is a process for producing, among the compounds of the present invention represented by Formula [I], the compound having a carbamoyl group, a carboxyl group or a lower alkoxycarbonyl group as a substituent on the same ring carbon atom to which a group represented by

and a group represented by

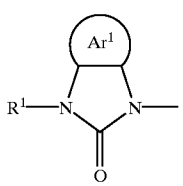

are bonded, that is, the compound represented by Formula [I-6].

The hydrolysis reaction of the compound represented by Formula [XIV] can usually be carried out by reacting the above compound with the excess amount of an acid such as, for example, hydrochloric acid and sulfuric acid or a base such as, for example, sodium hydroxide and potassium hydroxide in a solvent such as, for example, water, methanol hydrate, ethanol hydrate and dioxane hydrate.

The reaction temperature is usually a room temperature to the boiling point of the solvent used for the reaction, preferably 50° C. to the boiling point of the solvent used for the reaction.

The reaction time is usually 10 minutes to 24 hours, preferably 30 minutes to 8 hours when the compound in which $R^{3a}$ is a carbamoyl group is produced and usually one hour to 7 days, preferably 8 hours to 3 days when the compound in which $R^{3a}$ is a carboxyl group is produced.

After finishing the reaction, usual work-ups are carried out after removing the protective groups when they are present in the resulting product or as it is when the protective groups are not present in the resulting product, or when $R^{3a}$ is a carboxyl group, the above carboxyl group is converted to a lower alkoxycarbonyl group by a method which is well known in the field of organic chemistry, and then the same treatment as described above is carried out, whereby the compound represented by Formula [I-6] can be produced.

The methods described in the preceding production process 1 can be applied as they are to removal of the protective groups and the work-up.

Production Process 8

The compound represented by Formula [II]:

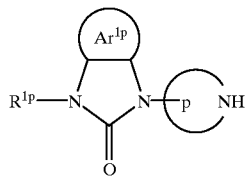

[II]

[wherein

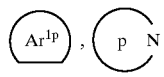

and $R^{1p}$ are synonymous with those described above] is reacted with carboxylic acid represented by Formula [XV]:

HOOC—$Cy^p$ [XV]

[wherein $Cy^p$ is synonymous with that described above] or a reactive derivative thereof to prepare a compound represented by Formula [XVI]:

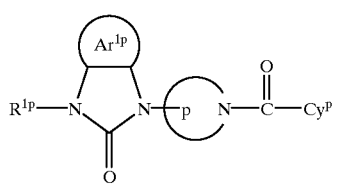

[XVI]

[wherein

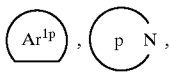

$Cy^p$ and $R^{1p}$ are synonymous with those described above], and after reducing the compound [XVI], the protective groups are removed if necessary, whereby there can be obtained, the compound represented by Formula [I-1]:

[I-1]

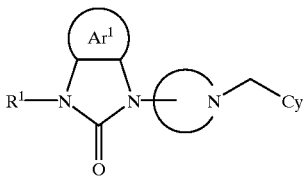

[wherein

Cy and $R^1$ are synonymous with those described above].

The production process 8 is a process for producing the compound in which $R^2$ in the formula is a hydrogen atom among the compounds of the present invention represented by Formula [I], that is, the compound represented by Formula [I-1].

Acid halides, mixed acid anhydrides, activated esters and activated amides are used as the reactive derivative of the carboxylic acid represented by Formula [XV].

When the carboxylic acid represented by Formula [XV] is used, the reaction is carried out preferably in the presence of a condensing agent such as N,N'-dicyclohexylcarbodimide, 1-ethyl-3-(3-dimethylaminopropyl)carbodimide and 2-chloro-1,3-dimethylimidazolyl chloride.

The reaction of the compound represented by Formula [II] with the carboxylic acid represented by Formula [XV] or the reactive derivative thereof is carried out in one mole to excess mole, preferably 1 to 5 moles of the carboxylic acid represented by Formula [XV] or the reactive derivative thereof per mole of the compound represented by Formula [II].

The reaction is carried out usually in an inert solvent, and the above inert solvent includes halogenated hydrocarbons such as, for example, methylene chloride, chloroform, carbon tetrachloride, dichloroethane and trichloroethylene; ethers such as, for example, ethyl ether, tetrahydrofuran and dioxane; aromatic hydrocarbons such as, for example, benzene, toluene, chlorobenzene and xylene; aprotic polar solvents such as, for example, dimethylformamide, acetonitrile, acetone, ethyl acetate and hexamethylphosphoric triamide; or mixed solvents thereof.

The reaction temperature is usually −70° C. to the boiling point of the solvent used for the reaction, preferably −20 to 100° C.

The reaction time is usually 5 minutes to 7 days, preferably 10 minutes to 24 hours.

Further, the reaction described above can be carried out in the presence of a base in order to allow the reaction to go on smoothly.

The above base includes inorganic bases such as, for example, sodium hydroxide, potassium hydroxide, calcium hydroxide, sodium carbonate, potassium carbonate and sodium hydrogencarbonate, or organic bases such as, for example, triethylamine, N-ethyldiisopropylamine, pyridine, 4-dimethylaminopyridine and N,N-dimethylaniline.

The use amount of the above base is one mole to excess moles, preferably 1 to 5 moles per mole of the reactive derivative of the carboxylic acid represented by Formula [XV].

The acid halide of the compound represented by Formula [XV] can be obtained by reacting the carboxylic acid represented by Formula [XV] with a halogenating agent according to a conventional method. Used as the halogenating agent are, for example, thionyl chloride, phosphorus trichloride, phosphorus pentachloride, phosphorus oxychloride, phosphorus tribromide, oxalyl chloride and phosgene.

The mixed acid anhydride of the compound represented by Formula [XV] can be obtained by reacting the carboxylic acid represented by Formula [XV] with alkyl chlorocarbonate such as ethyl chlorocarbonate and aliphatic carboxylic chloride such as acetyl chloride according to a conventional method.

The activated ester of the compound represented by Formula [XV] can be obtained by reacting the carboxylic acid represented by Formula [XV] with an N-hydroxy compound such as, for example, N-hydroxysuccinimide, N-hydroxyphthalimide and 1-hydroxybenzotriazole and a phenol compound such as, for example, 4-nitrophenol, 2,4-dinitrophenol, 2,4,5-trifluorophenol and pentafluorophenol in the presence of a condensing agent such as, for example, N,N'-dicyclohexylcarbodimide and 1-ethyl-3-(3-dimethylaminopropyl)carbodimide according to a conventional method.

The activated amide of the compound represented by Formula [XV] can be obtained by reacting the carboxylic acid represented by Formula [XV] with, for example, 1,1'-carbonyldiimidazole and 1,1'-carbonylbis(2-methylimidazole) according to a conventional method.

After finishing the reaction described above, the reaction solution is used for a reduction reaction in the subsequent step as it is or subjected to distillation, or separated from the compound represented by Formula [XVI] using a conventional separating methods and can be subjected to the subsequent reduction reaction.

The above reduction reaction can be carried out using a metal hydride complex such as, for example, lithium borohydride, sodium borohydride, lithium aluminum hydride, a borane-triethylamine complex, a borane-dimethyl sulfide complex and a borane-dimethylamine complex as a reducing agent.

The use amount of the reducing agent is usually one mole to excess moles, preferably 1 to 5 moles per mole of the compound represented by Formula [XVI].

In the above reduction reaction, depending on the kind of the reducing agent, there can suitably used as a solvent, inert solvents including alcohols such as, for example, methanol and ethanol; ethers such as, for example, dimethyl ether, ethyl ether, diisopropyl ether, dibutyl ether, dimethoxyethane, dioxane, tetrahydrofuran and diglyme; halogenated hydrocarbons such as, for example, methylene chloride, chloroform and dichloroethane; aliphatic hydrocarbons such as, for example, pentane, hexane, heptane and cyclohexane; and aromatic hydrocarbons such as, for example, benzene and toluene, or mixed solvents thereof.

The reaction temperature is usually 0 to 100° C., preferably a room temperature to 80° C.

The reaction time is usually 10 minutes to 2 days, preferably 30 minutes to 8 hours.

After finishing the reaction, usual work-ups are carried out after removing the protective groups when they are present in the resulting product or as it is when the protective groups are not present in the resulting product, whereby the compound represented by Formula [I-1] can be produced.

The methods described in the preceding production process 1 can be applied as they are to removal of the protective groups and the work-up.

Production Process 9

A compound represented by Formula [XVII]:

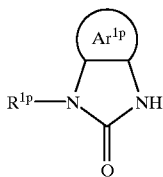

[XVII]

[wherein

and $R^{1p}$ are synonymous with those described above] is reacted with a compound represented by Formula [XVIII]:

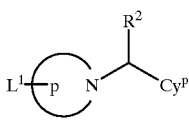

[XVIII]

[wherein

$Cy^p$, $L^1$ and $R^2$ are synonymous with those described above] to prepare the compound represented by Formula [IV]:

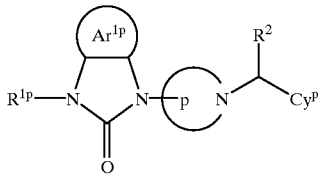

[IV]

[wherein

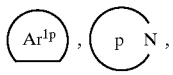

$Cy^p$, $R^{1p}$ and $R^2$ are synonymous with those described above], and the protective groups are removed if necessary, whereby the compound represented by Formula [I] can be obtained.

The reaction of the compound represented by Formula [XVII] with the compound represented by Formula [XIII] can be carried out according to the reaction of the compound represented by Formula [II] with the compound represented by Formula [III] in the production process 1 described above.

After finishing the reaction, usual work-ups are carried out after removing the protective groups when they are present in the resulting product or as it is when the protective groups are not present in the resulting product, whereby the compound represented by Formula [I] can be produced.

The methods described in the preceding production process 1 can be applied as they are to removal of the protective groups and the work-up.

Production Process 10

A compound represented by Formula [IV-8]:

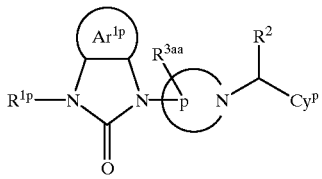

[IV-8]

[wherein $R^{3aa}$ represents a lower alkoxycarbonyl group or a lower alkyl group having a lower alkoxycarbonyl group, and

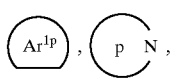

$Cy^p$, $R^{1p}$ and $R^2$ are synonymous with those described above] red to prepare a compound represented by Formula [IV-9]:

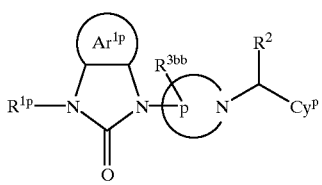

[IV-9]

[wherein $R^{3bb}$ represents a hydroxymethyl group or a lower alkyl group having a hydroxymethyl group, and

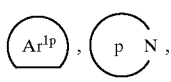

$Cy^p$, $R^{1p}$ and $R^2$ are synonymous with those described above], and the protective groups are removed if necessary, whereby there can be obtained, a compound represented by Formula [I-7]:

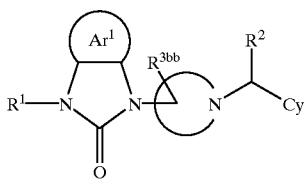

[I-7]

[wherein

Cy, $R^1$, $R^2$ and $R^{3bb}$ are synonymous with those described above].

The production process 10 is a process in which at least one lower alkoxycarbonyl group or lower alkyl group having a lower alkoxycarbonyl group which is present on a group represented by

is reduced to convert the above group to a hydroxymethyl group or a lower alkyl group having a hydroxymethyl group, that is, a process for producing the compound represented by Formula [I-7] among the compound of the present invention represented by Formula [I].

The above reduction reaction of the compound represented by Formula [IV-8] can be carried out using as a reducing agent, a metal hydride complex such as, for example, lithium borohydride, sodium borohydride, lithium triethylborohydride, lithium tri(sec-butyl)borohydride, potassium tri(sec-butyl)borohydride, lithium aluminum hydride, diisobutyl aluminum hydride and a borane-dimethyl sulfide complex, preferably lithium borohydride, lithium aluminum hydride and diisobutyl aluminum hydride.

The use amount of the reducing agent is usually 1 to 10 moles, preferably 1 to 3 moles per mole of the compound represented by Formula [IV-8].

In the above reduction reaction, depending on the kind of the reducing agent, there can suitably used as a solvent, inert solvents including alcohols such as, for example, methanol and ethanol; ethers such as, for example, dimethyl ether, ethyl ether, diisopropyl ether, dibutyl ether, dimethoxyethane, dioxane, tetrahydrofuran and diglyme; halogenated hydrocarbons such as, for example, methylene chloride, chloroform and dichloroethane; aliphatic hydrocarbons such as, for example, pentane, hexane, heptane and cyclohexane; and aromatic hydrocarbons such as, for example, benzene and toluene, or mixed solvents thereof.

The reaction temperature is usually —78° C. to the boiling point of the solvent used for the reaction, preferably —78° C. to a room temperature.

The reaction time is usually 10 minutes to 24 hours, preferably 30 minutes to 2 hours.

After finishing the reaction, usual work-ups are carried out after removing the protective groups when they are present in the resulting product or as it is when the protective groups are not present in the resulting product, whereby the compound represented by Formula [I-7] can be produced.

The methods described in the preceding production process 1 can be applied as they are to removal of the protective groups and the work-up.

Isolation and refining of the compound represented by Formula [I], [I-2], [I-3], [I-4], [I-5], [I-6] or [I-7] obtained by the method described above are achieved by carrying out conventional separating methods such as, for example, column chromatography using silica gel and adsorbing resins, liquid chromatography, solvent extraction or recrystallization/reprecipitation alone or suitably combining them.

The compound represented by Formula [I], [I-2], [I-3], [I-4], [I-5], [I-6] or [I-7] can be converted to pharmaceutically acceptable salt or ester according to a conventional method, or inversely, the salt or ester can be converted to the free compound according to a conventional method.

Commercial products can be used for the compound represented by Formula [II], [III], [V], [VII], [VIII], [IX], [X], [XI], [XIII], [XIV], [XV], [II] or [XVIII], or they can be produced by methods described in literatures [refer to International Publication WO96/13262 gazette; J. Org. Chem., vol. 33, p. 2157 (1968); ibid, vol. 43, p. 147 (1978); and Organic Reactions, p. 405 (1975)] or method according to them, or the following methods or methods described in the reference examples.

Production process A

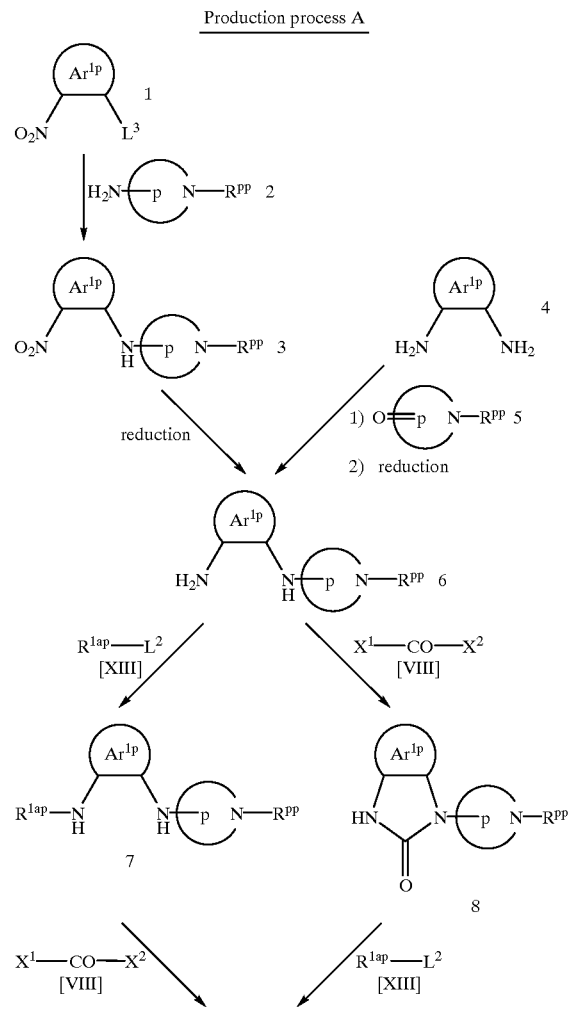

-continued

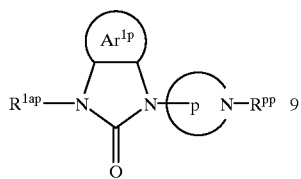

[wherein $L^3$ represents a leaving group; $R^{pp}$ represents a protective group for an amino group; and

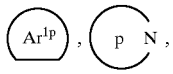

$L^2$, $R^{1ap}$, $X^1$ and $X^2$ are synonymous with those described above].

The present production process is a process for producing a compound represented by Formula 8 or 9. According to the present production process, a compound represented by Formula 1 is reacted with a compound represented by Formula 2 to prepare a compound represented by Formula 3, and then the nitro group of the compound 3 is reduced, whereby a compound represented by Formula 6 is produced. Subsequently, (1) the above compound 6 is reacted with the compound represented by Formula [XIII] to prepare a compound represented by Formula 7, and then the above compound 7 is reacted with the compound represented by Formula [VIII], whereby a compound represented by Formula 9 is produced, or (2) the above compound 6 is reacted with the compound represented by Formula [VIII] to prepare a compound represented by Formula 8, and then the above compound 8 is reacted with the compound represented by Formula [XIII], whereby the compound represented by Formula 9 can be produced.

The compound represented by Formula 6 can be produced as well by reacting a compound represented by Formula 4 with a compound represented by Formula 5 to form imine and then reducing it.

The leaving group represented by $L^3$ includes, for example, a halogen atom such as a fluorine atom, a chlorine atom, a bromine atom and an iodine atom, an organic sulfonyl group such as methanesulfonyl, ethanesulfonyl and benzenesulfonyl, or an organic sulfonyloxy group such as methanesulfonyloxy, trifluoromethanesulfonyloxy and p-toluenesulfonyloxy.

The protective group for an amino group represented by $R^{pp}$ includes the protective groups for an amino group which are described in the production process 1 described above. Among them, t-butoxycarbonyl and benzyl are preferred.

A step for producing the compound 3 from the compound 1 can be carried out in the same manner as that of the step for reacting the compound represented by Formula [II] with the compound represented by Formula [III] in the production process 1 described above, and therefore the same reaction conditions can be applied.

A step for producing the compound 6 from the compound 3 can be carried out by reacting the compound 3 with iron powder and ammonium chloride in a solvent such as, for example, methanol hydrate, ethanol hydrate and dioxane hydrate.

The reaction temperature is usually a room temperature to the boiling point of the solvent used for the reaction, preferably 50° C. to the boiling point of the solvent used for the reaction.

The reaction time is usually 10 minutes to 24 hours, preferably 30 minutes to 8 hours.

A step for producing the compound 7 from the compound 6 and a step for producing the compound 9 from the compound 8 can be carried out respectively in the same manner as that of the step for reacting the compound represented by Formula [II] with the compound represented by Formula [III] in the production process 1 described above, and therefore the same reaction conditions can be applied.

A step for producing the compound 8 from the compound 6 and a step for producing the compound 9 from the compound 7 can be carried out respectively in the same manner as that of the step for reacting the compound represented by Formula [VII] with the compound represented by Formula [VIII] in the production process 3 described above, and therefore the same reaction conditions can be applied.

A step for producing the compound 6 from the compound 4 can be carried out in the same manner as that of the step for reacting the compound represented by Formula [II] with the compound represented by Formula [V] and then subjecting the resulting compound to reduction reaction in the production process 2 described above, and therefore the same reaction conditions can be applied.

The compound represented by Formula 8 or 9 can be derived to the compound represented by Formula [II] by deblocking the protective group $R^{pp}$ of the above compound.

The above protective group can be deblocked according to the method described in the literature P described above.

Commercial products can be used for the compound represented by Formula 1, 2 or 4, or it can be produced by suitably combining, if necessary, publicly known methods, the methods described in the reference examples or methods according to them.

Production process B

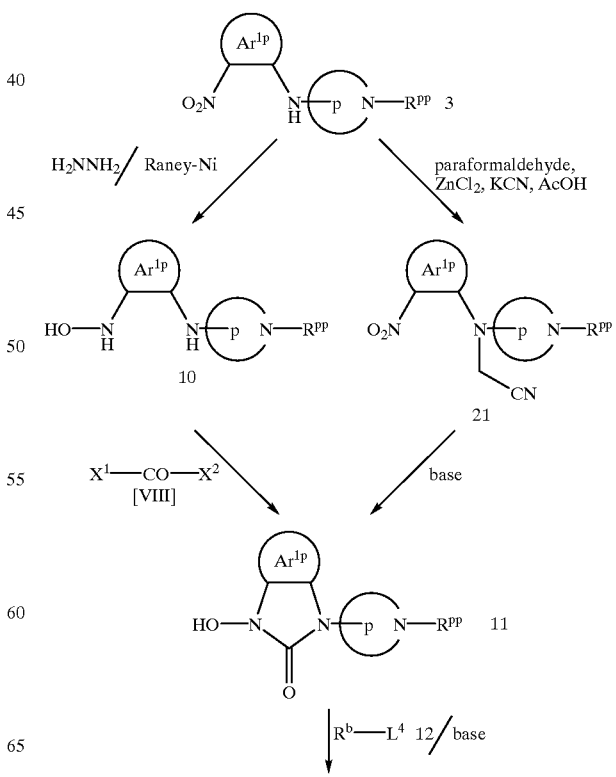

-continued

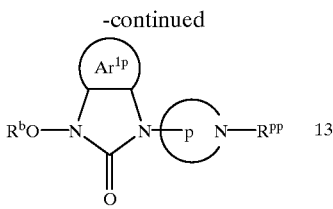

[wherein Ac represents an acetyl group; $L^4$ represents a leaving group; $R^b$ represents a lower alkyl group; and

$R^{pp}$, $X^1$ and $X^2$ are synonymous with those described above].

The present production process is a process for producing a compound represented by Formula 11 or 13. According to the present production process, the nitro group of the compound represented by Formula 3 is reduced by hydrazine in the presence of Raney nickel to prepare a compound represented by Formula 10, and then the above compound 10 is reacted with the compound represented by Formula [VIII], whereby a compound represented by Formula 11 can be produced. Further, the above compound 11 is reacted with a compound represented by Formula 12 in the presence of a base, whereby a compound represented by Formula 13 can be produced.

The compound represented by Formula 11 can be produced as well by reacting the compound represented by Formula 3 with paraformaldehyde and cyanide to prepare a compound represented by Formula 21 and then reacting the above compound 21 with a base.

The leaving group represented by L includes the same leaving groups as those given for L described above.

A step for producing the compound 10 from the compound 3 can be carried out by reacting the compound 3 with hydrazine in a solvent such as, for example, methanol, ethanol, methylene chloride, chloroform or a mixed solvent thereof in the presence of a Raney nickel catalyst.

The use amount of the Raney nickel catalyst is 1/100 time to once, preferably 1/100 to 1/10 time as much amount as the weight of the compound 3, and the use amount of hydrazine is 1 to 10 moles, preferably 2 to 3 moles per mole of the compound 3.

The reaction temperature is usually 0° C. to the boiling point of the solvent used for the reaction, preferably 0° C. to a room temperature.

The reaction time is usually 10 minutes to 24 hours, preferably 30 minutes to 8 hours.

A step for producing the compound 11 from the compound 10 can be carried out in the same manner as that of the step for reacting the compound represented by Formula [VII] with the compound represented by Formula [VIII] in the production process 3 described above, and therefore the same reaction conditions can be applied.

A step for producing the compound 13 from the compound 11 can be carried out in the same manner as that of the step for reacting the compound represented by Formula [II] with the compound represented by Formula [III] in the production process 1 described above, and therefore the same reaction conditions can be applied. Further, it is possible to substitute, for example, a diazo compound such as diazomethane for the compound 12 and alkylate a hydroxyl group of the compound 11 according to a conventional method.

A step for producing the compound 21 from the compound 3 can be carried out by reacting the compound 3 with paraformaldehyde and cyanide such as, for example, potassium cyanide and sodium cyanide in acetic acid, water, methanol, ethanol, dioxane or a mixed solvent thereof in the presence of a Lewis acid such as zinc chloride.

The use amount of the Lewis acid, paraformaldehyde or potassium cyanide is 1 to 10 moles, preferably 2 to 3 moles per mole of the compound 3.

The reaction temperature is usually 0° C. to the boiling point of the solvent used for the reaction, preferably a room temperature to 60° C.

The reaction time is usually 15 minutes to 3 days, preferably 30 minutes to 24 hours.

A step for producing the compound 11 from the compound 21 can be carried out by reacting the compound 21 with a base in, for example, water, methanol, ethanol, dioxane, dimethylformamide or a mixed solvent thereof.

Preferred as the above base are organic bases such as, for example, triethylamine and pyridine or inorganic bases such as, for example, sodium hydride, sodium hydroxide, sodium carbonate and potassium carbonate.

The use amount of the above base is 1 to 10 moles, preferably 2 to 3 moles per mole of the compound 21.

The reaction temperature is usually 0° C. to the boiling point of the solvent used for the reaction, preferably a room temperature to the boiling point of the solvent used for the reaction.

The reaction time is usually 15 minutes to 2 days, preferably 30 minutes to 8 hours.

The compound represented by Formula 11 or 13 can be converted to the compound represented by Formula [II] by deblocking the protective group $R^{pp}$ of the above compound.

The above protective group can be deblocked according to the method described in the literature P described above.

Production process C

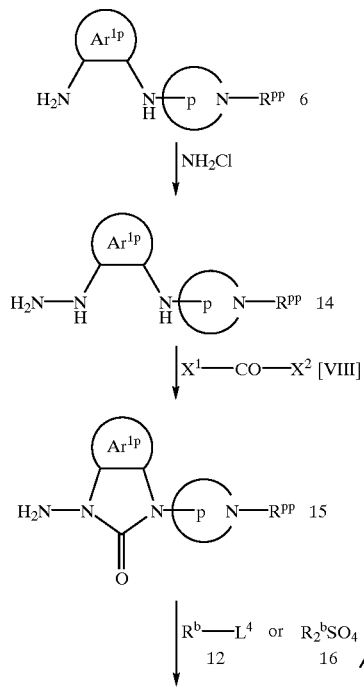

-continued

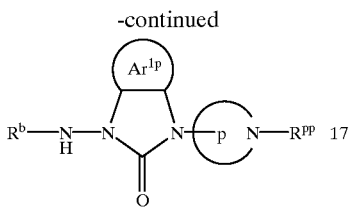

[wherein

$L^4$, $R^b$, $R^{pp}$, $X^1$ and $X^2$ are synonymous with those described above].

The present production process is a process for producing a compound represented by Formula 15 or 17. According to the present production process, the compound represented by Formula 6 is reacted with chloramine to prepare a compound represented by Formula 14, and then the above compound 14 is reacted with the compound represented by Formula [VIII], whereby a compound represented by Formula 15 can be produced. Further, the above compound 15 is reacted with a compound represented by Formula 12 or 16 in the presence of a base, whereby a compound represented by Formula 17 can be produced.

A step for producing the compound 14 from the compound 6 can be carried out by applying a so-called Rasching reaction [refer to Ber., vol. 40, p. 4580 (1907)] in which the compound 3 is reacted with a chloramine aqueous solution in the presence of gelatin.

The use amount of chloramine is 0.1 to 2 moles, preferably 0.2 to 0.8 mole per mole of the compound 6.

The reaction temperature is usually 0° C. to 100° C., preferably a room temperature to 100° C.

The reaction time is usually 10 minutes to 24 hours, preferably 30 minutes to 8 hours.

A step for producing the compound 15 from the compound 14 can be carried out in the same manner as that of the step for reacting the compound represented by Formula [VII] with the compound represented by Formula [VIII] in the production process 3 described above, and therefore the same reaction conditions can be applied.

A step for producing the compound 17 from the compound 15 can be carried out in the same manner as that of the step for reacting the compound represented by Formula [II] with the compound represented by Formula [III] in the production process 1 described above, and therefore the same reaction conditions can be applied.

The compound represented by Formula 15 or 17 can be converted to the compound represented by Formula [II] by deblocking the protective group $R^{pp}$ of the above compound.

The above protective group can be deblocked according to the method described in the literature P described above.

Production process D

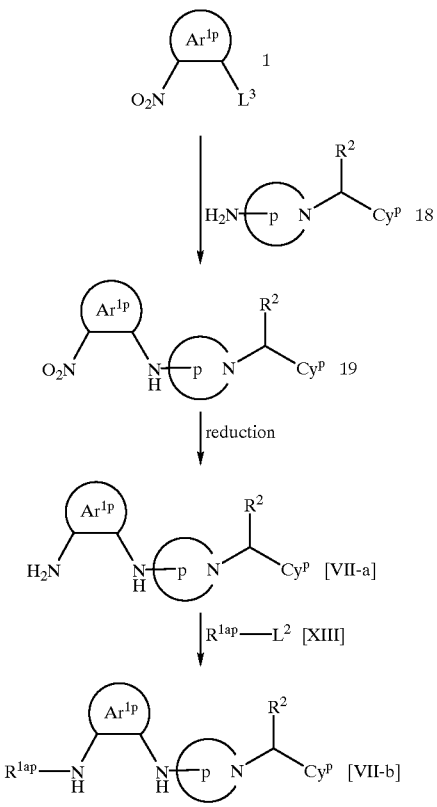

[wherein

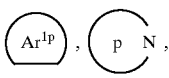

$L^2$, $L^3$, $R^{1ap}$, $R^2$ and $Cy^p$ are synonymous with those described above].

The present production process is a process for producing a compound represented by Formula [VII-a] or [VII-b]. According to the present production process, the compound represented by Formula 1 is reacted with a compound represented by Formula 18 to prepare a compound represented by Formula 19, and then the nitro group of the above compound 19 is reduced, whereby the compound represented by Formula [VII-a] can be produced. Further, the above compound [VII-a] is reacted with the compound represented by Formula [XIII], whereby the compound represented by Formula [VII-b] can be produced.

A step for producing the compound 19 from the compound 1 can be carried out in the same manner as that of the step for reacting the compound represented by Formula [II] with the compound represented by Formula [III] in the production process 1 described above, and therefore the same reaction conditions can be applied.

A step for producing the compound [VII-a] from the compound 19 can be carried out in the same manner as that of the step for producing the compound 6 from the compound 3 in the production process A described above, and therefore the same reaction conditions can be applied.

A step for producing the compound [VII-b] from the compound [VII-a] can be carried out in the same manner as that of the step for reacting the compound represented by Formula [II] with the compound represented by Formula [III] in the production process 1 described above, and therefore the same reaction conditions can be applied.

Commercial products can be used for the compound represented by Formula 18, or it can be produced by suitably combining, if necessary, publicly known methods, the methods described in the reference examples or methods according to them.

Production process E

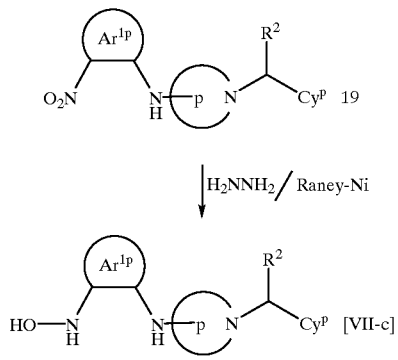

[wherein

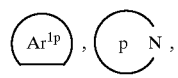

$R^2$ and $Cy^p$ are synonymous with those described above].

The present production process is a process for producing a compound represented by Formula [VII-c]. According to the present production process, the nitro group of the compound represented by Formula 19 is reduced by hydrazine in the presence of Raney nickel, whereby the compound represented by Formula [VII-c] can be produced.

The present step can be carried out in the same manner as that of the step for producing the compound 10 from the compound 3 in the production process B described above, and therefore the same reaction conditions can be applied.

Production process F

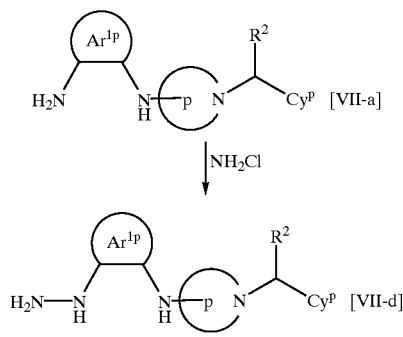

[wherein

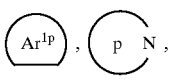

$R^2$ and $Cy^p$ are synonymous with those described above].

The present production process is a process for producing a compound represented by Formula [VII-d]. According to the present production process, the compound represented by Formula [VII-a] is reacted with chloramine, whereby the compound represented by Formula [VII-d] can be produced.

The present step can be carried out in the same manner as that of the step for producing the compound 14 from the compound 6 in the production process C described above, and therefore the same reaction conditions can be applied.

Production process G

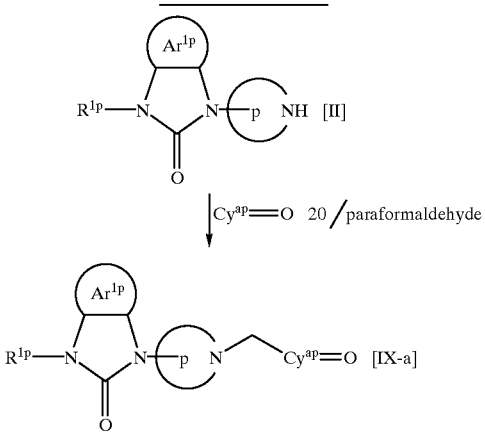

[wherein

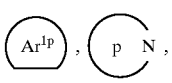

$R^{1p}$ and $Cy^{ap}$ are synonymous with those described above].

The present production process is a process for producing a compound represented by Formula [IX-a]. According to the present production process, the compound represented by Formula [II] is reacted with paraformaldehyde and a compound represented by Formula 20, whereby the compound represented by Formula [IX-a] can be produced.

A so-called Mannich reaction which is well known in the field of organic synthesis chemistry can be applied to the present step, and therefore the general conditions of the Mannich reaction can be applied to the reaction conditions thereof.

The compound [11] is reacted with paraformaldehyde and ketone represented by Formula 20 in a solvent such as, for example, water, methanol, ethanol and dioxane under acidity obtained by adding acetic acid or hydrochloric acid, whereby the compound represented by Formula [IX-a] can be produced.

The use amount of paraformaldehyde is 1 to 10 moles, preferably 1 to 3 moles per mole of the compound [II], and the use amount of ketone represented by Formula 20 is 1 to 10 moles, preferably 1 to 3 moles per mole of the compound [II].

The reaction temperature is usually a room temperature to the boiling point of the solvent used for the reaction, preferably 50° C. to the boiling point of the solvent used for the reaction.

The reaction time is usually 10 minutes to 24 hours, preferably 30 minutes to 8 hours.

Commercial products can be used for the compound represented by Formula , or it can be produced by suitably combining, if necessary, publicly known methods, the methods described in the reference examples or methods according to them.

Production process H

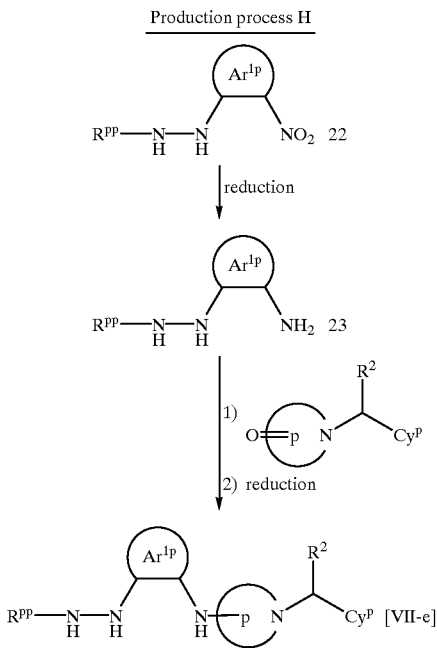

[wherein

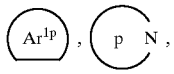

$R^{pp}$, $R^2$ and $Cy^p$ are synonymous with those described above].

The present production process is a process for producing a compound represented by Formula [VII-e]. According to the present production process, the nitro group of a compound represented by Formula 22 is reduced to thereby produce a compound represented by Formula 23, and then the above compound 23 is reacted with a compound represented by 24 to form imine, followed by reducing this, whereby the compound represented by Formula [VII-e] can be produced.

A step for producing the compound 23 from the compound 22 can be carried out in the same manner as that of the step for producing the compound 6 from the compound 3 in the production process A described above, and therefore the same reaction conditions can be applied.

A step for producing the compound represented by Formula [VII-e] from the compound 23 can be carried out in the same manner as that of the step for reacting the compound represented by Formula [II] with the compound represented by Formula [V] and then subjecting the resulting compound to reduction reaction in the production process 2 described above, and therefore the same reaction conditions can be applied.

Commercial products can be used for the compound represented by Formula 22 or 24, or it can be produced by suitably combining, if necessary, publicly known methods, the methods described in the reference examples or methods according to them.

Production process I

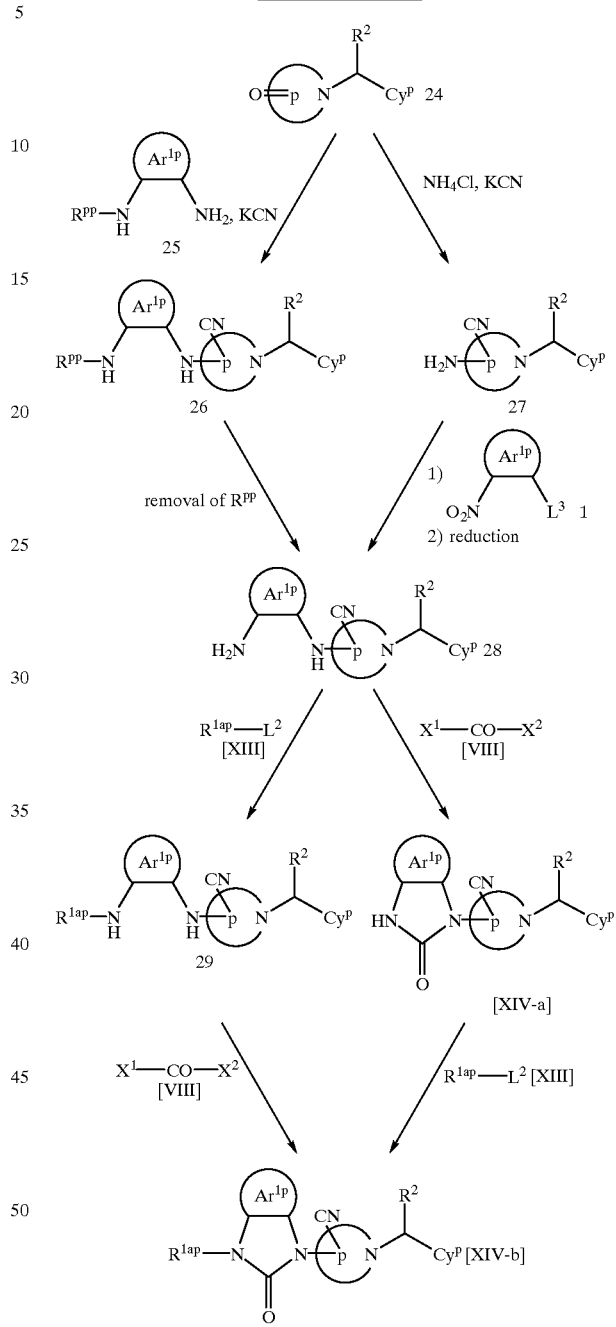

[wherein

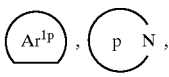

$L^2$, $L^3$, $R^{1ap}$, $R^{pp}$, $R^2$, $Cy^p$ $X^1$ and $X^2$ are synonymous with those described above].

The present production process is a process for producing a compound represented by Formula [XIV-a] or [XIV-b]. According to the present production process, a compound represented by Formula 24 is reacted with a compound represented by Formula 25 and cyanide to prepare a compound represented by Formula 26, and then the protective group $R^{pp}$ of the compound 26 is removed, whereby a compound represented by Formula 28 is produced. Subsequently, (1) the above compound 28 is reacted with the compound represented by Formula [XIII] to prepare a compound represented by Formula 29, and then the above compound 29 is reacted with the compound represented by Formula [VIII], whereby the compound represented by Formula [XIV-bJ is produced, or (2) the above compound 28 is reacted with the compound represented by Formula [VIII] to prepare the compound represented by Formula XIV-a], and then the above compound [XIV-a] is reacted with the compound represented by Formula [XIII], whereby the compound represented by Formula [XIV-b] can be produced.

The compound represented by Formula 28 can be produced as well by reacting the compound represented by Formula 24 with ammonium chloride and cyanide to prepare a compound represented by Formula 27, and then the above compound 27 is reacted with the compound 1, followed by reducing the nitro group of the resulting compound.

A step for producing the compound 26 or 27 from the compound 24 can be carried out by reacting the compound 24 with cyanide such as potassium cyanide, sodium cyanide and trimethylsilyl cyanide and the compound 25 or ammonium chloride in a solvent such as water, methanol, ethanol and dioxane in the presence of acetic acid, sodium hydrogensulfite and hydrochloric acid, that is, applying a so-called Strecker reaction.

The use amount of the cyanide is 1 to 10 moles, preferably 2 to 3 moles per mole of the compound 24.

The use amount of the compound 25 or ammonium chloride is 1 to 10 moles, preferably 1 to 3 moles per mole of the compound 24.

The reaction temperature is usually 0° C. to the boiling point of the solvent used for the reaction, preferably 0° C. to a room temperature.

The reaction time is usually 30 minutes to 5 days, preferably 1 to 24 hours.

A step for producing the compound 28 from the compound 26 can be carried out by deblocking the protective group $R^{pp}$ according to the method described in the literature P described above.

A step for producing the compound 28 from the compound 27 can be carried out in the same manner as that of the step for producing the compound 6 from the compound 1 via the compound 3 in the production process A described above, and therefore the same reaction conditions can be applied.

A step for producing the compound 29 from the compound 28 and a step for producing the compound [XIV-b] from the compound [XIV-a] can be carried out respectively in the same manner as that of the step for reacting the compound represented by Formula [III with the compound represented by Formula [III] in the production process 1 described above, and therefore the same reaction conditions can be applied.

A step for producing the compound [XIV-a] from the compound 28 and a step for producing the compound [XIV-b] from the compound 29 can be carried out respectively in the same manner as that of the step for reacting the compound represented by Formula [VII] with the compound represented by Formula [VIII] in the production process 3 described above, and therefore the same reaction conditions can be applied.

Commercial products can be used for the compound represented by Formula 25, or it can be produced by suitably combining, if necessary, publicly known methods, the methods described in the reference examples or methods according to them.

Production process J

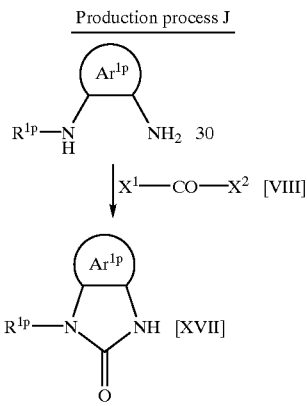

[wherein

, $R^{1p}$, $X^1$ and $X^2$ are synonymous with those described above].

The present production process is a process for producing a compound represented by Formula P[VII]. According to the present production process, the compound represented by Formula [XII] can be produced by reacting a compound represented by Formula 30 with the compound represented by Formula [VIII].

The present step can be carried out in the same manner as that of the step for reacting the compound represented by Formula [VII] with the compound represented by Formula [VIII] in the production process 3 described above, and therefore the same reaction conditions can be applied.

Commercial products can be used for the compound represented by Formula 30, or it can be produced by suitably combining, if necessary, publicly known methods, the methods described in the reference examples or methods according to them.

The substituents of the compounds obtained in the production process 1 to 10 and A to J described above can be converted, if necessary, to other substituents by subjecting them to chemical modification by methods which are well known in the field of organic chemistry, and this makes it possible to produce other desired compounds.

For example, when a hydroxyl group is present as the substituent, the above hydroxyl group can be converted, for example, to a carbamoyloxy group, a lower alkylcarbamoyloxy group, a di-(lower alkyl)carbamoyloxy group, an amino group or a lower alkoxy group which may have a substituent. Further, the hydroxyl group is oxidized to form a formyl group, and then a compound having the above formyl group can be subjected to various chain-elongating reactions or reductive amination.

A hydroxyl group can be converted to a carbamoyloxy group, a lower alkylcarbamoyloxy group or a di(lower alkyl)carbamoyloxy group by reacting a compound having the above hydroxyl group with, for example, phosgene, ammonia, lower alkylamine such as, for example, methylamine or di(lower alkyl)amine such as dimethylamine.

A hydroxyl group can be converted to an amino group can be carried via an azide group or a halogen atom.

An azide group can be converted to an amino group by catalytic reduction using a metal catalyst such as, for example, a palladium-carbon catalyst, phosphine reduction or reduction using a metal hydride complex.

A halogen atom can be converted to an amino group by substituting with an amino group or converting it to an azide group and then using the method described above.

A hydroxyl group can be converted to a lower alkoxy group which may have a substituent by, for example, a Williamson ether synthesis reaction.

A hydroxyl group can be oxidized to a formyl group by, for example, a Swern oxidation method, a pyridinium chlorochromate (PCC) oxidation method and a pyridinium dichromate (PDC) oxidation method.

The chain-elongating reaction can usually be carried out by a carbon-carbon bond-forming reaction which is well known in the field of organic chemistry, and the above carbon-carbon bond-forming reaction includes, for example, a substitution reaction or addition reaction which is carried out in the presence of a base; addition reaction which is carried out by reacting an organic metal reagent; a Michael type addition reaction; reaction with phosphonium salt or phosphonate in the presence of a base; a Wittig-corresponding reaction using a Topfer type reagent, a Nozaki-Lombard type reagent or a metal alkylidenecarbene complex; addition reaction which is carried out by converting to halide and then carrying out halogen-metal exchange or converting to tosylhydrazone and then reacting with an alkaline metal base such as t-butyllithium to thereby generate anion species; or a Simons-Smith reaction.

Further, when an amino group is present as the substituent, the above amino group can be converted to, for example, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group or a (di-lower alkylcarbamoyl)amino group.

An amino group can be converted to a (lower alkyl)sulfonylamino group by reacting a compound having the above amino group with, for example, (lower alkyl)sulfonyl chloride such as methanesulfonyl chloride.

An amino group can be converted to an aminosulfonylamino group, a (lower alkylamino)sulfonylamino group or a (di-lower alkylamino)sulfonylamino group by reacting a compound having the above amino group with, for example, sulfamoyl chloride, (lower alkyl)sulfamoyl chloride such as methylsulfamoyl chloride or a di(lower alkyl)sulfamoyl chloride such as dimethylsulfamoyl chloride.

An amino group can be converted to a carbamoylamino group, a (lower alkylcarbamoyl)amino group or a (di-lower alkylcarbamoyl)amino group by reacting a compound having the above amino group with, for example, phosgene and, for example, ammonia, lower alkylamine such as methylamine or di(lower alkyl)amine such as methylamine.

When the converting reactions of the substituents described above, it is preferable to carry out the reactions after suitably protecting functional groups which do not take part in the reactions and remove the above protective groups after finishing the reactions.

It is proved, for example, by the following pharmacological test examples that the compounds of the present invention are medicinally useful.

PHARMACOLOGICAL TEST EXAMPLE 1
(Nociceptin Receptor Binding Inhibition Assay)

cDNA which codes a human nociceptin receptor gene was cloned into an expression vector pCR3 (Invitrogen) to prepare pCR3/ORL1. Next, pCR3/ORL1 was transfected in CHO cells using a transfectam (Nippongene) to obtain a stable expression strain (CHO/ORL1 cells) having resistance against 1 mg/ml G418. Membranes were prepared from this stable expression strain to carry out a receptor binding assay.

The membrane of 11 μg, 50 pM [$^{125}$I] Tyr$^{14}$-Nociceptin (Amersham), 1 mg SPA (Amersham) and a tested compound were suspended in an NC buffer (50 mM Hepes, 10 mM sodium chloride, 1 mM magnesium chloride, 2.5 mM calcium chloride, 0.1% BSA, 0.025% bacitracin, pH 7.4) and incubated at 37° C. for 60 minutes, and then the radioactivity was determined. The binding activity to the nociceptin receptor was shown by the 50% inhibition concentration ($IC_{50}$ value) of [$^{125}$I] Tyr$^{14}$-Nociceptin binding by the compounds of the present invention having various concentrations. The results thereof are shown in Table 1.

TABLE 1

Nociceptin receptor binding inhibition effect

| Compound | $IC_{50}$ value (nM) |
|---|---|
| Example 6 | 8.0 |
| Example 24 | 6.1 |
| (3S*, 4S*) body of Example 42 | 1.8 |
| Example 68 | 3.0 |
| Example 95 | 2.3 |
| Example 102 | 1.9 |

PHARMACOLOGICAL TEST EXAMPLE 2
(Antagonism Against Nociceptin-Elicited G Protein Activation)

CHO cells which stably expressed a nociceptin receptor ORL1 were used to investigate the action of a tested compound against nociceptin-elicited G protein activation. A membrane prepared from the CHO/ORL1 cell, 50 nM nociceptin, 200 pM GTP γ[$^3$S] (NEN), 1.5 mg SPA (Amersham) and the tested compound were mixed in a GDP buffer (20 mM Hepes, 100 mM sodium chloride, 10 mM magnesium chloride, 1 mM EDTA, 5 μM GDP, pH 7.4) and incubated at 25° C. for 150 minutes, and then the radioactivity was determined. The antagonism against nociceptin-elicited G protein activation was shown by the 50% inhibition concentration ($IC_{50}$ value) of GTP γ[$^{35}$S] binding by the compounds of the present invention having various concentrations. The results thereof are shown in Table 2. This showed that the compounds of the present invention had antagonism against nociceptin-elicited G protein activation.

TABLE 2

Antagonism against nociceptin-elicited G protein activation

| Compound | $IC_{50}$ Value (nM) |
|---|---|
| Example 6 | 670 |
| Example 24 | 18 |
| (3S*, 4S*) body of Example 42 | 18 |
| Example 68 | 27 |
| Example 95 | 12 |
| Example 102 | 5.8 |

It can be found from the results described above that the compounds of the present invention specifically prevent nociceptin from bonding to a nociceptin receptor ORL1 and therefore are useful as an analgesic against diseases accompanied with pains such as cancerous pain, postoperative pain, migraine, gout, chronic rheumatism, chronic pain and neuralgia, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension.

The compound represented by Formula [I] can be administered orally or non-orally, and the formulation thereof to a form which is suited to such administration makes it possible to provide the compound as an analgesic, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension. When the compound of the present invention is clinically used, it is possible to add pharmaceutically acceptable additives in accordance with the administration forms thereof to convert the compound to various preparations and then administer them. In this case, various additives which are usually used in the preparation field can be used as the additives and include, for example, gelatin, lactose, white sugar, titanium oxide, starch, crystalline cellulose, hydroxypropylmethyl cellulose, carboxymethyl cellulose, corn starch, microcrystalline wax, white vaseline, magnesium metasilicate aluminate, anhydrous calcium phosphate, citric acid, trisodium citrate, hydroxypropyl cellulose, sorbitol, sorbitan fatty acid esters, polysorbate, sugar fatty acid esters, polyoxyethylene, hardened castor oil, polyvinylpyrrolidone, magnesium stearate, light silicic anhydride, talc, vegetable oils, benzyl alcohol, gum arabic, propylene glycol, polyalkylene glycol, cyclodextrin and hydroxypropyl cyclodextrin.

The forms of the pharmaceutical preparations obtained in the form of the mixtures of these additives include solid pharmaceutical preparations such as, for example, tablets, capsules, granules, powders and suppositories; and liquid pharmaceutical preparations such as, for example, syrups, elixirs and parenteral solutions, and they can be prepared according to conventional methods in the pharmaceutical preparation field. In the case of the liquid pharmaceutical preparations, they may be in a form in which they are dissolved or suspended in water or other suitable media in use. Further, particularly in the case of the parenteral solutions, they may be dissolved or suspended, if necessary, in a physiological saline solution or a glucose solution, and a buffer and a preservative may added thereto.

These pharmaceutical preparations can contain the compounds of the present invention in a proportion of 1.0 to 100% by weight, preferably 1.0 to 60% by weight based on the whole pharmaceutical components. These pharmaceutical preparations may contain other compounds which are therapeutically effective.

When the compounds of the present invention are used as an analgesic, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension, the dosage and administration frequency thereof are varied depending on the sexuality, age, body weight and degree of symptom of a patient and the kind and range of the intended therapeutic effects. In general, in the case of oral administration, the dosage of 0.01 to 20 mg/kg of an adult, which is divided into once to several times, is preferably administered a day, and in the case of non-oral administration, the dosage of 0.002 to 10 mg/kg of an adult, which is divided into once to several times, is preferably administered a day. Further, they can preventively be administered depending on symptoms.

BEST MODE FOR CARRYING OUT THE INVENTION

The present invention shall more specifically be explained with reference to examples and reference examples, but the present invention shall by no means be restricted by them.

Example 1

Production of 1-(1-cyclohexylmethyl-4-piperidyl)-5-methyl-1,3-dihydro-2H-benzimidazol-2-one Cyclohexylmethyl bromide of 58 mg was added to a dimethylformamide 3 ml suspension of 4-(2-keto-5-methyl-1-benzimidazolinyl)piperidine of 50 mg and potassium carbonate of 48 mg at a room temperature, and the suspension was heated to 80° C. and stirred for 2 hours. The reaction solution was allowed to come down to a room temperature and diluted with ethyl acetate. It was washed with water and saturated brine and dried on anhydrous sodium sulfate. Then, the solvent was distilled off, and the resulting residue was separated and refined by means of silica gel column chromatography (chloroform/methanol=20/1), whereby the captioned compound of 27 mg was obtained in the form of a colorless solid.

$^1$H-NMR (CDCl$_3$) δ: 0.80–1.85(13H, m), 2.06(2H, m), 2.16(2H, d, J=7.5 Hz), 2.36(3H, s), 2.40(2H, m), 3.00(2H, m), 4.32(1H, m), 6.87(2H, m), 7.15(1H, d, J=7.8 Hz)

FAB-MS (M+H)$^+$: 328

Example 2

Production of 1-(1-cyclopropylmethyl-4-piperidyl)-5-methyl-1,3-dihydro-2H-benzimidazol-2-one Cyclopropylmethyl bromide was used to obtain the captioned compound by the same method as that of Example 1.

$^1$H-NMR (CDCl$_3$) δ: 0.13(1H, m), 0.54(1H, m), 0.90(1H, m), 1.25(2H, s), 1.81(3H, m), 2.18(2H, m), 2.30–2.58(6H, m), 3.25(2H, m), 4.36(1H, m), 6.85(1H, d, J=8.1 Hz), 6.91(1H, s), 7.21(1H, d, J=8.1 Hz), 9.10(1H, brs)

FAB-MS (M+H)$^+$: 286

Example 3

Production of 1-(1-cyclooctylmethyl-4-piperidyl)-5-methyl-1,3-dihydro-2H-benzimidazol-2-one Sodium triacetoxyborohydride of 93 mg was added to a tetrahydrofuran 3 ml solution of 4-(2-keto-5-methyl-1-benzimidazolinyl)piperidine of 50 mg and cyclooctanecarbaldehyde of 62 mg, and the solution was stirred at a room temperature for 3 hours. The reaction solution was diluted with ethyl acetate and washed with a saturated sodium bicarbonate aqueous solution and saturated brine, followed by drying on anhydrous sodium sulfate. Then, the solvent was distilled off, and the resulting residue was separated and refined by means of silica gel column chromatography (ethyl acetate/hexane=3/1), whereby the captioned compound of 43 mg was obtained in the form of a colorless solid.

$_1$H-NMR (CDCl$_3$) δ: 1.25(2H, m), 1.40–1.85(15H, m), 2.04–2.20(4H, m), 2.35–2.48(5H, m), 3.02(2H, m), 4.32(1H, m), 6.85(1H, d, J=8.1 Hz), 6.90(1H, s), 7.15(1H, d, J=8.1 Hz), 8.66(1H, brs)
FAB-MS (M+H)$^+$: 356

Example 4
Production of 1-[1-(bicyclo4.4.0]dec-3-ylmethyl)-4-piperidyl]-5-methyl-1,3-dihydro-2H-benzimidazol-2-one Bicyclo[4.4.0]decane-3-carbaldehyde was used to obtain the captioned compound by the same method as that of Example 3.

$^1$H-NMR (CDCl$_3$) δ: 0.82–1.45(10H, m), 1.45–1.80(8H, m), 2.00–2.21(5H, m), 2.36(3H, s), 2.42(2H, m), 3.03(2H, m), 4.35(1H, m), 6.88(2H, m), 7.16(1H, d, J=7.8 Hz), 8.31(1H, brs)
FAB-MS (M+H)$^+$: 382

Example 5
Production of 1-[1-(bicyclo[4.4.0]dec-2-ylmethyl)-4-piperidyl]-5-methyl-1,3-dihydro-2H-benzimidazol-2-one Bicyclo[4.4.0]decane-2-carbaldehyde was used to obtain the captioned compound by the same method as that of Example 3.

$^1$H-NMR (CDCl$_3$) δ: 0.68–1.00(4H, m), 1.09–1.35(5H, m), 1.40–1.84(9H, m), 2.00(3H, m), 2.23(2H, m), 2.36(3H, s), 2.45(2H, m), 3.04(2H, m), 4.35(1H, m), 6.86(1H, d, J=8.1 Hz), 6.93(1H, s), 7.16(1H, d, J=8.1 Hz), 9.23(1H, brs)
FAB-MS (M+H)$^+$: 382

Example 6
Production of 1-(1-cyclooctylmethyl-4-piperidyl)-1,3-dihydro-2H-benzimidazol-2-one 4-(2-Keto-1-benzimidazolinyl)piperidine was used to obtain the captioned compound by the same method as that of Example 3.

$^1$H-NMR (CDCl$_3$) δ: 1.28(5H, m), 1.42–1.84(12H, m), 2.05–2.18(4H, m), 2.45(2H, m), 3.04(2H, m), 4.35(1H, m), 7.06(3H, m), 7.28(1H, m), 9.10(1H, br)
FAB-MS (M+H)$^+$: 342

Example 7
Production of 1-[1-(1-cyclohexylethyl)-4-piperidyl]-5-methyl-1,3-dihydro-2H-benzimidazol-2-one 1-Cyclohexylethyl p-toluenesulfonate was used to obtain the captioned compound by the same method as that of Example 1.

$^1$H-NMR (CDCl$_3$) δ: 0.92(3H, d, J=6.6 Hz), 1.19(2H, m), 1.25(5H, m), 1.75(5H, m), 2.10(1H, m), 2.26(3H, m), 2.37(3H, s), 2.40(1H, m), 2.64(1H, m), 2.80(2H, m), 4.28(1H, m), 6.87(2H, m), 7.14(1H, d, J=8.1 Hz), 8.52(1H, br)
FAB-MS (M+H)$^+$: 342

Example 8
Production of 1-[1-(1-cyclohexylethyl)-4-piperidyl]-1,3-dihydro-2H-benzimidazol-2-one 4-(2-Keto-1-benzimidazolinyl)piperidine and 1-cyclohexylethyl p-toluenesulfonate were used to obtain the captioned compound by the same method as that of Example 1.

$^1$H-NMR (CDCl$_3$) δ: 0.92(3H, d, J=6.6 Hz), 1.15–1.40 (7H, m), 1.68–1.89(5H, m), 2.12(1H, m), 2.20–2.50(4H, m), 2.68(1H, m), 2.84(2H, m), 4.33(1H, m), 7.08(3H, m), 7.32 (1H, m), 8.92(1H, brs)
FAB-MS (M+H)$^+$: 328

Example 9
Production of 1-[1-(tricyclo[3.3.1.1$^{3,7}$]dec-1-ylmethyl)-4-piperidyl]-1,3-dihydro-2H-benzimidazol-2-one 4-(2-Keto-1-benzimidazolinyl)piperidine and tricyclo-[3.3.1.1$^{3,7}$]decane-1-carbaldehyde were used to obtain the captioned compound by the same method as that of Example 3.

$^1$H-NMR (CDCl$_3$) δ: 1.52(4H, m), 1.70(9H, m), 1.96(6H, m), 2.42(4H, m), 2.89(2H, m), 4.29(1H, m), 7.08(3H, m), 7.28(1H, m), 8.76(1H, brs)
FAB-MS (M+H)$^+$: 366

Example 10
Production of 1-[1-(bicyclo[4.4.0]dec-2-ylmethyl)-4-piperidyl]-1,3-dihydro-2H-benzimidazol-2-one 4-(2-Keto-1-benzimidazolinyl)piperidine and bicyclo-[4.4.0]decane-2-carbaldehyde were used to obtain the captioned compound by the same method as that of Example 3.

$^1$H-NMR (CDCl$_3$) δ: 0.80–1.01(4H, m), 1.10–1.32(5H, m), 1.40–1.85(9H, m), 2.00(3H, m), 2.22(2H, m), 2.48(2H, m), 3.04(2H, m), 4.38(1H, m), 7.06(3H, m), 7.30(1H, m), 9.19(1H, br)
FAB-MS (M+H)$^+$: 368

Example 11
Production of 1-(1-cyclononylmethyl-4-piperidyl)-1,3-dihydro-2H-benzimidazol-2-one 4-(2-Keto-1-benzimidazolinyl)piperidine and cyclononane-carbaldehyde were used to obtain the captioned compound by the same method as that of Example 3.

$^1$H-NMR (CDCl$_3$) δ: 1.25(4H, m), 1.34(1H, m), 1.42–1.68 (9H, m), 1.79(3H, m), 2.14–2.20(5H, m), 2.45 (2H, m), 2.64(1H, s), 3.03(2H, m), 4.35(1H, m), 7.06(3H, m), 7.34(1H, m), 9.44(1H, br)
FAB-MS (M+H)$^+$: 356

Example 12
Production of 1-(1-cyclooctylmethyl-4-piperidyl)-3-(3-hydroxypropyl)-1,3-dihydro-2H-benzimidazol-2-one 1-(1-Cyclooctylmethyl-4-piperidyl)-1,3-dihydro-2H-benzimidazol-2-one obtained in Example 6 and t-butyldimethylsilyloxypropyl bromide were used to obtain the captioned compound by the same method as that of Example 30.

$^1$H-NMR (CDCl$_3$) δ: 1.25(2H, m), 1.40–1.98(18H, m), 2.05–2.19(4H, m), 2.45(2H, m), 3.03(2H, m), 3.54(2H, m), 4.07(2H, t, J=9.1 Hz), 4.36(1H, m), 7.02–7.15(3H, m), 7.32(1H, m)
FAB-MS (M+H)$^+$: 400

Example 13
Production of 1-(1-cyclooctylmethyl-4-piperidyl)-3-propargyl-1,3-dihydro-2H-benzimidazol-2-one 60% Sodium hydride of 6 mg was added to a dimethylformamide 3 ml solution of 1-(1-cyclooctylmethyl-4-piperidyl)-1,3-dihydro-2H-benzimidazol-2-one of 30 mg obtained in Example 6, and the solution was stirred at a room temperature for one hour. Then, propargyl bromide of 22 mg was added thereto, and the solution was further stirred at a room temperature for 30 minutes. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/2), whereby the captioned compound of 29 mg was obtained in the form of a colorless liquid.

$^1$H-NMR (CDCl$_3$) δ: 1.25(1H, m), 1.40–1.85(16H, m), 2.03–2.18(4H, m), 2.28(1H, t, J=2.7 Hz), 2.42(2H, m), 3.00(2H, m), 4.34(1H, m), 4.68(2H, d, J=2.7 Hz), 7.10(2H, m), 7.19(1H, m), 7.30(1H, m)
FAB-MS (M+H)$^+$: 380

Example 14
Production of 1-(1-cyclodecylmethyl-4-piperidyl)-1,3-dihydro-2H-benzimidazol-2-one 4-(2-Keto-1-benzimidazolinyl)piperidine and cyclodecane-carbaldehyde were used to obtain the captioned compound by the same method as that of Example 3.

$^1$H-NMR (CDCl$_3$) δ: 1.38–1.69(18H, m), 1.80(3H, m), 2.04–2.18(4H, m), 2.45(2H, m), 3.02(2H, m), 4.35(1H, m), 7.07(3H, m), 7.28(1H, m), 9.19(1H, brs)

FAB-MS (M+H)$^+$: 370

Example 15

Production of 1-(1-cyclooctylmethyl-4-piperidyl)-3-(4-pyridylmethyl)-1,3-dihydro-2H-benzimidazol-2-one hydrochloride 60% Sodium hydride of 9 mg was added to a dimethylformamide 3 ml solution of 1-(1-cyclooctylmethyl-4-piperidyl)-1,3-dihydro-2H-benzimidazol-2-one of 30 mg obtained in Example 6, and the solution was stirred at a room temperature for one hour. Then, a dimethylformamide 1 ml solution of 4-pyridylmethyl chloride of 46 mg was added thereto, and the solution was further stirred at a room temperature for 3 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=100/1). It was dissolved in 10% hydrogen chloride-methanol, and then the solvent was distilled off, whereby the captioned compound of 32 mg was obtained in the form of a white solid.

$^1$H-NMR (DMSO-d$_6$) δ: 1.28–2.12(17H, m), 2.88–3.08 (4H, 20 m), 3.17(2H, m), 3.60(2H, m), 4.65(1H, m), 5.38 (2H, s), 7.10(3H, m), 7.81(1H, d, J=4.8 Hz), 7.86(2H, d, J=6.6 Hz), 8.82(2H, d, J=6.6 Hz), 10.39(1H, br)

FAB-MS (M+H)$^+$: 433

Example 16

Production of 1-(1-cyclooctylmethyl-4-piperidyl)-3-methyl-1,3-dihydro-2H-benzimidazol-2-one Methyl iodide was used to obtain the captioned compound by the same method as that of Example 13.

$^1$H-NMR (CDCl$_3$) δ: 1.24(3H, m), 1.40–1.80(14H, m), 2.02–2.16(4H, m), 2.42(2H, m), 2.99(2H, m), 3.41(3H, s), 4.35(1H, m), 6.97 (1H, m), 7.07(2H, m), 7.27(1H, m)

FAB-MS (M+H)$^+$: 356

Example 17

Production of 1-(1-cyclooctylmethyl-4-piperidyl)-3-(3-pyridylmethyl)-1,3-dihydro-2H-benzimidazol-2-one hydrochloride 3-Pyridylmethyl chloride was used to obtain the captioned compound by the same method as that of Example 15.

$^1$H-NMR (DMSO-d$_6$) δ: 1.28–1.69(12H, m), 1.75(2H, m), 1.90(2H, m), 2.04(1H, m), 2.92(4H, m), 3.15(2H, m), 3.60(2H, m), 4.64 (1H, m), 5.26(2H, s), 7.06(2H, m), 7.26(1H, m), 7.87(2H, m), 8.31(1H, m), 8.78(1H, t, J=5.1 Hz), 8.88(1H, d, J=5.1 Hz), 10.50(1H, br)

FAB-MS (M+H)$^+$: 433

Example 18

Production of 1-(1-cyclooctylmethyl-4-piperidyl)-3-(2-pyridylmethyl)-1,3-dihydro-2H-benzimidazol-2-one hydrochloride 2-Pyridylmethyl chloride was used to obtain the captioned compound by the same method as that of Example 15.

$^1$H-NMR (DMSO-d$_6$) δ: 1.20–1.68(12H, m), 1.75(2H, m), 1.90(2H, m), 2.05(1H, m), 2.94(4H, m), 3.15(2H, m), 3.62(2H, m), 4.63 (11H, m), 5.24(2H, s), 7.06(3H, m), 7.38(1H, m), 7.46(1H, m), 7.76(1H, d, J=7.2 Hz), 7.95(1H, m), 8.60(1H, m), 10.18(1H, br)

FAB-MS (M+H)$^+$: 433

Example 19

Production of 1-(1-cycloheptyl-4-piperidyl)-1,3-dihydro-2H-benzimidazol-2-one 4-(2-Keto-1-benzimidazolinyl)piperidine and cycloheptyl-methyl methanesulfonate were used to obtain the captioned compound by the same method as that of Example 1.

$^1$H-NMR (CDCl$_3$) δ: 1.15(2H, m), 1.40–1.74(9H, m), 1.82 (4H, m), 2.05–2.19(4H, m), 2.45(2H, m), 3.01(2H, m), 4.35(1H, m), 7.08(3H, m), 7.28(1H, m), 9.36(1H, brs)

FAB-MS (M+H)$^+$: 328

Example 20

Production of 1-[1-(bicyclo[3.2.1]oct-3-ylmethyl)-4-piperidyl]-1,3-dihydro-2H-benzimidazol-2-one 4-(2-Keto-1-benzimidazolinyl)piperidine and bicyclo-[3.2.1]octane-1-carbaldehyde were used to obtain the captioned compound by the same method as that of Example 3.

$^1$H-NMR (CDCl$_3$) δ: 1.03(2H, t, J=12.0 Hz), 1.25–1.95 (11H, m), 2.04–2.25(6H, m), 2.42(2H, m), 3.01(2H, m), 4.35(1H, m), 7.07(3H, m), 7.28(1H, m), 9.30(1H, br)

FAB-MS (M+H)$^+$: 340

Example 21

Production of 1-[1-(1-cyclooctenylmethyl)-4-piperidyl]-1,3-dihydro-2H-benzimidazol-2-one 4-(2-Keto-1-benzimidazolinyl)piperidine and 1-cyclooctenecarbaldehyde were used to obtain the captioned compound by the same method as that of Example 3.

$^1$H-NMR (CDCl$_3$) δ: 1.45–1.68(8H, m), 1.79(2H, m), 2.00–2.15(4H, m), 2.25(2H, m), 2.44(2H, m), 2.88(2H, s), 3.04(2H, m), 4.35 (1H, m), 5.53(1H, t, J=7.8 Hz), 7.07(3H, m), 7.29(1H, m), 8.77(1H, br)

FAB-MS (M+H)$^+$: 340

Example 22

Production of 1-[1-(1-cyclodecenylmethyl)-4-piperidyl]-1,3-dihydro-2H-benzimidazol-2-one 4-(2-Keto-1-benzimidazolinyl)piperidine and 1-cyclodecenylmethyl methanesulfonate were used to obtain the captioned compound by the same method as that of Example 1.

$^1$H-NMR (CDCl$_3$) δ: 1.15–1.84(10H, m), 2.02–2.50(10H, m), 2.89(6/5H, s), 2.96(4/5H, s), 3.05(4H, m), 3.44(1H, m), 5.36(2/5H, t, J=9.0Hz), 5.66(3/51H, J=7.8Hz), 7.06(3H, m), 7.28(1H, m), 8.66(1H, brs)

FAB-MS (M+H)$^+$: 368

Example 23

Production of 1-[1-(1-ethylcyclooctylmethyl)-4-piperidyl]-1,3-dihydro-2H-benzimidazol-2-one (1) Production of 4-(2-nitrophenylamino)-1-(1-ethylcyclooctylmethyl)piperidine Sodium carbonate of 43 mg and potassium iodide of 40 mg were added to a cyclohexanol 2 ml solution of 4-amino-1-(1-ethyl-cyclooctylmethyl)piperidine of 100 mg and 2-fluoronitrobenzene of 57 mg, and the solution was heated and stirred at 150° C. for 3 hours. The reaction solution was allowed to come down to a room temperature and diluted with ethyl acetate. It was washed with water and saturated brine and dried on anhydrous sodium sulfate. Then, the solvent was distilled off, and the resulting residue was separated and refined by means of silica gel column chromatography (ethyl acetate/hexane=1/10), whereby the captioned compound of 140 mg was obtained in the form of a yellow oily substance.

(2) Production of 1-[1-(1-ethylcyclooctylmethyl)-4-piperidyl]-1,3-dihydro-2H-benzimidazol-2-one 4-(2-Nitrophenylamino)-1-(1-ethylcyclooctylmethyl)-piperidine of 140 mg was dissolved in a methanol 10 ml-chloroform 5 ml mixed solvent, and 10% palladium-carbon of 50 mg was added thereto. The solution was stirred at an atmospheric pressure and a room temperature for 3 hours under hydrogen atmosphere. The reaction solution was filtered through celite, and then the filtrate was condensed. Subsequently, the resulting residue was dissolved in chloroform of 10 ml, and carbonyldiimidazole of 130 mg was added thereto. The solution was stirred at a room temperature for one hour. The reaction solution was condensed, and the resulting residue was separated and refined by means of silica gel column chromatography (ethyl acetate/hexane=1/3), whereby the captioned compound of 123 mg was obtained in the form of a white solid.

$^1$H-NMR (CDCl$_3$) δ: 0.81(3H, t, J=7.5 Hz), 1.23(2H, m), 1.36(2H, q, J=7.5 Hz), 1.42–1.75(12H, m), 2.10(2H, s), 2.42(4H, m), 2.89(2H, m), 4.29(1H, m), 7.07(3H, m), 7.25 (1H, m), 8.25(1H, br)

FAB-MS (M+H)$^+$: 370

Example 24

Production of 1-(1-cyclooctylmethyl-4-piperidyl)-3-ethyl-1,3-dihydro-2H-benzimidazol-2-one Ethyl iodide was used to obtain the captioned compound by the same method as that of Example 13.

$^1$H-NMR (CDCl$_3$) δ: 1.26(3H, m), 1.34(3H, t, J=7.2 Hz), 1.40–1.80(14H, m), 2.03–2.18(4H, m), 2.42(2H, m), 2.98 (2H, m), 3.94 (2H, q, J=7.2 Hz), 4.34(1H, m), 7.00(1H, m), 7.05(2H, m), 7.28(1H, m)

FAB-MS (M+H)$^+$: 370

Example 25

Production of 1-(1-cyclooctylmethyl-4-piperidyl)-3-isopropyl-1,3-dihydro-2H-benzimidazol-2-one Isopropyl bromide was used to obtain the captioned compound by the same method as that of Example 13.

$^1$H-NMR (CDCl$_3$) δ: 1.25(3H, m), 1.43–1.84(20H, m), 2.02–2.18(4H, m), 2.43(2H, m), 2.99(2H, m), 4.36(1H, m), 4.74(1H, quintet, J=6.9 Hz), 7.05(2H, m), 7.14(1H, m), 7.28(1H, m)

FAB-MS (M+H)$^+$: 384

Example 26

Production of 1-(1-cyclooctylmethyl-4-piperidyl)-3-isobutyl-1,3-dihydro-2H-benzimidazol-2-one Isobutyl iodide was used to obtain the captioned compound by the same method as that of Example 13.

$^1$H-NMR (CDCl$_3$) δ: 0.96(6H, d, J=6.6 Hz), 1.26(3H, m), 1.42–1.84(14H, m), 2.02–2.28(5H, m), 2.43(2H, m), 2.99 (2H, m), 3.67 (2H, d, J=6.9 Hz), 3.34(1H, m), 6.98(1H, m), 7.05(2H, m), 7.28(1H, m)

FAB-MS (M+H)$^+$: 398

Example 27

Production of 1-[1-(2-methylenecyclooctylmethyl)-4-piperidyl]-1,3-dihydro-2H-benzimidazol-2-one (1) Production of 1-[1-(2-oxocyclooctylmethyl)-4-piperidyl]-1,3-dihydro-2H-benzimidazol-2-one 1N Hydrochloric acid of 1 ml and paraformaldehyde of 40 mg were added to an ethanol 3 ml solution of 4-(2-keto-1-benzimidazolinyl)piperidine of 218 mg while cooling with ice, and the solution was controlled to a room temperature. An ethanol 2 ml solution of cyclooctanone of 155 mg was added thereto, and then the solution was heated and stirred at 55° C. for 2 hours and at 75° C. for 16 hours. The reaction solution was condensed, and a saturated sodium bicarbonate aqueous solution of 10 ml was added to alkalinize the solution, followed by extracting with ethyl acetate. The organic layer was washed with saturated brine and dried on anhydrous sodium sulfate. Then, it was condensed to obtain the captioned compound of 330 mg in the form of a yellow oily substance.

$^1$H-NMR (CDCl$_3$) δ: 1.22–1.32(1H, m), 1.38–1.90(11H, m), 2.08–2.23(2H, m), 2.31–2.47(5H, m), 2.78(1H, dd, J=12 Hz, 8.9 Hz), 2.91–3.04(2H, brm), 3.09(1H, brd, J=12 Hz), 4.27–4.38(1H, m), 7.01–7.07(2H, m), 7.08–7.14(1H, m), 7.18–7.24(1H, m), 9.84(1H, brs)

FAB-MS (M+H)$^+$: 356

(2) Production of 1-[1-(2-hydroxy-2-methylcyclooctylmethyl)-4-piperidyl]-1,3-dihydro-2H-benzimidazol-2-one A tetrahydrofuran 2 ml solution of 1-[1-(2-oxocyclooctylmethyl)-4-piperidyl]-1,3-dihydro-2H-benzimidazol-2-one of 27 mg was allowed to come down to −76° C., and an ether solution (1.5 M) 0.15 ml of methyl lithium and a lithium bromide complex salt was added thereto, followed by stirring for 40 minutes. Water of 5 ml was added, and the solution was allowed to come up to a room temperature and extracted with ethyl acetate. The organic layer was washed with saturated brine and dried on anhydrous sodium sulfate. Then, it was condensed, and the resulting residue was separated and refined by means of silica gel column chromatography (chloroform/methanol= 20/1), whereby the captioned compound of 23 mg was obtained in the form of a yellow oily substance.

$^1$H-NMR (CDCl$^3$) δ: 1.34(3H, s), 1.38–1.67(10H, m), 1.76–1.85(3H, m), 1.91–2.03(2H, m), 2.15–2.31(2H, m), 2.34–2.51(2H, m), 2.65(1H, dd, J=13 Hz, 4.6 Hz), 2.78(1H, dd, J=13 Hz, 5.1 Hz), 3.12(1H, brd, J=11 Hz), 3.29(1H, brd, J=11 Hz), 4.35–4.46(1H, m), 5.9–6.4(1H, br), 6.98–7.10 (3H, m), 7.17–7.21(1H, m), 9.2–9.8(1H, br)

HR-MS (M+H)$^+$: 372.2633

(3) Production of 1-[1-(2-methylenecyclooctylmethyl)-4-piperidyl]-1,3-dihydro-2H-benzimidazol-2-one Triethylamine of 0.02 ml and methanesulfonyl chloride of 0.5 ml were added to an ethyl acetate 0.5 ml solution of 1-[1-(2-hydroxy-2-methylcyclooctylmethyl)-4-piperidyl]-1,3-dihydro-2H-benzimidazol-2-one of 29 mg, and the solution was stirred at a room temperature for one hour and 40 minutes. The resulting insoluble matters were filtered off, and the filtrate was condensed. Then, the residue thus obtained was dissolved in acetonitrile of 0.5 ml. A tetrahydrofuran 0.5 ml solution of 1,8-diazabicyclo[5.4.0]undecene of 20 mg was added thereto, and the solution was stirred at a room temperature for 13.5 hour. Then, the reaction solution was condensed, and the resulting residue was separated and refined by means of silica gel column chromatography (ethyl acetate), whereby the captioned compound of 16 mg was obtained in the form of a yellow oily substance.

$^1$H-NMR (CDCl$_3$) δ: 1.20–1.90(14H, m), 2.03–2.47(7H, m), 3.00–3.10(2H, m), 4.30–4.40(1H, m), 4.80(1H, s), 4.87 (1H, s), 7.03–7.11(3H, m), 7.26–7.30(1H, m), 9.40–9.75 (1H, br)

FAB-MS (M+H)$^+$: 354

Example 28

Production of 1-[1-(2-methylcyclooctylmethyl)-4-piperidyl]-1,3-dihydro-2H-benzimidazol-2-one 10% Palladium-carbon of 7 mg was added to an ethyl acetate 5 ml solution of 1-[1-(2-methylenecyclooctylmethyl)-4-piperidyl]-1,3-dihydro-2H-benzimidazol-2-one of 7 mg, and the solution was stirred for 21.5 hours under hydrogen flow. The insoluble matters were filtered off, and the filtrate was condensed. Then, the residue thus obtained was separated and refined by means of silica gel column chromatography (ethyl acetate), whereby the captioned compound of 2.5 mg was obtained in the form of an oily substance.

$^1$H-NMR (CDCl$_3$) δ: 0.81–0.96(3H, m), 1.20–1.50(7H, m), 1.53–1.73(3H, m), 1.77–2.0(7H, m), 2.07–2.30(3H, m), 2.37–2.50(2H, m), 4.27–4.40(1H, m), 7.04–7.10(2H, m), 7.26–7.30(2H, m), 8.59(1H, brs)

FAB-MS (M+H)$^+$: 356

Example 29
Production of 1-(1-cyclooctylmethyl-4-piperidyl)-3-propyl-1,3-dihydro-2H-benzimidazol-2-one Propyl iodide was used to obtain the captioned compound by the same method as that of Example 13.

$^1$H-NMR (CDCl$_3$) δ: 0.98(3H, t, J=7.5 Hz), 1.27(3H, m), 1.44–1.80(18H, m), 2.03–2.15(4H, m), 2.42(2H, m), 2.98 (2H, m), 3.84 (2H, t, J=7.2 Hz), 4.36(1H, m), 6.99(1H, m), 7.06(2H, m), 7.28(1H, m)

FAB-MS (M+H)$^+$: 384

Example 30
Production of 1-(1-cyclooctylmethyl-4-piperidyl)-3-(2-hydroxyethyl)-1,3-dihydro-2H-benzimidazol-2-one 60% Sodium hydride of 9 mg was added to a dimethylformamide 3 ml solution of 1-(1-cyclooctylmethyl-4-piperidyl)-1,3-dihydro-2H-benzimidazol-2-one of 30 mg obtained in Example 6, and the solution was stirred at a room temperature for one hour. Then, a dimethylformamide 1 ml solution of t-butyldimethylsilyloxyethyl bromide of 69 mg was added thereto, and the solution was further stirred at a room temperature for 3 hours. The reaction solution was diluted with ethyl acetate and washed with water and saturated brine, followed by drying on anhydrous sodium sulfate. Then, the solvent was distilled off, and chloroform 3 ml was added to the resulting residue. Subsequently, a 1M tetrabuyl ammonium fluoride-tetrahydrofuran solution of 0.35 ml was added thereto at a room temperature, and the solution was stirred for one hour. The reaction solution was condensed, and the resulting residue was separated and refined by means of silica gel column chromatography (chloroform/methanol=100/1), whereby the captioned compound of 16 mg was obtained in the form of a white solid.

$^1$H-NMR (CDCl$_3$) δ: 1.25(2H, m), 1.38–1.83(15H, m), 2.02–2.16(4H, m), 2.43(2H, m), 3.00(2H, m), 3.97(2H, t, J=5.4 Hz), 4.05(2H, t, J=5.4 Hz), 4.35(1H, m), 7.18(3H, m), 7.20(1H, m)

FAB-MS (M+H)$^+$: 386

Example 31
Production of 1-(1-cyclooctylmethyl-4-piperidyl)-3-methoxymethyl)-1 13-dihydro-2H-benzimidazol-2-one Methoxymethyl chloride was used to obtain the captioned compound by the same method as that of Example 13.

$^1$H-NMR (CDCl$_3$) δ: 1.26(2H, m), 1.40–1.82(15H, m), 2.04–2.18(4H, m), 2.44(2H, m), 3.00(2H, m), 3.37(3H, s), 3.46(1H, m), 5.29(2H, s), 7.07–7.18(3H, m), 7.29(1H, m)

FAB-MS (M+H)$^+$: 386

Example 32
Production of 1-(1-cyclooctylmethyl-4-piperidyl)-3-(2-methoxyethyl)-1,3-dihydro-2H-benzimidazol-2-one Methoxyethyl bromide was used to obtain the captioned compound by the same method as that of Example 13.

$^1$H-NMR (CDCl$_3$) δ: 1.25(2H, m), 1.40–1.82(15H, m), 2.02–2.18(4H, m), 2.43(2H, m), 3.00(2H, m), 3.34(3H, s), 3.68(2H, t, J=5.7 Hz), 4.05(2H, t, J=5.7 Hz), 4.35(1H, m), 7.08(3H, m), 7.28(1H, m)

FAB-MS (M+H)$^+$: 400

Example 33
Production of 1-(1-cyclooctylmethyl-4-piperidyl)-3-(2-dimethylaminoethyl)-1,3-dihydro-2H-benzimidazol-2-one dihydrochloride Dimethylaminoethyl chloride hydrochloride was used to obtain the captioned compound by the same method as that of Example 15.

$^1$H-NMR (DMSO-d$^6$) δ: 1.30–1.92(15H, m), 2.83(3H, s), 2.85(3H, s), 2.95(2H, m), 2.34(2H, m), 3.40(2H, t, J=6.3 Hz), 3.56–3.72(6H, m), 4.24(2H, t, J=6.3 Hz), 4.59(1H, m), 7.10(2H, m), 7.36(1H, 30 m), 7.82(1H, m), 10.52(2H, br)

FAB-MS (M+H)$^+$: 412

Example 34
Production of 1-(1-cyclooctylmethyl-4-piperidyl)-3-(2-diethylaminoethyl)-1,3-dihydro-2H-benzimidazol-2-one dihydro-chloride Diethylaminoethyl bromide hydrobromide was used to obtain the captioned compound by the same method as that of Example 15.

$^1$H-NMR (DMSO-d$^6$) δ: 1.21(6H, t, J=7.2 Hz), 1.30–1.92 (15 H, m), 2.92(4H, m), 3.06–3.55(10H, m), 3.60(2H, m), 4.27(2H, t, J=6.6 Hz), 4.59(1H, m), 7.10(1H, m), 7.41(1H, m)7.80(1H, m), 10.46(1H, br), 10.70(1H, br)

FAB-MS (M+H)$^+$: 440

Example 35
Production of 1-[(3RS,4RS)-1-cyclooctylmethyl-3-methyl-4-piperidyl]-1,3-dihydro-2H-benzimidazol-2-one (1) Production of 1-benzyl-3-methyl-4-aminopiperidine Ammonium acetate of 1.9 g and sodium cyanoborohydride of 310 mg were added to a methanol 20 ml solution of 1-benzyl-3-methyl-4-piperidone of 500 mg, and the solution was stirred at a room temperature for 5 hours. The reaction solution was diluted with ethyl acetate and washed with IN sodium hydroxide, followed by drying on anhydrous sodium sulfate. Then, the solvent was distilled off, whereby the captioned compound of 470 mg was obtained in the form of an oily substance.

(2) Production of (3RS,4RS)-3-methyl-4-(2-nitrophenylamino)-1-benzylpiperidine

Sodium carbonate 245 mg and potassium iodide of 20 mg were added to a cyclohexanol 5 ml solution of 1-benzyl-3-methyl-4-aminopiperidine of 470 mg and 2-fluoronitrobenzene of 325 mg, and the solution was heated and stirred at 150° C. for 4 hours. The reaction solution was allowed to come down to a room temperature and diluted with ethyl acetate. It was washed with water and saturated brine and dried on anhydrous sodium sulfate. Then, the solvent was distilled off, and the resulting residue was separated and refined by means of silica gel column chromatography (ethyl acetate/hexane=1/10), whereby obtained were the captioned compound (3RS,4RS)-3-methyl-4-(2-nitrophenylamino)-1-benzylpiperidine of 287 mg in the form of a yellow oily substance and (3RS,4SR)-3-methyl-4-(2-nitrophenylamino)-1-benzylpiperidine of 218 mg in the form of a yellow oily substance.

(3) Production of 1-[(3RS,4RS)-1-benzyl-3-methyl-4-piperidyl]-1,3-dihydro-2H-benzimidazol-2-one (3RS,4RS)-3-methyl-4-(2-nitrophenylamino)-1-benzyl-piperidine of 285 mg was dissolved in a methanol 10 ml-chloroform 1 ml mixed solvent, and 10% palladium-carbon of 80 mg was added thereto. The solution was stirred at an atmospheric pressure and a room temperature for 4 hours under hydrogen atmosphere. The reaction solution was filtered through celite, and then the filtrate was condensed. Subsequently, the resulting residue was dissolved in chloroform of 10 ml, and carbonyldiimidazole of 220 mg was added thereto. The solution was stirred at a room temperature for 15 hours. The reaction solution was condensed, and the resulting residue was separated and refined by means of silica gel column chromatography (chloroform/methanol=100/1), whereby the captioned compound of 155 mg was obtained in the form of a white solid.

(4) Production of (3RS,4RS)-4-(2-keto-1-benzimidazolinyl)-3-methylpiperidine

1-[(3RS,4RS)-1-benzyl-3-methyl-4-piperidyl]-1,3-dihydro-2H-benzimidazol-2-one of 150 mg was dissolved in a mixed solvent of methanol 5 ml and chloroform 3 ml, and 20% palladium hydroxide of 50 mg was added thereto. The solution was stirred at 3 atm and a room temperature for 12 hours under hydrogen atmosphere. The reaction solution was filtered through celite, and the solvent in the filtrate was distilled off, whereby the captioned compound of 140 mg was obtained in the form of a white solid.

(5) Production of 1-[(3RS,4RS)-1-cyclooctylmethyl-4-piperidyl]-1,3-dihydro-2H-benzimidazol-2-one (3RS,4RS)-4-(2-keto-1-benzimidazolinyl)-3-methylpiperidine and cyclooctanecarbaldehyde were used to obtain the captioned compound by the same method as that of Example 3.

$^1$H-NMR (CDCl$_3$) δ: 0.76(3H, d, J=6.6 Hz), 1.26(2H, m), 1.45–1.82(14H, m), 2.13(4H, m), 2.42(1H, m), 2.55(1H, m), 2.99(2H, m), 3.98(1H, m), 7.07(3H, m), 7.25(1H, m), 8.48 (1H, brs)

FAB-MS (M+H)$^+$: 355

Example 36

Production of 1-[(3RS,4SR)-1-cyclooctylmethyl-3-methyl-4-piperidyl]-1,3-dihydro-2H-benzimidazol-2-one (3RS,4SR)-3-methyl-4-(2-nitrophenylamino)-1-benzyl-piperidine obtained in Example 35 (2) was used to obtain the captioned compound by the same methods as those of Example 35 (3), (4) and (5).

$^1$H-NMR (CDCl$_3$) δ: 1.16(3H, d, J=7.2 Hz), 1.45–1.80 (14H, m), 2.04(3H, m), 2.28(2H, m), 2.76(1H, m), 3.03(2H, m), 4.46(1H, m), 7.05(3H, m), 7.20(1H, m), 8.31(1H, brs)

FAB-MS (M+H)$^+$: 355

Example 37

Production of 1-[(3RS,4RS)-1-cyclooctylmethyl-3-ethoxycarbonyl-4-piperidyl]-1,3-dihydro-2H-benzimidazol-2-one (1) Production of 1-cyclooctylmethyl-3-ethoxycarbonyl-4-piperidone Sodium triacetoxyborohydride of 1000 mg was added to a tetrahydrofuran 25 ml solution of 3-ethoxycarbonyl-4-piperidone hydrochloride of 500 mg and cyclooctanecarbaldehyde of 420 mg, and the solution was stirred at a room temperature for 13 hours. The reaction solution was diluted with ethyl acetate and washed with a saturated sodium bicarbonate aqueous solution and saturated brine, followed by drying on anhydrous sodium sulfate. Then, the solvent was distilled off, and the resulting residue was separated and refined by means of silica gel column chromatography (ethyl acetate/hexane=30/1), whereby the captioned compound of 325 mg was obtained in the form of a colorless solid.

(2) Production of (3RS,4RS)-1-cyclooctylmethyl-3-ethoxycarbonyl-4-(2-nitrophenylamino)piperidine Ammonium acetate of 523 mg and sodium cyanoborohydride of 85 mg were added to a methanol 10 ml solution of 1-cyclooctylmethyl-3-ethoxycarbonyl-4-piperidone of 200 mg, and the solution was stirred at a room temperature for 3 hours. The reaction solution was diluted with ethyl acetate and washed with 1N sodium hydroxide, followed by drying on anhydrous sodium sulfate. Then, the solvent was distilled off, and the resulting residue was dissolved in cyclohexanol of 1 ml. 2-Fluoronitrobenzene of 116 mg, sodium carbonate of 88 mg and potassium iodide of 10 mg were added thereto, and the solution was heated and stirred at 150° C. for 17 hours. The reaction solution was allowed to come down to a room temperature and diluted with ethyl acetate. It was washed with saturated brine and dried on anhydrous sodium sulfate. Then, the solvent was distilled off, and the resulting residue was separated and refined by means of silica gel column chromatography (ethyl acetate/hexane=10 /1) and preparative thin layer chromatography [Kiselgel™60F$_{254}$, Art 5744 (manufactured by Merck Co., Ltd.); ethyl acetate/hexane=2/1], whereby obtained were the captioned compound of 67 mg in the form of a yellow oily substance and an isomer (3RS,4SR)-1-cyclooctylmethyl-3-ethoxycarbonyl-4-(2-nitrophenylamino)piperidine of 30 mg in the form of a yellow oily substance.

(3) Production of 1-[(3RS,4RS)-1-cyclooctylmethyl-3-ethoxycarbonyl-4-piperidyl]-1,3-dihydro-2H-benzimidazol-2-one (3RS,4RS)-1-cyclooctylmethyl-3-ethoxycarbonyl-4-(2-nitrophenylamino)piperidine was used to obtain the captioned compound by the same method as that of Example 35 (3).

1H-NMR (CDCl$_3$) δ: 0.96(3H, t, J=7.5 Hz), 1.25(2H, m), 1.44–1.83(14H, m), 2.16(3H, m), 2.25(1H, t, J=11.7 Hz), 2.56(1H, m), 3.00(1H, m), 3.19(1H, m), 3.64(1H, m), 3.90 (2H, m), 4.40(1H, m), 7.05(3H, m), 7.16(1H, m), 8.40(1H, brs)

FAB-MS (M+H)$^+$: 414

Example 38

Production of 1-[(3RS,4SR)-1-cyclooctylmethyl-3-ethoxycarbonvl-4-piperidyl]-1,3-dihydro-2H-benzimidazol-2-one (3RS,4SR)-1-cyclooctylmethyl-3-ethoxycarbonyl-4-(2-nitrophenylamino)piperidine obtained in Example 37 (2) was used to obtain the captioned compound by the same method as that of Example 35 (3).

$^1$H-NMR(CDCl$_3$) δ: 1.09(3H, t, J=7.2 Hz), 1.21(2H, m), 1.42–1.75(14H, m), 1.99(1H, m), 2.10(1H, m), 2.17(2H, m), 2.38(1H, m), 3.06(1H, m), 3.28(1H, m), 3.34(1H, m), 3.98 (2H, m), 4.36(1H, m), 7.02(3H, m), 7.53(1H, m), 8.10(1H, brs)

FAB-MS(M+H)$^+$: 414

Example 39

Production of 1-[(3RS,4RS)-1-cyclooctylmethyl-3-hydroxymethyl-4-piperidyl]-1,3-dihydro-2H-benzimidazol-2-one Lithium aluminum hydride of 3 mg was added to a tetrahydrofuran 2 ml solution of 1-[(3RS,4RS)-1-cyclooctylmethyl-3-ethoxycarbonyl-4-piperidyl]-1,3-dihydro-2H-benzimidazol-2-one of 12 mg, and the solution was stirred at a room temperature for one hour. Ethyl acetate of 1 ml was added to the reaction solution, and it was stirred for 5 minutes. Then, the reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=30/1), whereby the captioned compound of 5 mg was obtained in the form of a colorless solid.

1H-NMR(CDCl₃) δ: 1.25(2H, m), 1.35–1.90(15H, m), 2.05–2.30(4H, m), 2.36(1H, m), 2.62(1H, m), 3.03(2H, m), 3.38(2H, m), 4.38(1H, m), 7.08(3H, m), 7.30(1H, m), 9.18 (1H, brs)

FAB-MS(M+H)⁺: 372

Example 40

Production of 1-[(3RS,4SR)-1-cyclooctylmethyl-3-hydroxymethyl-4-piperidyl]-1,3-dihydro-2H-benzimidazol-2-one 1-[(3RS,4SR)-1-cyclooctylmethyl-3-ethoxycarbonyl-4-piperidyl]-1,3-dihydro-2H-benzimidazol-2-one was used to obtain the captioned compound by the same method as that of Example 39.

¹H-NMR (CDCl₃) δ: 1.10–1.90(18H, m), 2.04(1H, m), 2.15(2H, m), 2.61(1H, m), 3.15(2H, m), 3.38(1H, m), 3.92 (1H, m), 4.70(1H, m), 7.08(3H, m), 7.87(1H, m), 9.21(1H, brs)

FAB-MS (M+H)⁺: 372

Example 41

Production of 1-[(3RS,4RS)-1-cyclooctylmethyl-3-ethoxycarbonyl-4-piperidyl]-3-ethyl-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one and ethyl iodide were used to obtain the captioned compound by the same method as that of Example 13.

¹H-NMR (CDCl₃) δ: 0.91(3H, t, J=7.2 Hz), 1.25(2H, m), 1.32(3H, t, J=7.2 Hz), 1.42–1.80(13H, m), 2.17(4H, m), 2.26(1H, t, J=11.4 Hz), 2.58(1H, m), 2.99(1H, m), 3.18(1H, m), 3.66(1H, m), 3.86 (2H, q, J=7.2 Hz), 3.91(2H, q, J=7.2 Hz), 4.39(1H, m), 6.98(1H, m), 7.06(2H, m), 7.16(1H, m)

FAB-MS (M+H)⁺: 442

Example 42

Production of 1-[(3RS,4RS)-1-cyclooctylmethyl-3-hydroxymethyl-4-piperidyl]-3-ethyl-1,3-dihydro-2H-benzimidazol-2-one 1-[(3RS,4RS)-1-cyclooctylmethyl-3-ethoxycarbonyl-4-piperidyl]-3-ethyl-1,3-dihydro-2H-benzimidazol-2-one was used to obtain the captioned compound by the same method as that of Example 39.

¹H-NMR (CDCl₃) δ: 1.24(2H, m), 1.34(3H, t, J=7.2 Hz), 1.40–1.78(13H, m), 1.89(1H, m), 2.04–2.33(6H, m), 2.61 (1H, m), 3.00(2H, m), 3.34(2H, m), 3.96(2H, m), 4.39(1H, m), 7.08(3H, m), 7.32(1H, m)

FAB-MS (M+H)⁺: 400

Optical resolution of 1-[(3RS,4RS)-1-cyclooctylmethyl-3-hydroxymethyl-4-piperidyl]-3-ethyl-1,3-dihydro-2H-benzimidazol-2-one obtained above was carried out using an optical resolution column (CHIRALPAK AD column manufactured by Daicel Co., Ltd.; 0.1% diethylamine, hexane/isopropyl alcohol=800/200), and obtained were a compound called a (3R*,4R*) body of the captioned compound, $[\alpha]_D^{20}$ −6.20° (c=1.000, 0.1N HCl) (in the form of hydrochloride) for the sake of convenience from the former fraction and a compound called a (3S*,4S*) body of the captioned compound, $[\alpha]_D^{20}$ +6.400 (c=1.000, 0.1N HCl) (in the form of hydrochloride) for the sake of convenience from the latter fraction.

Example 43

Production of 1-[(3RS,4RS)-1-cyclooctylmethyl-3-ethoxycarbonvl-4-piperidyl]-3-propyl-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one and propyl iodide were used to obtain the captioned compound by the same method as that of Example 13.

¹H-NMR (CDCl₃) δ: 0.91(3H, t, J=7.1 Hz), 0.95(3H, t, J=7.4 Hz), 1.22(2H, m), 1.40–1.80(16H, m), 2.16(3H, m), 2.26(1H, t, J=11.4 Hz), 2.58(1H, m), 2.98(1H, m), 3.16(1H, m), 3.67(1H, m), 3.83 (2H, t, J=7.4 Hz), 3.86(2H, q, J=7.1 Hz), 4.39(1H, m), 6.96(1H, m), 7.05(2H, m), 7.15(1H, m)

FAB-MS (M+H)⁺: 456

Example 44

Production of 1-[(3RS,4RS)-1-cyclooctylmethyl-3-hydroxymethyl-4-piperidyl]-3-propyl-1,3-dihydro-2H-benzimidazol-2-one 1-[(3RS,4RS)-1-cyclooctylmethyl-3-ethoxycarbonyl-4-piperidyl]-3-propyl-1,3-dihydro-2H-benzimidazol-2-one was used to obtain the captioned compound by the same method as that of Example 39.

¹H-NMR (CDCl₃) δ: 0.96(3H, t, J=7.2 Hz), 1.24(2H, m), 1.40–1.92(18H, m), 2.16(3H, m), 2.26(1H, m), 2.60(1H, m), 3.00(2H, m), 3.33(2H, m), 3.87(2H, t, J=7.2 Hz), 4.39(1H, m), 7.06(3H, m), 7.31(1H, m)

FAB-MS (M+H)⁺: 414

Optical resolution of 1-[(3RS,4RS)-1-cyclooctylmethyl-3-hydroxymethyl-4-piperidyl]-3-propyl-1,3-dihydro-2H-benzimidazol-2-one obtained above was carried out using an optical resolution column (CHIRALPAK AD column manufactured by Daicel Co., Ltd.; 0.1% diethylamine, hexane/isopropyl alcohol=800/200), and obtained were a compound called a (3R*,4R*) body of the captioned compound for the sake of convenience from the former fraction and a compound called a (3S*,4S*) body of the captioned compound for the sake of convenience from the latter fraction.

Example 45

Production of 1-[(3RS,4RS)-1-(bicyclo[4.4.0]dec-2-ylmethyl)-3-hydroxymethyl-4-piperidyl]-1,3-dihydro-2H-benzimidazol-2-one (1) Production of 1-[(3RS,4RS)-1-benzyl-3-ethoxycarbonyl-4-piperidyl]-1,3-dihydro-2H-benzimidazol-2-one 1-Benzyl-3-ethoxycarbonyl-4-piperidone was used to obtain the captioned compound by the same methods as those of Example 37 (2) and (3).

(2) Production of 1-[(3RS,4RS)-3-ethoxycarbonyl-4-piperidyl]-1,3-dihydro-2H-benzimidazol-2-one 1-[(3RS,4RS)-1-benzyl-3-ethoxycarbonyl-4-piperidyl]-1,3-dihydro-2H-benzimidazol-2-one was used to obtain the captioned compound by the same method as that of Reference Example 2 (3).

(3) Production of 1-[(3RS,4RS)-1-(bicyclo[4.4.0]dec-2-ylmethyl)-3-ethoxycarbonyl-4-piperidyl]-1,3-dihydro-2H-benzimidazol-2-one 1-[(3RS,4RS)-3-ethoxycarbonyl-4-piperidyl]-1,3-dihydro-2H-benzimidazol-2-one and bicyclo[4.4.0]decane-2-carbaldehyde were used to obtain the captioned compound by the same method as that of Example 3.

(4) Production of 1-[(3RS,4RS)-1-(bicyclo[4.4.0]dec-2-ylmethyl)-3-hydroxymethyl-4-piperidyl]-1,3-dihydro-2H-benzimidazol-2-one 1-[(3RS,4RS)-1-(bicyclo[4.4.0]dec-2-ylmethyl)-3-ethoxy-carbonyl-4-piperidyl]-1,3-dihydro-2H-benzimidazol-2-one was used to obtain the captioned compound by the same method as that of Example 39.

¹H-NMR (CDCl₃) δ: 0.80–1.04(4H, m), 1.06–2.72(21H, m), 2.92–3.18(2H, m), 3.39(2H, s), 4.30–4.43(1H, m), 7.03–7.34(4H, m), 9.10(1H, s)

FAB-MS (M+H)⁺: 398

Example 46

Production of 1-[(3RS,4RS)-1-cyclononylmethyl-3-hydroxymethyl-4-piperidyl]-1,3-dihydro-2H-benzimidazol-2-one (1) Production of 1-[(3RS,4RS)-1-cyclononylmethyl-3-ethoxycarbonyl -4-piperidyl]-1,3-dihydro-2H-benzimidazol-2-one 1-[(3RS,4RS)-3-ethoxycarbonyl-4-piperidyl]-1,3-dihydro-2H-benzimidazol-2-one obtained in Example 45 (2) and cyclononanecarbaldehyde were used to obtain the captioned compound by the same method as that of Example 3.
(2) Production of 1-[(3RS,4RS)-1-cyclononylmethyl-3-hydroxymethyl-4-piperidyl]-1,3-dihydro-2H-benzimidazol-2-one 1-[(3RS,4RS)-1-cyclononylmethyl-3-ethoxycarbonyl-4-piperidyl]-1,3-dihydro-2H-benzimidazol-2-one was used to obtain the captioned compound by the same method as that of Example 39.

$^1$H-NMR(CDCl$_3$) δ: 0.78–0.92(4H, m), 1.08–2.40(19H, m), 2.51–2.68(1H, m), 3.03(2H, m), 3.38(2H, s), 4.24–4.43 (2H, m), 7.04–7.34(4H, m), 8.46(1H, br)

FAB-MS(M+H)$^+$: 386

Example 47

Production of 1-[1-cyclooctylmethyl-3 3-bis (hydroxymethyl)-4-piperidyl]-1,3-dihydro-2H-benzimidazol-2-one hydrochloride (1) Production of 1-benzyl-3,3-bis(hydroxymethyl)-4-piperidone 1-Benzyl-4-piperidone of 0.96 g was dissolved in tetrahydrofuran of 10 ml, and 35% formaldehyde of 0.6 ml was added thereto. This was cooled with ice, and an aqueous solution 20 ml of potassium carbonate 104 mg was added thereto. Then, the solution was stirred for 2.5 hours. The reaction solution was extracted with ethyl acetate, and the organic layer was washed with saturated brine and dried on anhydrous sodium sulfate. Then, the solvent was distilled off, and the resulting residue was separated and refined by means of silica gel column chromatography (ethyl acetate/hexane=3/1), whereby the captioned compound of 266 mg was obtained in the form of colorless crystal.
(2) Production of 1-benzyl-3,3-bis[(methoxymethyloxy)methyl]-4-piperidone 1-Benzyl-3,3-bis(hydroxymethyl)-4-piperidone of 259 mg was dissolved in methylene chloride of 4 ml, and methoxymethyl chloride of 0.18 ml and diisopropylethylamine of 0.45 ml were added at 0° C. under nitrogen atmosphere, followed by stirring at a room temperature for 11 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/3), whereby the captioned compound of 236 mg was obtained in the form of a colorless oily substance.
(3) Production of 1-benzyl-3,3-bis[(methoxymethyloxy)methyl]-4-(2-nitrophenylamino)piperidine 1-Benzyl-3,3-bis[(methoxymethyloxy)methyl]-4-piperidone was used to obtain the captioned compound by the same methods as those of Example 35 (1) and (2).
(4) Production of 1-[1-cyclooctylmethyl-3,3-bis [(methoxymethyloxy)methyl]-4-piperidyl]-1,3-dihydro-2H-benzimidazol-2-one 1-Benzyl-3,3-bis[(methoxymethyloxy)methyl]-4-(2-nitrophenylamino)piperidine was used to obtain the captioned compound by the same methods as those of Example 35 (3), (4) and (5).
(5) Production of 1-[1-cyclooctylmethyl-3,3-bis (hydroxymethyl)-4-piperidyl]-1,3-dihydro-2H-benzimidazol-2-one 1-[1- Cyclooctylmethyl-3,3-bis [(methoxymethyloxy)-methyl]-4-piperidyl]-1,3-dihydro-2H-benzimidazol-2-one of 7 mg was dissolved in tetrahydrofuran of 0.2 ml, and 6N hydrochloric acid of 2 ml was added thereto, followed by stirring at 60° C. for 4 hours. The reaction solution was condensed to obtain the captioned compound of 9 mg in the form of colorless powder.

$^1$H-NMR (D$_2$O) δ: 1.32–1.79(17H, m), 1.95–2.14(4H, m), 3.00–3.06(2H, br), 3.14–3.78(9H, m), 7.07–7.31(4H, m)

FAB-MS (M+H)$^+$: 402

Example 48

Production of 1-[1-cyclooctylmethyl-3,3-bis (hydroxymethyl)-4-piperidyl]-3-ethyl-1,3-dihydro-2H-benzimidazol-2-one
(1) Production of 1-[1-cyclooctylmethyl-3,3-bis [(methoxymethyloxy)-methyl]-4-piperidyl]-3-ethyl-1,3-dihydro-2H-benzimidazol-2-one 1-[1-Cyclooctylmethyl-3,3-bis[(methoxymethyloxy)-methyl]-4-piperidyl]-1,3-dihydro-2H-benzimidazol-2-one obtained in Example 47 (4) and ethyl iodide were used to obtain the captioned compound by the same method as that of Example 13.

(2) Production of 1-[1-cyclooctylmethyl-3,3-bis (hydroxymethyl)-4-piperidyl]-3-ethyl-1,3-dihydro-2H-benzimidazol-2-one 1-[1-Cyclooctylmethyl-3,3-bis [(methoxymethyloxy)-methyl]-4-piperidyl]-3-ethyl-1,3-dihydro-2H-benzimidazol-2-one was used to obtain the captioned compound by the same method as that of Example 47 (5).

$^1$H-NMR (CD$_3$OD) δ: 1.31(3H, t, J=7.2 Hz), 1.36–1.87 (15H, m), 1.96–2.04(1H, m), 2.17–2.25(1H, m), 3.05(2H, brd, J=7.8 Hz), 3.13–3.35(2H, m), 3.52–3.62(4H, m), 3.65–3.82(2H, m), 3.93–4.03(2H, m), 7.10–7.27(3H, m), 7.72–7.75(1H, m)

FAB-MS (M+H)$^+$: 430

Example 49

Production of 1-[(2RS,4RS)-1-cyclooctylmethyl-2-hydroxymethyl-4-piperidyl]-3-ethyl-1,3-dihydro-2H-benzimidazol-2-one
(1) Production of 1-benzyl-6-methoxycarbonyl-1,6-dihydro-4(5H)-pyridinone A molecular sieve 3A of 4 g was added to a tetrahydrofuran 40 ml solution of methyl 2-hydroxy-2-methoxyacetate of 480 mg under nitrogen atmosphere, and benzylamine of 0.44 ml was further added thereto, followed by stirring at a room temperature for 1.5 hour. Insoluble matters were filtered off from the reaction solution, and trans-1-methoxy-3-trimethylsilyloxy-1,3-butadiene of 2.6 ml was added to the filtrate. Then, a 1.0M zinc chloride-ether solution of 4.0 ml was dropwise added, and the solution was stirred at a room temperature for 4 hours. A saturated sodium bicarbonate aqueous solution was added to the reaction solution, and it was extracted with ethyl acetate. The organic layer was washed with saturated brine and dried on anhydrous sodium sulfate. Then, the solvent was distilled off, and the resulting residue was separated and refined by means of silica gel column chromatography (ethyl acetate/ hexane=1/3 to 2/1), whereby the captioned compound of 422 mg was obtained in the form of a yellow oily substance.
(2) Production of 1-benzyl-4-hydroxy-2-hydroxymethylpiperidine A methanol-tetrahydrofuran (1:1) 6 ml solution of 1-benzyl-6-methoxycarbonyl-1,6-dihydro-4(5H)-pyridinone of 212 mg was cooled with ice under nitrogen atmosphere, and sodium borohydride of 342 mg was added thereto, followed by stirring at a room temperature for 14 hours. Lithium chloride of 175 mg was added to the reaction solution, and 6 hours later, lithium chloride of 125 mg was added, followed by further stirring for 3 days. The reaction solution was cooled with ice, and water was added thereto. Then, it was extracted with ethyl acetate. The organic layer was washed with saturated brine and dried on anhydrous sodium sulfate. Then, the solvent was distilled off to obtain the crude product of the captioned compound of 204 mg.

(3) Production of 1-benzyl-2-(tert-butyldimethylsilyloxymethyl)-4-hydroxypiperidine The crude product 204 mg of 1-benzyl-4-hydroxy-2-hydroxymethylpiperidine obtained above was dissolved in methylene chloride of 4 ml, and tert-butyldimethylsilyl chloride of 149 mg, triethylamine of 0.14 ml and 4-dimethylaminopyridine of 11 mg were added thereto, followed by stirring at a room temperature for 18 hours. Water was added to the reaction solution, and it was extracted with chloroform. The organic layer was washed with saturated brine and dried on anhydrous sodium sulfate. Then, the solvent was distilled off, and the resulting residue was separated and refined by means of silica gel column chromatography (ethyl acetate/hexane=1/2 to 2/1), whereby the captioned compound of 126 mg was obtained in the form of a colorless oily substance.

(4) Production of (2RS,4RS)- and (2RS,4SR)-4-azido-1-benzyl-2-(tert-butyldimethylsilyloxymethyl)piperidine A tetrahydrofuran 4 ml solution of 1-benzyl-2-(tert-butyl-dimethylsilyloxymethyl)-4-hydroxypiperidine of 123 mg was cooled with ice, and triphenylphosphine of 146 mg, diphenylphosphoryl azide of 0.12 mg and diisopropyl azocarboxylate of 0.12 ml were added in order thereto under nitrogen atmosphere, followed by stirring at a room temperature for one hour. The reaction solution was cooled with ice, and a saturated sodium bicarbonate aqueous solution and water were added thereto. Then, it was extracted with ethyl acetate. The organic layer was washed with saturated brine and dried on anhydrous sodium sulfate. Then, the solvent was distilled off, and the resulting residue was separated and refined by means of silica gel column chromatography (ethyl acetate/hexane=1/6), whereby obtained were the (2RS,4SR) body 40 mg of the captioned compound in the form of a colorless oily substance and the (2RS,4RS) body 85 mg of the captioned compound in the form of a yellow oily substance.

(5) Production of (2RS,4RS)-1-benzyl-2-(tert-butyldimethylsilyloxymethyl)-4-(2-nitrophenylamino) piperidine (2RS,4RS)-4-azido-1-benzyl-2-(tert-butyldimethylsilyloxymethyl)piperidine of 82 mg was dissolved in water-tetrahydrofuran (1:10) of 3 ml, and triphenylphosphine of 61 mg was added thereto, followed by stirring at 85° C. for 4 hours. The reaction solution was condensed, and the resulting residue was used to obtain the captioned compound by the same method as that of Example 35 (2).

(6) Production of 1-[(2RS,4RS)-1-benzyl-2-(tert-butyldimethylsilyloxymethyl)-4-piperidyl]-1,3-dihydro-2H-benzimidazol-2-one (2RS, 4RS)-1-benzyl-2-(tert-butyldimethylsilyloxymethyl)-4-(2-nitrophenylamino) piperidine was used to obtain the captioned compound by the same method as that of Example 35 (3).

(7) Production of 1-[(2RS,4RS)-2-(tert-butyldimethylsilyloxymethyl)-1-cyclooctylmethyl-4-piperidyl]-1,3-dihydro-2H-benzimidazol-2-one 1-[(2RS, 4RS)-1-benzyl-2-(tert-butyldimethylsilyloxymethyl)-4-piperidyl]-1,3-dihydro-2H-benzimidazol-2-one of 22 mg was dissolved in methanol of 20 mg, and 10% palladium-carbon was added thereto to react them at a hydrogen pressure of 4 kg/cm$^2$ for 22 hours. The reaction solution was filtered through celite, and a residue obtained by condensing the filtrate was used to obtain the captioned compound by the same method as that of Example 35 (5).

(8) Production of 1-[(2RS,4RS)-2-(tert-butyldimethylsilyloxymethyl)-1-cyclooctylmethyl-4-piperidyl]-3-ethyl-1,3-dihydro-2H-benzimidazol-2-one 1-[(2RS,4RS)-2-(tert-butyldimethylsilyloxymethyl)-1-cyclooctylmethyl-4-piperidyl]-1,3-dihydro-2H-benzimidazol-2-one and ethyl iodide were used to obtain the captioned compound by the same method as that of Example 13.

(9) Production of 1-[(2RS,4RS)-1-cyclooctylmethyl-2-hydroxymethyl-4-piperidyl]-3-ethyl-1,3-dihydro-2H-benzimidazol-2-one A 1.0M tetrabutylammonium fluoride-tetrahydrofuran solution 0.05 ml was added to a tetrahydrofuran 2 ml solution of 1-[(2RS,4RS)-2-(tert-butyldimethylsilyloxymethyl)-1-cyclooctylmethyl-4-piperidyl]-3-ethyl-1,3-dihydro-2H-benzimidazol-2-one of 2 mg, and the solution was stirred at a room temperature for one hour. A saturated sodium bicarbonate aqueous solution was added to the reaction solution, and it was extracted with chloroform. The organic layer was washed with saturated brine and dried on anhydrous sodium sulfate. Then, the solvent was distilled off, and the resulting residue was separated and refined by means of preparative thin layer chromatography [Kiselgel™60F$_{254}$, Art 5744 (manufactured by Merck Co., Ltd.); chloroform/methanol= 20/1], whereby the captioned compound of 1.3 mg was obtained in the form of a colorless solid.

$^1$H-NMR (CDCl$_3$) δ: 1.32(3H, t, J=7 Hz), 1.45–1.78(15H, brm), 1.82–1.92(1H, m), 1.92–2.12(1H, m), 2.80–2.90(1H, m), 2.95–3.10(2H, m), 3.18–3.44(2H, m), 3.60–3.69(2H, m), 3.78–3.98(4H, m), 4.27–4.46(1H, m), 7.01–7.17(4H, m)

FAB-MS (M+H)$^+$: 400

Example 50

Production of 1-[(3RS,4RS)-1-cyclooctylmethyl-3-methoxymethyl-4-piperidyl]-3-ethyl-1,3-dihydro-2H-benzimidazol-2-one 60% Sodium hydride of 4 mg was added to a dimethylformamide solution of 1-[(3RS,4RS)-1-cyclooctylmethyl-3-hydroxymethyl-4-piperidyl]-3-ethyl-1,3-dihydro-2H-benzimidazol-2-one of 28 mg, and the solution was stirred at a room temperature for 30 minutes. Then, methyl iodide of 45 μl was added thereto, and the solution was further stirred at a room temperature for 2 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/4), whereby the captioned compound of 4 mg was obtained in the form of a colorless solid.

$^1$H-NMR (CDCl$_3$) δ: 0.80–0.93(1H, m), 1.18–1.39(6H, m), 1.40–1.88(13H, m), 1.88–2.19(4H, m), 2.42–2.83(2H, m), 2.94–3.20(6H, m), 3.90–4.00(2H, m), 4.10–4.23(1H, m), 6.98–7.12(4H, m)

FAB-MS (M+H)$^+$: 414

Example 51

Production of 1-[(3RS,4RS)-3-benzyloxymethyl-1-cyclooctylmethyl-4-piperidyl]-3-ethyl-1,3-dihydro-2H-benzimidazol-2-one Benzyl bromide was used to obtain the captioned compound by the same method as that of Example 50.

$^1$H-NMR (CDCl$_3$) δ: 0.81–0.92(1H, m), 1.18–1.39(8H, m), 1.40–1.82(10H, m), 1.82–2.57(7H, m), 2.80–3.34(4H,

EXAMPLE 52
Production of 1-[(3RS,4RS)-1-cyclooctylmethyl-3-hydroxymethyl-4-piperidyl]-3-(2-dimethylaminoethyl)-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one and dimethylamino-ethyl chloride hydrochloride were used to obtain the captioned compound by the same methods as those of Example 13 and then Example 39.

$^1$H-NMR (CDCl$_3$) δ: 1.19–1.37(4H, m), 1.40–1.93(12H, m), 1.98–2.40(12H, m), 2.51–2.71(3H, m), 2.95–3.08(2H, m), 3.27–3.38(2H, m), 3.93–4.10(2H, m), 4.32–4.44(1H, m), 7.02–7.13(3H, m), 7.29–7.35 (1H, m)

FAB-MS (M+H)$^+$: 443

Optical resolution of 1-[(3RS,4RS)-1-cyclooctylmethyl-3-hydroxymethyl-4-piperidyl]-3-(2-dimethylaminoethyl)-1,3-dihydro-2H-benzimidazol-2-one was carried out using an optical resolution column (CHIRALPAK AD column manufactured by Daicel Co., Ltd.; 0.1% diethylamine, hexane/isopropyl alcohol=400/200), and obtained were a compound called a (3R*,4R*) body of the captioned compound for, $[α]_D^{20}$ –18.8° (c=1.000, CHCl$_3$) (in the form of dihydrochloride) for the sake of convenience from the former fraction and a compound called a (3S*,4S*) body of the captioned compound, $[α]_D^{20}$ +13.4° (c=1.000, CHCl$_3$) (in the form of dihydrochloride) for the sake of convenience from the latter fraction.

Example 53
Production of 1-[(3RS,4RS)-1-cyclooctylmethyl-3-hydroxymethyl-4-piperidyl]-3-isopropyl-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one and isopropyl bromide were used to obtain the captioned compound by the same methods as those of Example 13 and then Example 39.

$^1$H-NMR (CDCl$_3$) δ: 1.16–1.35(5H, m), 1.37–1.79(18H, m), 1.98–2.40(5H, m), 2.49–2.69(1H, m), 2.96–3.07(2H, m), 3.25–3.38(2H, m), 4.30–4.42(1H, m), 4.68–4.80(1H, m), 7.02–7.39(4H, m)

FAB-MS (M+H)$^+$: 414

Example 54
Production of 1-[(3RS,4RS)-1-cyclooctylmethyl-3-hydroxymethyl-4-piperidyl]-3-(2-methoxyethyl)-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one and methoxyethyl bromide were used to obtain the captioned compound by the same methods as those of Example 13 and then Example 39.

$^1$H-NMR (CDCl$_3$) δ: 1.18–1.33(5H, m), 1.38–1.92(12H, m), 1.95–2.25(6H, m), 2.98–3.14(2H, m), 3.24–3.39(5H, m), 3.68(2H, m), 4.05–4.13(2H, m), 4.31–4.47(1H, m), 7.02–7.17(3H, m), 7.29–7.40(1H, m)

FAB-MS (M+H)$^+$: 430

Example 55
Production of 1-[1-(1-methylcyclooctylmethyl)-4-piperidyl]-3-propargyl-1,3-dihydro-2H-benzimidazol-2-one 4-(2-Keto-1-benzimidazolinyl)piperidine and 1-methylcyclooctane-1-carbaldehyde were used to obtain the captioned compound by the same methods as those of Example 3 and then Example 13.

$^1$H-NMR (CDCl$_3$) δ: 0.89(3H, s), 1.28(3H, m), 1.40–1.75 (13H, m), 2.10(2H, s), 2.27(1H, t, J=2.7 Hz), 2.48(4H, m), 2.89(2H, m), 4.27(1H, m), 4.67(2H, d, J=2.7 Hz), 7.12(2H, m), 7.18(1H, m), 7.28(1H, m)

FAB-MS (M+H)$^+$: 394

Example 56
Production of 1-[1-(1-ethylcyclooctylmethyl)-4-piperidyl-3-propargyl-1,3-dihydro-2H-benzimidazol-2-one 1-(1-(1-Ethylcyclooctylmethyl)-4-piperidyl]-1,3-dihydro- 2H-benzimidazol-2-one obtained in Example 23 was used to obtain the captioned compound by the same method as that of Example 13.

$^1$H-NMR (CDCl$_3$) δ: 0.80(3H, t, J=7.8 Hz), 1.18–1.74 (18H, m), 2.09(2H, s), 2.27(1H, t, J=2.1 Hz), 2.41(4H, m), 2.88(2H, m), 4.28 (1H, m), 4.67(2H, d, J=2.1 Hz), 7.11(2H, m), 7.18(1H, m), 7.28(1H, m)

FAB-MS (M+H)$^+$: 408

Example 57
Production of 1-[1-(1-propylcyclooctylmethyl)-4-piperidyl]-3-propargyl-1,3-dihydro-2H-benzimidazol-2-one 4-(2-Keto-1-benzimidazolinyl)piperidine and 1-propylcyclooctane-1-carbaldehyde were used to obtain the captioned compound by the same methods as those of Example 3 and then Example 13.

$^1$H-NMR (CDCl$_3$) δ: 0.88(3H, t, J=6.9 Hz), 1.25(6H, m), 1.40–1.74(14H, m), 2.10(2H, s), 2.27(1H, t, J=2.7 Hz), 2.40(4H, m), 2.85(2H, m), 4.28(1H, m), 4.67(2H, d, J=2.7 Hz), 7.10(2H, m), 7.18(1H, m), 7.25(1H, m)

FAB-MS (M+H)$^+$: 422

Example 58
Production of 1-[(3RS,4RS)-1-cyclooctylmethyl-3-dimethylaminomethyl-4-piperidyl]-3-ethyl-1,3-dihydro-2H-benzimidazol-2-one (1) Production of 1-[(3RS,4RS)-1-cyclooctylmethyl-3-formyl-4-piperidyl]-3-ethyl-1,3-dihydro-2H-benzimidazol-2-one A dimethyl sulfoxide 10 ml solution of a sulfur trioxide pyridine complex of 570 mg was added to a dimethyl sulfoxide 10 ml solution of 1-[(3RS,4RS)-1-cyclooctylmethyl-3-hydroxymethyl-4-piperidyl]-3-ethyl-1, 3-dihydro-2H-benzimidazol-2-one of 480 mg obtained in Example 42 and triethylamine of 1.0 ml at a room temperature, and the solution was stirred at a room temperature for 2 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/3), whereby the captioned compound of 253 mg was obtained.

(2) Production of 1-[(3RS,4RS)-1-cyclooctylmethyl-3-dimethyl-aminomethyl-4-piperidyl]-3-ethyl-1,3-dihydro-2H-benzimidazol-2-one A tetrahydrofuran solution of 1-[(3RS,4RS)-1-cyclooctylmethyl-3-formyl-4-piperidyl]-3-ethyl-1,3-dihydro-2H-benzimidazol-2-one and dimethylamine was used to obtain the captioned compound by the same method as that of Example 3.

$^1$H-NMR (CDCl$_3$) δ: 0.85–0.94(3H, m), 1.18–1.38(5H, m), 1.39–1.80(13H, m), 1.96–2.25(10H, m), 2.37–2.73(2H, m), 2.94–3.27 (2H, m), 3.90–4.13(3H, m), 6.98–7.30(4H, m)

FAB-MS (M+H)$^+$: 427

Example 59
Production of 1-[(3RS,4RS)-1-cyclooctylmethyl-3-methylaminomethyl-4-piperidyl]-3-ethyl-1,3-dihydro-2H-benzimidazol-2-one 1-[(3RS,4RS)-1-cyclooctylmethyl-3-formyl-4-piperidyl]-3-ethyl-1,3-dihydro-2H-benzimidazol-2-one obtained in Example 58 and methylamine hydrochloride were used to obtain the captioned compound by the same method as that of Example 3.

$^1$H-NMR (CDCl$_3$) δ: 1.16–1.38(6H, m), 1.38–1.90(13H, m), 1.92–2.67(12H, m), 2.94–3.20(2H, m), 3.93(2H, m), 4.10–4.23(1H, m), 6.97–7.12(3H, m), 7.24–7.31(1H, m)

FAB-MS (M+H)$^+$: 413

Example 60

Production of 1-[(3S*,4S*)-3-aminomethyl-1-cyclooctylmethyl-4-piperidyl]-3-ethyl-13-dihydro-2H-breaenzimidazol-2-one (1) Production of 1-[(3S*,4S*)-3-azidomethyl-1-cyclooctylmethyl-4-piperidyl]-3-ethyl-1,3-dihydro-2H-benzimidazol-2-one Triethylamine of 86 μl and then methanesulfonyl chloride of 30 μl were added to an ethyl acetate 7 ml solution of 1-[(3S*,4S*)-1-cyclooctylmethyl-3-hydroxymethyl-4-piperidyl]-3-ethyl-1,3-dihydro-2H-benzimidazol-2-one of 99 mg obtained in Example 42 at a room temperature, followed by stirring at a room temperature for 30 minutes. Insoluble matters contained in the reaction solution were filtered off, and the solvent was distilled off. The resulting residue was dissolved in dimethylformamide of 2.5 ml, and sodium azide of 48 ml was added thereto, followed by stirring at 80° C. for one hour. The reaction solution was cooled down to a room temperature and diluted with ethyl acetate. It was washed with water and saturated brine and dried on anhydrous sodium sulfate. Then, the solvent was distilled off, and the resulting residue was separated and refined by means of silica gel column chromatography (ethyl acetate/hexane=1/1), whereby the captioned compound of 75 mg was obtained in the form of a colorless solid.

(2) Production of 1-[(3S*,4S*)-3-aminomethyl-1-cyclooctylmethyl-4-piperidyl]-3-ethyl-1,3-dihydro-2H-benzimidazol-2-one [(3S*,4S*)-3-azidomethyl-1-cyclooctylmethyl-4-piperidyl]-3-ethyl-1,3-dihydro-2H-benzimidazol-2-one of 350 mg was dissolved in methanol of 35 ml, and 20% palladium hydroxide of 150 mg and 10% hydrogen chloride-methanol of 5 ml were added thereto, followed by stirring at an atmospheric pressure and a room temperature for 15 hours under hydrogen atmosphere. The reaction solution was filtered through celite, and the filtrate was condensed. Subsequently, the resulting residue was dissolved in ethyl acetate and washed with a 1N sodium hydroxide aqueous solution and saturated brine, followed by drying on anhydrous sodium sulfate. Then, the solvent was distilled off, and the resulting residue was separated and refined by means of silica gel column chromatography (chloroform/methanol=50/1), whereby the captioned compound of 223 mg was obtained.

$^1$H-NMR (CDCl$_3$) δ: 0.80–0.97(3H, m), 1.86–1.36(8H, m), 1.42–1.88(8H, m), 1.88–2.32(7H, m), 2.42–2.58(3H, m), 3.03–3.16(2H, m), 3.91–3.99(2H, m), 4.26–4.31(1H, m), 6.99–7.12(3H, m), 7.30–7.34 (1H, m)

FAB-MS (M+H)$^+$: 399

$[α]_D^{20}$ +10.8° (c=0.5, CHCl$_3$)

Example 61

Production of 3-(2-aminoethyl)-1-(1-cyclooctylmethyl-4-piperidyl)-1,3-dihydro-2H-benzimidazol-2-one 60% Sodium hydride of 64 mg was added to a dimethylformamide 8 ml solution of 1-(1-cyclooctylmethyl-4-piperidyl)-1,3-dihydro-2H-benzimidazol-2-one of 360 mg obtained in Example 6, and the solution was stirred at a room temperature for one hour. Then, bis(tert-butoxycarbonyl)aminoethyl bromide of 515 mg was added thereto, and the solution was further stirred at 80° C. for 15 hours. The reaction solution was allowed to come down to a room temperature and diluted with ethyl acetate. It was washed with water and saturated brine and dried on anhydrous sodium sulfate. Then, the solvent was distilled off, and the resulting residue was dissolved in 10% hydrogen chloride-methanol, followed by stirring at a room temperature for one hour. The reaction solution was condensed and then diluted with ethyl acetate. It was washed with a 2N sodium hydroxide aqueous solution and saturated brine and dried on anhydrous sodium sulfate. Then, the solvent was distilled off, and the resulting residue was separated and refined by means of silica gel column chromatography (chloroform/methanol=40/1), whereby the captioned compound of 307 mg was obtained in the form of a white solid.

$^1$H-NMR (CDCl$_3$) δ: 1.18–2.03(19H, m), 2.10–2.20(4H, m), 2.48(2H, m), 3.02–3.14(4H, m), 3.96(2H, t, J=6.3 Hz), 4.38(1H, m), 7.08(3H, m), 7.32(1H, m)

FAB-MS (M+H)$^+$: 385

Example 62

Production of 1-(1-cyclooctylmethyl-4-piperidyl)-1,3-dihydro-imidazo[4,5-c]pyridin-2-one 4-Chloro-3-nitropyridine and 4-amino-1-cyclooctylmethyl-piperidine were used to obtain the captioned compound by the same method as that of Example 23.

$^1$H-NMR (CDCl$_3$) δ: 1.26(2H, m), 1.42–1.86(15H, m), 2.10(4H, m), 2.36(2H, m), 3.02(2H, m), 4.32(1H, m), 7.22 (1H, m), 8.30(1H, m), 8.36(1H, s), 8.48(1H, brs)

FAB-MS (M+H)$^+$: 343

Example 63

Production of 1-[(3RS 4RS)-1-cyclooctylmethyl-3-(2-ethoxycarbonylethyl)-4-piperidyl]-3-ethyl-1,3-dihydro-2H-benzimidazol-2-one Triethyl phosphonoacetate of 45 tl and then 60% sodium hydride of 9 mg were added to a tetrahydrofuran 1.5 ml solution of 1-[(3RS,4RS)-1-cyclooctylmethyl-3-formyl-4-piperidyl]-3-ethyl-1,3-dihydro-2H-benzimidazol-2-one of 60 mg obtained in Example 58 (1) while cooling with ice, and the solution was stirred for one hour while cooling with ice. The reaction solution was allowed to come up to a room temperature and diluted with ethyl acetate. It was washed with a 1N sodium hydrogensulfate aqueous solution and saturated brine and dried on anhydrous sodium sulfate. Then, the solvent was distilled off, and the resulting residue was dissolved in methanol 5 ml. 10% Palladium-carbon of 50 mg was added thereto, and the solution was stirred at an atmospheric pressure and a room temperature for 12 hours under hydrogen atmosphere. The reaction soltion was filtered through celite, and then the filtrate was condensed. The resulting residue was separated and refined by means of silica gel column chromatography (chloroform/methanol=30/1), whereby the captioned compound of 26 mg was obtained in the form of a white solid.

$^1$H-NMR (CDCl$_3$) δ: 1.13(3H, m), 1.18–1.28(3H, m), 1.34(3H, m), 1.40–1.81(17H, m), 2.02–2.58(6H, m), 2.95–3.07(2H, m), 3.87–4.19(5H, m), 6.93–7.13(3H, m), 7.18–7.24(1H, m)

FAB-MS (M+H)$^+$: 470

Example 64

Production of 1-[(3RS,4RS)-1-cyclooctylmethyl-3-(3-hydroxnpropyl)-4-piperidyl]-3-ethyl-1,3-dihydro-2H-benzimidazol-2-one 1-[(3RS,4RS)-1-cyclooctylmethyl-3-(2-ethoxycarbonyl-ethyl)-4-piperidyl]-3-ethyl-1,3-dihydro-2H-benzimidazol- 2-one obtained in Example 63 was used to obtain the captioned compound by the same method as that of Example 39.

$^1$H-NMR (CDCl$_3$) δ: 1.08–1.40(10H, m), 1.40–1.92(15H, m), 1.96–2.25(3H, m), 2.25–2.62(2H, m), 2.97–3.12(2H, m), 3.40–3.52(2H, m), 3.89–4.21(3H, m), 6.98–7.13(3H, m), 7.20–7.30(1H, m)

FAB-MS (M+H)$^+$: 428

Example 65

Production of 1-[(3RS,4RS)-1-cyclooctylmethyl-3-ethyl-4-piperidyl]-3-ethyl-1,3-dihydro-2H-benzimidazol-2-one Potassium tert-butoxide of 127 mg was added to a tetrahydrofuran 7 ml solution of methyltriphenylphosphonium bromide of 400 mg while cooling with ice, and the solution was stirred for 30 minutes. Then, a tetrahydrofuran 8 ml solution of 1-[(3RS,4RS)-1-cyclooctylmethyl-3-formyl-4-piperidyl]-3-ethyl-1,3-dihydro-2H-benzimidazol-2-one of 60 mg obtained in Example 58 (1) was added thereto, and the solution was further stirred for 30 minutes while cooling with ice. The reaction solution was diluted with ethyl acetate and washed with water and saturated brine, followed by drying on anhydrous sodium sulfate. Then, the solvent was distilled off, and the resulting residue was dissolved in methanol 10 ml. 10% Palladium-carbon was added thereto, and the solution was stirred at an atmospheric pressure and a room temperature for 12 hours under hydrogen atmosphere. The reaction solution was filtered through celite, and then the filtrate was condensed. The resulting residue was separated and refined by means of silica gel column chromatography (chloroform/methanol=30/1), whereby the captioned compound of 65 mg was obtained in the form of a white solid.

$^1$H-NMR (CDCl$_3$) δ: 0.75(3H, m), 0.96–1.17(1H, m), 1.17–1.49(7H, m), 1.50–1.89(14H, m), 1.98–2.20(3H, m), 2.24–2.50(2H, m), 2.95–3.12(2H, m), 3.90–4.18(3H, m), 6.97–7.11(3H, m), 7.21–7.30(1H, m)

FAB-MS (M+H)$^+$: 398

Example 66

Production of 1-[(3RS,4RS)-1-(1-ethylcyclooctylmethyl)-3-hydroxymethyl-4-piperidyl]-1,3-dihydro-2H-benzimidazol-2-one (1) Production of 1-[(3RS,4RS)-3-ethoxycarbonyl-1-(1-ethylcyclooctylmethyl)-4-piperidyl]-1,3-dihydro-2H-benzimidazol-2-one 1-[(3RS,4RS)-3-ethoxycarbonyl-4-piperidyl]-1,3-dihydro-2H-benzimidazol-2-one and 1-ethylcyclooctane-1-carbaldehyde were used to obtain the captioned compound by the same method as that of Example 3.

(2) Production of 1-[(3RS,4RS)-1-(1-ethylcyclooctylmethyl)-3-hydroxymethyl-4-piperidyl]-1,3-dihydro-2H-benzimidazol-2-one The captioned compound was obtained by the same method as that of Example 39.

$^1$H-NMR (CDCl$_3$) δ: 0.83(3H, t, J=6.6 Hz), 1.14–1.20 (4H, m), 1.20–1.86(13H, m), 2.30–2.65(6H, m), 2.92(2H, m), 3.38(2H, brs), 4.34(1H, m), 7.11(3H, m), 7.28(1H, m), 9.14(1H, brs)

FAB-MS (M+H)$^+$: 400

Example 67

Production of 1-[(3RS, 4RS)-1-(1-ethylcyclooctylmethyl)-3-hydroxymethyl-4-piperidyl]-3-propargyl-1,3-dihydro-2H-benzimidazol-2-one (1) Production of 1-[(3RS,4RS)-3-ethoxycarbonyl-1-(1-ethylcyclooctylmethyl)-4-piperidyl]-3-propargyl-1,3-dihydro-2H-benzimidazol-2-one 1-[(3RS,4RS)-3-ethoxycarbonyl-1-(1-ethylcyclooctylmethly)- 4-piperidyl]-1,3-dihydro-2H-benzimidazol-2-one obtained in Example 66 (1) was used to obtain the captioned compound by the same method as that of Example 13.

(2) Production of 1-[(3RS,4RS)-1-(1-ethylcyclooctylmethyl)-3-hydroxymethyl-4-piperidyl]-3-propargyl-1,3-dihydro-2H-benzimidazol-2-one 1-[(3RS,4RS)-3-ethoxycarbonyl-1-(1-ethylcyclooctylmethyl)-4-piperidyl]-3-propargyl-1,3-dihydro-2H-benzimidazol-2-one was used to obtain the captioned compound by the same method as that of Example 39.

$^1$H-NMR (CDCl$_3$) δ: 0.81(3H, t, J=7.2 Hz), 1.20–1.70 (18H, m), 1.78(1H, m), 2.30(1H, t, J=2.4 Hz), 2.32–2.64(4H, m), 2.89(2H, m), 3.33(2H, brs), 4.32(1H, m), 4.70(2H, m), 7.13(2H, m), 7.20(1H, m), 7.29(1H, m)

FAB-MS (M+H)$^+$: 438

Example 68

Production of 3-(2-aminoethyl)-1-[(3S*,4S*)-1-cyclooctylmethyl-3-hydroxymethyl-4-piperidyl]-1,3-dihydro-2H-benzimidazol-2-one (1) Production of 3-[2-[bis(tert-butoxycarbonyl)amino] ethyl]-1-[(3S*,4S*)-1-cyclooctylmethyl-3-ethoxycarbonyl-4-piperidyl]-1,3-dihydro-2H-benzimidazol-2-one and 3-[2-[bis(tert-butoxycarbonyl)-amino]ethyl]-1-[(3R*,4R*)-1-cyclooctylmethyl-3-ethoxycarbonyl-4-piperidyl]-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one obtained in Example 37 was used to obtain 3-[2-[bis(tert-butoxycarbonyl)amino]ethyl]-1-[(3RS,4RS)-1-cyclooctylmethyl-3-ethoxycarbonyl-4-piperidyl]-1,3-dihydro-2H-benzimidazol-2-one by the same method as that of Example 61.

Optical resolution of the compound obtained above was carried out using an optical resolution column (CHIRALPAK AD column manufactured by Daicel Co., Ltd.; 0.1% diethylamine, hexane/isopropyl alcohol=800/200) to obtain a compound called a (3S*,4S*) body of the captioned compound for the sake of convenience from the former fraction and a compound called a (3R*,4R*) body of the captioned compound for the sake of convenience from the latter fraction.

(2) Production of 3-(2-aminoethyl)-1-[(3S*,4S*)-1-cyclooctylmethyl-3-hydroxymethyl-4-piperidyl]-1,3-dihydro-2H-benzimidazol-2-one 3-[2-[bis(tert-butoxycarbonyl)amino]ethyl]-1-[(3S*,4S*)-1-cyclooctylmethyl-3-ethoxycarbonyl-4-piperidyl]-1,3-dihydro-2H-benzimidazol-2-one was deblocked with 10% hydrogen chloride-methanol, and then the captioned compound was obtained by the same method as that of Example 39.

$^1$H-NMR (CDCl$_3$) δ: 1.28(3H, m), 1.40–2.32(17H, m), 2.45(1H, m), 2.69(1H, m), 3.08(4H, m), 3.34(2H, m), 4.00 (2H, m), 4.39(1H, m), 7.08(3H, m), 7.38(1H, m)

FAB-MS (M+H)+: 415

$[\alpha]_D^{20}$+2.40° (c=0.500, DMSO) (in the form of dihydrochloride)

Example 69

Production of 1-[1-(bicyclo[4.4.01dec-2-ylmethyl)-4-piperidyl]-3-propargyl-1,3-dihydro-2H-benzimidazol-2-one 1-[1-(Bicyclo[4.4.0]dec-2-ylmethyl)-4-piperidyl]-1,3-dihydro-2H-benzimidazol-2-one obtained in Example 10 was used to obtain the captioned compound by the same method as that of Example 13.

$^1$H-NMR (CDCl$_3$) δ: 0.80–1.02(3H, m), 1.12–1.34(5H, m), 1.46(2H, m), 1.54–2.10(11H, m), 2.22(2H, m), 2.28(1H, t, J=2.4 Hz), 2.45(2H, m), 2.90–3.11(2H, m), 4.34(1H, m), 4.68(2H, d, J=2.4 Hz), 7.10(2H, m), 7.18(1H, m), 7.29(1H, m)

FAB-MS (M+H)$^+$: 406

Example 70

Production of 3-benzyl-1-[1-(bicyclo[4.4.0]dec-2-ylmethyl)-4-piperidyl]-1,3-dihydro-2H-benzimidazol-2-one 1-[1-(Bicyclo[4.4.0]dec-2-ylmethyl)-4-piperidyl]-1,3-dihydro-2H-benzimidazol-2-one obtained in Example 10 and benzyl bromide were used to obtain the captioned compound by the same method as that of Example 13.

$^1$H-NMR (CDCl$_3$) δ: 0.83–1.01(2H, m), 1.10–1.84(16H, m), 1.88–2.06(2H, m), 2.20–2.28(2H, m), 2.45(3H, m), 2.95(1H, m), 3.05(1H, m), 4.39(1H, m), 5.07(2H, s), 6.88 (1H, m), 7.01(2H, m), 7.30(6H, m)

FAB-MS (M+H)$^+$: 458

Example 71

Production of 3-ethyl-1-[1-(1-ethylcyclooctylmethyl)-4-piperidyl]-1,3-dihydro-2H-benzimidazol-2-one 1-[1-(1-Ethylcyclooctylmethyl)-4-piperidyl]-1,3-dihydro-2H-benzimidazol-2-one obtained in Example 23 and ethyl iodide were used to obtain the captioned compound by the same method as that of Example 13.

$^1$H-NMR (CDCl$_3$) δ: 0.80(3H, t, J=7.5 Hz), 1.24(2H, m), 1.34(3H, t, J=7.2 Hz), 1.36(2H, q, J=7.5 Hz), 1.40–1.72 (14H, m), 2.09(2H, s), 2.41(4H, m), 2.88(2H, m), 3.94(2H, q, J=7.2 Hz), 4.30(1H, m), 7.01(1H, m), 7.07(2H, m), 7.24(1H, m)

FAB-MS (M+H)$^+$: 398

Example 72

Production of 1-[(3RS,4RS)-1-cyclooctylmethyl-3-(2-hydroxyethyl)-4-piperidyl]-3-ethyl-1,3-dihydro-2H-benzimidazol-2-one Potassium tert-butoxide of 127 mg was added to a tetrahydrofuran 7 ml solution of methyltriphenylphosphonium bromide of 400 mg while cooling with ice, and the solution was stirred for 30 minutes. Then, added thereto was a tetrahydrofuran 8 ml solution of 1-[(3RS,4RS)-1-cyclooctylmethyl-3-formyl-4-piperidyl]-3-ethyl-1,3-dihydro-2H-benzimidazol-2-one of 157 mg obtained in Example 58 (1), and the solution was further stirred for 30 minutes while cooling with ice. The reaction solution was diluted with ethyl acetate and washed with water and saturated brine, followed by drying on anhydrous sodium sulfate. Then, the solvent was distilled off, and the resulting residue was dissolved in tetrahydrofuran of 3 ml. 9-Borabicyclo[3.3.]nonane of 173 mg was added thereto while cooling with ice, and the solution was stirred for one hour. Water of 100 μl, a 3N sodium hydroxide aqueous solution of 3 ml and a 30% hydrogen peroxide aqueous solution of 3 ml were added thereto, and the solution was further stirred at a room temperature for 6 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=20/1), whereby the captioned compound of 57 mg was obtained in the form of a colorless solid.

$^1$H-NMR (CDCl$_3$) δ: 0.80–0.92(1H, m), 1.15–1.38(6H, m), 1.40–1.95(14H, m), 2.03–2.21(4H, m), 2.29–2.78(2H, m), 2.97–3.16(2H, m), 3.51(2H, t, J=6.6 Hz), 3.75–3.84(1H, m), 3.88–4.00(2H, m), 4.02–4.21(1H, m), 6.99–7.12(3H, m), 7.23–7.34(1H, m)

FAB-MS (M+H)$^+$: 414

Example 73

Production of 3-cyclopropylmethyl-1-1-(1-ethylcyclooctylmethyl)-4-piperidyl]-1,3-dihydro-2H-benzimidazol-2-one 1-[1-(1-Ethylcyclooctylmethyl)-4-piperidyl]-1,3-dihydro-2H-benzimidazol-2-one obtained in Example 23 and cyclopropylmethyl bromide were used to obtain the captioned compound by the same method as that of Example 13.

$^1$H-NMR (CDCl$_3$) δ: 0.43(2H, m), 0.54(2H, m), 0.80(3H, t, J=7.5 Hz), 1.24(2H, m), 1.36(2H, q, J=7.5 Hz), 1.40-1.73 (14H, m), 2.09(2H, s), 2.41(4H, m), 2.88(2H, m), 3.75(2H, d, J=6.9 Hz), 4.30(1H, m), 7.06(3H, m), 7.25(1H, m)

FAB-MS (M+H)$^+$: 424

Example 74

Production of 1-[1-(1-ethylcyclooctylmethyl)-4-piperidyl]-3-(2-hydroxyethyl)-1,3-dihydro-2H-benzimidazol-2-one 60% Sodium hydride of 5.5 mg was added to a dimethylformamide 1.5 ml solution of 1-[1-(1-ethylcyclooctylmethyl)-4-piperidyl]-1,3-dihydro-2H-benzimidazol-2-one of 25 mg obtained in Example 23 at a room temperature, and the solution was stirred for 30 minutes. A dimethylformamide 0.5 ml solution of 2-trimethylsilyloxyethyl bromide of 60 mg was added to the reaction solution, and the solution was further stirred for 10 hours. The reaction solution was diluted with ethyl acetate and washed with water and saturated brine, followed by drying on anhydrous sodium sulfate. Then, the solvent was distilled off, and the resulting residue was dissolved in chloroform 1 ml. A 1M tetrabutylammonium fluoride-tetrahydrofuran solution of 1.0 ml was added thereto, and the solution was stirred at a room temperature for 1.5 hour. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/1), whereby the captioned compound of 7 mg was obtained in the form of a white solid.

$^1$H-NMR (CDCl$_3$) δ: 0.80(3H, t, J=7.5 Hz), 1.24(2H, m), 1.36(2H, q, J=7.5 Hz), 1.40–1.74(14H, m), 2.09(2H, s), 2.40(4H, m), 2.89(2H, m), 3.98(2H, m), 4.04(2H, m), 4.30 (1H, m), 7.08(3H, m), 7.27(1H, m)

FAB-MS (M+H)$^+$: 414

Example 75

Production of 1-[(3RS,4RS)-1-cyclooctylmethyl-3-(1,2-dihydroxyethyl)-4-piperidyl]-3-ethyl-1,3-dihydro-2H-benzimidazol-2-one Potassium tert-butoxide of 127 mg was added to a tetrahydrofuran 7 ml solution of methyltriphenylphosphonium bromide of 400 mg while cooling with ice, and the solution was stirred for 30 minutes. Then, added thereto was a tetrahydrofuran 8 ml solution of 1-[(3RS,4RS)-1-cyclooctylmethyl-3-formyl-4-piperidyl]-3-ethyl-1,3-dihydro-2H-benzimidazol-2-one of 157 mg obtained in Example 58 (1), and the solution was further stirred for 30 minutes while cooling with ice. The reaction solution was diluted with ethyl acetate and =washed with water and saturated brine, followed by drying on anhydrous sodium sulfate. Then, the solvent was distilled off, and the resulting residue was dissolved in a mixed solvent of acetonitrile of 4 ml and water of 2 ml. N-methylmorpholine-N-oxide of 83 mg and then osmium tetraoxide (5 mg/ml tert-butanol solution) of 3 ml were added thereto while cooling with ice, and the solution was stirred for 12 hours while heating gradually to a room temperature. The reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=20/1), whereby the captioned compound of 43 mg was obtained in the form of a colorless solid.

$^1$H-NMR (CDCl$_3$) δ: 0.83–0.93(1H, m), 1.20–1.39(6H, m), 1.40–2.20(18H, m), 2.20–2.39(1H, m), 2.42–2.80(2H, m), 2.95–3.11(2H, m), 3.27–3.39(1H, m), 3.49–3.56(1H, m), 3.90–3.99(2H, m), 4.23–4.48 (1H, m), 7.01–7.22(3H, m), 7.27–7.35(1H, m)

FAB-MS (M+H)$^+$: 430

Example 76

Production of 3-(2-aminoethyl)-1-[1-(1-ethylcyclooctylmethyl)-4-piperidyl]-1,3-dihydro-2H-benzimidazol-2-one 1-[1-(1-Ethylcyclooctylmethyl)-4-piperidyl]-1,3-dihydro-2H-benzimidazol-2-one obtained in Example 23 was used to obtain the captioned compound by the same method as that of Example 61.

$^1$H-NMR (CDCl$_3$) δ: 0.81(3H, t, J=7.5 Hz), 1.25(2H, m), 1.37(2H, q, J=7.5 Hz), 1.42–1.75(14H, m), 2.11(2H, s), 2.42(4H, m), 2.90(2H, m), 3.12(2H, t, J=6.0 Hz), 3.63(2H, br), 3.99(2H, t, J=6.0 Hz), 4.29(1H, m), 7.08(4H, m)

FAB-MS (M+H)$^+$: 413

Example 77

Production of 1-[(3RS,4RS)-3-carboxyl-1-cyclooctylmethyl-4-piperidyl]-1,3-dihydro-2H-benzimidazol-2-one A 2N sodium hydroxide aqueous solution of 0.5 ml was added to a tetrahydrofuran 2 ml solution of 1-[(3RS,4RS)-1-cyclooctylmethyl-3-ethoxycarbonyl-4-piperidyl]-1,3-dihydro-2H-benzimiazol-2-one of 50 mg obtained in Example 37 at a room temperature, and the solution was stirred for 2 days. The reaction solution was condensed, and the resulting residue was separated and refined by means of silica gel column chromatography (chloroform/methanol=10/1), whereby the captioned compound of 32 mg was obtained in the form of a white solid.

$^1$H-NMR (DMSO-d$_6$) δ: 1.20(2H, m), 1.35–1.75(14H, m), 2.02–2.15(4H, m), 2.29(1H, m), 2.89(1H, m), 3.08(1H, m), 3.45(2H, m), 4.20(1H, m), 6.95(3H, m), 7.15(1H, m), 10.75(1H, br)

FAB-MS (M+H)$^+$: 386

Example 78

Production of 1-[(3RS,4RS)-3-carbamoyl-1-cyclooctylmethyl-4-piperidyl]-1,3-dihydro-2H-benzimidazol-2-one 1-[(3RS,4RS)-3-carboxyl-1-cyclooctylmethyl-4-piperidyl]-1,3-dihydro-2H-benzimidazol-2-one of 10 mg obtained in Example 77 was dissolved in thionyl chloride of 0.5 ml, and the solution was stirred at a room temperature for one hour. The reaction solution was condensed, and the resulting residue was separated and refined by means of silica gel column chromatography (chloroform/methanol=10/1), whereby the captioned compound of 5 mg was obtained in the form of a white solid.

$^1$H-NMR (CDCl$_3$) δ: 1.24(2H, m), 1.35–1.90(12H, m), 2.10–2.55(6H, m), 3.04(1H, m), 3.18(1H, m), 3.54–3.78(2H, m), 4.32 (1H, m), 5.75(1H, br), 6.16(1H, br), 7.03(3H, m), 7.16(1H, m), 9.24 (1H, br)

FAB-MS (M+H)$^+$: 385

Example 79

Production of 1-(1-cyclooctylmethyl-4-piperidyl)-3-[2-(methylamino)ethyl]-1,3-dihydro-2H-benzimidazol-2-one (1) Production of 1-(1-cyclooctylmethyl-4-piperidyl)-3-[2-(trifluoroacetylamino)ethyl]-1,3-dihydro-2H-benzimidazol-2-one Trifluoroacetic anhydride of 0.5 ml was added to a pyridine 2 ml solution of 3-(2-aminoethyl)-1-(1-cyclooctylmethyl-4-piperidyl)-1,3-dihydro-2H-benzimidazol-2-one of 65 mg obtained in Example 61, and the solution was stirred at a room temperature for 12 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=100/1), whereby the captioned compound of 33 mg was obtained.

(2) Production of 1-(1-cyclooctylmethyl-4-piperidyl)-3-[2-(methylamino)ethyl]-1,3-dihydro-2H-benzimidazol-2-one 60% Sodium hydride of 6 mg was added to a dimethylformamide 2 ml solution of 1-(1-cyclooctylmethyl-4-piperidyl)-3-[2-(trifluoroacetylamino)ethyl]-1,3-dihydro-2H-benzimidazol-2-one of 33 mg, and the solution was stirred at a room temperature for 30 minutes. Then, methyl iodide of 20 μl was added thereto, and the solution was further stirred at a room temperature for one hour. The reaction solution was diluted with ethyl acetate and washed with water and saturated brine, followed by drying on anhydrous sodium sulfate. Then, the solvent was distilled off, and the resulting residue was dissolved in water-methanol (1/10) of 2 ml. Potassium carbonate of 30 mg was added thereto, and the solution was stirred at a room temperature for 6 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=20/1), whereby the captioned compound of 3 mg was obtained in the form of a colorless solid.

$^1$H-NMR (CDCl$_3$) δ: 1.25(2H, m), 1.40–1.93(15H, m), 2.08–2.18(4H, m), 2.45(2H, m), 2.50(3H, s), 3.04(4H, m), 4.04(2H, t, J=6.3 Hz), 4.37(1H, m), 7.06(3H, m), 7.30(1H, m)

FAB-MS (M+H)$^+$: 399

Example 80

Production of 1-[(3RS,4RS)-1-cyclooctylmethyl-3-(2-dimethylaminoethyl)-4-piperidyl]-3-ethyl-1,3-dihydro-2H-benzimidazol-2-one (1) Production of 1-[(3RS,4RS)-1-cyclooctylmethyl-3-formylmethyl-4-piperidyl]-3-ethyl-1,3-dihydro-2H-benzimidazol-2-one A dimethyl sulfoxide 0.5 ml solution of triethylamine of 72 μl and a sulfur trioxide -pyridine complex of 41 mg was added to a dimethyl sulfoxide 1 ml solution of 1-[(3RS,4RS)-1-cyclooctylmethyl-3-(2-hydroxyethyl)-4-piperidyl]-3-ethyl-1,3-dihydro-2H-benzimidazol-2-one of 35 mg obtained in Example 72, and the solution was stirred at a room temperature for 3 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/3), whereby the captioned compound of 6 mg was obtained.

(2) Production of 1-[(3RS,4RS)-1-cyclooctylmethyl-3-(2-dimethylaminoethyl)-4-piperidyl]-3-ethyl-1,3-dihydro-2H-benzimidazol-2-one 1-[(3RS,4RS)-1-cyclooctylmethyl-3-formylmethyl-4-piperidyl]-3-ethyl-1,3-dihydro-2H- benzimidazol-2-one and a 2M dimethylamine-tetrahydrofuran solution were used to obtain the captioned compound by the same method as that of Example 3.

$^1$H-NMR (CDCl$_3$) δ: 0.80–0.93(2H, m), 1.15–1.86(23H, m), 1.91–2.28(9H, m), 2.32–2.61(1H, m), 2.97–3.09(2H, m), 3.89–4.18(3H, m), 6.97–7.12(3H, m), 7.20–7.31(1H, m)

FAB-MS (M+H)$^+$: 441

Example 81

Production of 1-[(3RS,4RS)-1-cyclooctylmethyl-3-(3-dimethylaminopropyl)-4-piperidyl]-3-ethyl-1,3-dihydro-2H-benzimidazol-2-one (1) Production of 1-[(3RS,4RS)-1-cyclooctylmethyl-3-(2-formylethyl)-4-piperidyl]-3-ethyl-1,3-dihydro-2H-benzimidazol-2-one 1-[(3RS,4RS)-1-cyclooctylmethyl-3-(3-hydroxypropyl)-4-piperidyl]-3-ethyl-1,3-dihydro-2H-benzimidazol-2-one obtained in Example 64 was used to obtain the captioned compound by the same method as that of Example 80 (1).

(2) Production of 1-[(3RS,4RS)-1-cyclooctylmethyl-3-(3-dimethylaminopropyl)-4-piperidyl]-3-ethyl-1,3-dihydro-2H-benzimidazol-2-one 1-[(3RS,4RS)-1-cyclooctylmethyl-3-(2-formylethyl)-4-piperidyl]-3-ethyl-1,3-dihydro-2H-benzimidazol-2-one and a 2M dimethylamine-tetrahydrofuran solution were used to obtain the captioned compound by the same method as that of Example 3.

$^1$H-NMR (CDCl$_3$) δ: 0.82–0.91(2H, m), 1.01–1.38(11H, m), 1.38–1.83(13H, m), 1.90–2.20(10H, m), 2.35–2.53(1H, m), 2.95–3.10 (2H, m), 3.89–4.15(3H, m), 7.00–7.12(3H, m), 7.22–7.28(1H, m)

FAB-MS (M+H)$^+$: 455

Example 82

Production of 1-[(3RS,4RS)-1-cyclooctylmethyl-3-hydroxymethyl-4-piperidyl]-3-propargyl-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one obtained in Example 37 was used to obtain the captioned compound by the same methods as those of Example 13 and then Example 39.

$^1$H-NMR (CDCl$_3$) δ: 1.24(2H, m), 1.38–1.91(14H, m), 2.00–2.23(6H, m), 2.29(1H, t, J=2.1 Hz), 2.59(1H, m), 3.02(2H, m), 3.36(2H, m), 4.38(1H, m), 4.69(2H, m), 7.12 (2H, m), 7.22(1H, m), 7.31(1H, m)

FAB-MS (M+H)$^+$: 410

Example 83

Production of 1-[(3RS,4RS)-1-cyclooctylmethyl-3-(1-hydroxyethyl)-4-piperidyl]-3-propargyl-1,3-dihydro-2H-benzimidazol-2-one A 0.87M methylmagnesium bromide-tetrahydrofuran solution of 120 μl was added to a tetrahydrofuran 1 ml solution of 1-[(3RS,4RS)-1-cyclooctylmethyl-3-formyl-4-piperidyl]-3-ethyl-1,3-dihydro-2H-benzimidazol-2-one of 34 mg obtained in Example 58 (1) while cooling with ice, and the solution was stirred at a room temperature for 30 minutes. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=3/1) to obtain a compound of 4 mg called a (3R*,4R*) body of the captioned compound for the sake of convenience from the former fraction and a compound of 5 mg called a (3S*,4S*) body of the captioned compound for the sake of convenience from the latter fraction. (3R*,4R*) body:

$^1$H-NMR (CDCl$_3$) δ: 0.84–0.94(2H, m), 1.07–1.13(3H, m), 1.14–1.95(19H, m), 1.97–2.36(4H, m), 2.50–2.75(1H, m), 2.97–3.12(2H, m), 3.41–3.56(1H, m), 3.86–4.08(2H, m), 4.35–4.55(1H, m), 7.02–7.16 (3H, m), 7.28–7.37(1H, m)

FAB-MS (M+H)$^+$: 414 (3S*,4S*) body:

$^1$H-NMR (CDCl$_3$) δ: 0.93(3H, m), 1.20–1.41(6H, m), 1.41–1.87(13H, m), 1.97–2.23(6H, m), 2.42–2.72(1H, m), 2.95–3.13(2H, m), 3.53–3.68(1H, m), 3.88–4.02(2H, m), 4.27–4.45(1H, m), 7.00–7.12 (3H, m), 7.30–7.40(1H, m)

FAB-MS (M+H)$^+$: 414

Example 84

Production of 1-[(3RS,4RS)-1-cyclooctylmethyl-3-(1-hydroxypropyl)-4-piperidyl]-3-ethyl-1,3-dihydro-2H-benzimidazol-2-one A 1.0M ethylmagnesium bromide-tetrahydrofuran solution was used to obtain a compound called a (3R*,4R*) body of the captioned compound for the sake of convenience from the former fraction and a compound called a (3S*,4S*) body of the captioned compound for the sake of convenience from the latter fraction by the same method as that of Example 83. (3R*,4R*) body:

$^1$H-NMR (CDCl$_3$) δ: 0.80–0.91(5H, m), 1.21–1.38(7H, m), 1.40–1.89(13H, m), 2.01–2.22(5H, m), 2.53–2.70(1H, m), 2.92–3.16(3H, m), 3.89–4.08(2H, m), 4.38–4.57(1H, m), 7.03–7.13(3H, m), 7.31–7.35 (1H, m)

FAB-MS (M+H)$^+$: 428 (3S*,4S*) body:

$^1$H-NMR (CDCl$_3$) δ: 0.70–0.98(4H, m), 1.07–1.87(18H, m), 1.98–2.70(9H, m), 2.92–3.26(3H, m), 3.85–4.07(2H, m), 4.30–4.52(1H, m), 7.00–7.16(3H, m), 7.30–7.42(1H, m)

FAB-MS (M+H)$^+$: 428

Example 85

Production of 1-(1-cyclooctylmethyl-4-piperidyl)-3-[2-(methylsulfonylamino)ethyl]-1,3-dihydro-2H-benzimidazol-2-one Triethylamine of 60 μl and methanesulfonyl chloride of 17 μl were added to a methylene chloride 2 ml solution of 3-(2-aminoethyl)-1-(1-cyclooctylmethyl-4-piperidyl)-1,3-dihydro-2H-benzimidazol-2-one of 50 mg obtained in Example 61, and the solution was stirred at a room temperature for 30 minutes. The reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=10/1), whereby the captioned compound of 47 mg was obtained in the form of a colorless solid.

$^1$H-NMR (CDCl$_3$) δ: 1.20–1.31(2H, m), 1.39–1.85(15H, m), 2.02–2.18(4H, m), 2.44(2H, m), 2.88(3H, s), 3.02(2H, m), 3.53(2H, m), 4.09(2H, t, J=5.7 Hz), 4.33(1H, m), 5.10 (1H, m), 7.10(3H, m), 7.31(1H, m)

FAB-MS (M+H)$^+$: 463

Example 86

Production of 1-(1-cyclooctylmethyl-4-piperidyl)-3-[2-(sulfamoylamino)ethyl]-1,3-dihydro-2H-benzimidazol-2-one A methylene chloride 3.5 ml solution 250 μl of triethylamine of 92 μl, tert-butanol of 400 μl and chlorosulfonyl isocyanate of 170 μl was added to a methylene chloride 2ml solution of 3-(2-aminoethyl)-1-(1-cyclooctylmethyl-4-piperidyl)-1,3-dihydro-2H-benzimidazol-2-one of 50 mg obtained in Example 61, and the solution was stirred at a room temperature for 30 minutes. The reaction solution was condensed, and the resulting residue was dissolved in 10% hydrogen chloride-methanol of 1 ml, and the solution was stirred at a room temperature for 2 hours. The reaction solution was condensed again and then diluted with ethyl acetate. It was washed with a 2N sodium hydroxide aqueous solution and dried on anhydrous sodium sulfate. Then, the solvent was distilled off, and the resulting residue was separated and refined by means of silica gel column chromatography (chloroform/methanol=20/1), whereby the captioned compound of 41 mg was obtained.

$^1$H-NMR (CDCl$_3$) δ: 1.15–1.30(2H, m), 1.35–1.84(15H, m), 2.00–2.16(4H, m), 2.42(2H, m), 2.98(2H, m), 3.50(2H, m), 4.12(2H, t, J=5.7 Hz), 4.29(1H, m), 5.15(2H, br), 5.34(1H, br), 7.18(3H, m), 7.30(1H, m)

FAB-MS (M+H)$^+$: 464

Example 87

Production of 1-(1-cyclooctylmethyl-4-piperidyl)-3-[2-(dimethylsulfamoylamino)ethyl]-1,3-dihydro-2H-benzimidazol-2-one Triethylamine of 60 μl and then dimethylsulfamoyl chloride of 24 μl were added to a methylene chloride 2 ml solution of 3-(2-aminoethyl)-1-(1-cyclooctylmethyl-4-piperidyl)-1,3-dihydro-2H-benzimidazol-2-one of 50 mg obtained in Example 61, and the solution was stirred at a room temperature for one hour. The reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=20/1), whereby the captioned compound of 32 mg was obtained in the form of a colorless solid.

$^1$H-NMR (CDCl$_3$) δ: 1.25(2H, m), 1.39–1.80(15H, m), 2.01–2.20(4H, m), 2.44(2H, m), 2.73(6H, s), 3.01(2H, m), 3.46(2H, m), 4.07 (2H, t, J=6.0 Hz), 4.33(1H, m), 5.02(1H, m), 7.10(3H, m), 7.30(1H, m)

FAB-MS (M+H)$^+$: 492

Example 88

Production of 1-[(3RS,4RS)-1-cyclooctylmethyl-3-(3-methylaminopropyl)-4-piperidyl]-3-ethyl-1,3-dihydro-2H-benzimidazol-2-one 1-[(3RS,4RS)-1-cyclooctylmethyl-3-(2-formylethyl)-4-piperidyl]-3-ethyl-1,3-dihydro-2H-benzimidazol-2-one obtained in Example 81 (1) and methylamine hydrochloride were used to obtain the captioned compound by the same method as that of Example 3.

$^1$H-NMR (CDCl$_3$) δ: 0.83–1.00(4H, m), 1.02–1.83(20H, m), 1.90–2.52(11H, m), 2.96–3.08(2H, m), 3.89–4.17(3H, m), 6.96–7.09(3H, m), 7.19–7.27(1H, m)

FAB-MS (M+H)$^+$: 441

Example 89

Production of 1-[(3S*,4S*)-1-cyclooctylmethyl-3-(methylsulfonylamino)methyl-4-piperidyl]-3-ethyl-1,3-dihydro-2H-benzimidazol-2-one 1-[(3S*,4S*)-3-aminomethyl-1-cyclooctylmethyl-4-piperidyl]-3-ethyl-1,3-dihydro-2H-benzimidazol-2-one obtained in Example 60 was used to obtain the captioned compound by the same method as that of Example 85.

$^1$H-NMR (CDCl$_3$) δ: 1.15–1.40(5H, m), 1.41–1.91(14H, m), 1.98–2.30(4H, m), 2.39–2.68(2H, m), 2.68–2.85(4H, m), 2.97–3.14(3H, m), 3.88–4.08(2H, m), 4.16–4.34(1H, m), 5.30–5.55(1H, br), 7.03–7.18 (3H, m), 7.25–7.33(1H, m)

FAB-MS (M+H)$^+$: 477

Example 90

Production of 1-[(3RS,4RS)-3-(3-aminopropyl)-1-cyclooctylmethyl-4-piperidyl]-3-ethyl-1,3-dihydro-2H-benzimidazol-2-one 1-[(3RS,4RS)-1-cyclooctylmethyl-3-(3-hydroxypropyl)-4-piperidyl]-3-ethyl-1,3-dihydro-2H-benzimidazol-2-one obtained in Example 64 was used to obtain the captioned compound by the same method as that of Example 60.

$^1$H-NMR (CDCl$_3$) δ: 0.80–0.94(6H, m), 1.17–2.39(29H, m), 3.85–4.13(3H, m), 6.98–7.17(3H, m), 7.25–7.30(1H, m)

FAB-MS (M+H)$^+$: 427

[α]$_D^{20}$ −42.0° (c=0.5, CHCl$_3$) (as hydrochloride)

Example 91

Production of 1-[(3RS,4RS)-1-cyclooctylmethyl-3-vinyl-4-piperidyl]-3-ethyl-1,3-dihydro-2H-benzimidazol-2-one Potassium tert-butoxide of 127 mg was added to a tetrahydrofuran 7 ml solution of methyltriphenylphosphonium bromide of 400 mg while cooling with ice, and the solution was stirred for 30 minutes. Then, added thereto was a tetrahydrofuran 8 ml solution of 1-[(3RS,4RS)-1-cyclooctylmethyl-3-formyl-4-piperidyl]-3-ethyl-1,3-dihydro-2H-benzimidazol-2-one of 157 mg obtained in Example 58 (1), and the solution was further stirred for 30 minutes while cooling with ice. The reaction solution was diluted with ethyl acetate and washed with water and saturated brine, followed by drying on anhydrous sodium sulfate. Then, the solvent was distilled off, and the resulting residue was separated and refined by means of silica gel column chromatography (chloroform/methanol=100/1), whereby the captioned compound of 141 mg was obtained in the form of a colorless solid.

$^1$H-NMR (CDCl$_3$) δ: 1.19–1.33(6H, m), 1.40–1.84(13H, m), 1.94–2.17(4H, m), 2.37–2.52(1H, m), 2.91–3.23(3H, m), 3.93(2H, m), 4.08–4.30(1H, m), 4.76–4.85(2H, m), 5.49–5.61(1H, m), 6.96–7.09(3H, m), 7.20–7.30(1H, m)

FAB-MS (M+H)$^+$: 396

Example 92

Production of 1-(1-cyclooctylmethyl-3-methylene-4-piperidyl)-3-ethyl-1,3-dihydro-2H-benzimidazol-2-one (1) Production of 1-[(3RS,4RS)-3-bromomethyl-1-cyclooctylmethyl-4-piperidyl]-3-ethyl-1,3-dihydro-2H-benzimidazol-2-one Triphenylphosphine of 39 mg and carbon tetrabromide of 81 mg were added to a chloroform 2.5 ml solution of 1-[(3RS,4RS)-1-cyclooctylmethyl-3-hydroxymethyl-4-piperidyl]-3-ethyl-1,3-dihydro-2H-benzimidazol-2-one of 49 mg obtained in Example 42, and the solution was stirred at a room temperature for 2 hours. The reaction solution was diluted with ethyl acetate and washed with a saturated sodium bicarbonate aqueous solution and saturated brine, followed by drying on anhydrous sodium sulfate. Then, the solvent was distilled off, and the resulting residue was separated and refined by means of silica gel column chromatography (ethyl acetate/hexane=1/1), whereby the captioned compound of 30 mg was obtained in the form of a colorless solid.

(2) Production of 1-(1-cyclooctylmethyl-3-methylene-4-piperidyl)-3-ethyl-1,3-dihydro-2H-benzimidazol-2-one Sodium iodide of 24 mg and 1,8-diazabicyclo[5.4.0]-7-undecene of 49 μl were added to a toluene 1.5 ml solution of 1-[(3RS,4RS)-3-bromomethyl-1-cyclooctylmethyl-4-piperidyl]-3-ethyl-1,3-dihydro-2H-benzimidazol-2-one of 15 mg, and the solution was stirred at 110° C. for 16 hours. The reaction solution was allowed to come down to a room temperature and diluted with ethyl acetate. It was washed with water and saturated brine and dried on anhydrous sodium sulfate. Then, the solvent was distilled off, and the resulting residue was separated and refined by means of silica gel column chromatography (ethyl acetate/hexane=1/2), whereby the captioned compound of 2 mg was obtained in the form of a colorless solid.

¹H-NMR (CDCl₃) δ: 0.84–0.93(2H, m), 1.22–2.13(18H, m), 2.17–2.57(3H, m), 2.75–3.17(2H, m), 3.43–3.53(1H, m), 3.91–4.05(2H, m), 4.43(1H, s), 4.92(1H, s), 5.01–5.16 (1H, m), 6.99–7.22(4H, m)

FAB-MS (M+H)⁺: 382

Example 93
Production of 1-[(3RS 4RS)-3-(2-aminoethyl)-1-cyclooctylmethyl-4-piperidyl]-3-ethyl-1,3-dihydro-2H-benzimidazol-2-one 1-[(3RS,4RS)-1-cyclooctylmethyl-3-(2-hydroxyethyl)-4-piperidyl]-3-ethyl-1,3-dihydro-2H-benzimidazol-2-one obtained in Example 72 was used to obtain the captioned compound by the same method as that of Example 60.

¹H-NMR (CDCl₃) δ: 0.78–0.96(6H, m), 1.05–2.38(27H, m), 3.88–4.07(2H, m), 4.22–4.37(1H, m), 6.92–7.15(3H, m), 7.21–7.28(1H, m)

FAB-MS (M+H)⁺: 413

Example 94
Production of 1-[(3S*,4S*)-1-cyclooctylmethyl-3-(dimethylsulfamoyl)amino-4-piperidyl]-3-ethyl-1,3-dihydro-2H-benzimidazol-2-one 1-[(3S*,4S*)-3-aminomethyl-1-cyclooctylmethyl-4-piperidyl]-3-ethyl-1,3-dihydro-2H-benzimidazol-2-one obtained in Example 60 was used to obtain the captioned compound by the same method as that of Example 87.

¹H-NMR (CDCl₃) δ: 1.18–1.40(5H, m), 1.40–1.89(13H, m), 2.03–2.28(4H, m), 2.39–2.65(2H, m), 2.67–2.78(6H, m), 2.90–3.09(5H, m), 3.91–4.04(2H, m), 4.17–4.32(1H, m), 5.20–5.38(1H, br), 7.03–7.15 (3H, m), 7.26–7.32(1H, m)

FAB-MS (M+H)⁺: 506

Example 95
Production of 1-[(3S*,4S*) 1-cyclooctylmethyl-3-sulfamoylamino-4-piperidyl]-3-ethyl-1,3-dihydro-2H-benzimidazol-2-one 1-[(3S*,4S*)-3-aminomethyl-1-cyclooctylmethyl-4-piperidyl]-3-ethyl-1,3-dihydro-2H-benzimidazol-2-one obtained in Example 60 was used to obtain the captioned compound by the same method as that of Example 86.

¹H-NMR (CDCl₃) δ: 1.18–1.39(6H, m), 1.40–1.97(13H, m), 2.02–2.24(4H, m), 2.41–2.72(2H, m), 2.81–3.10(4H, m), 3.88–4.03(2H, m), 4.18–4.38(1H, m), 4.77–4.91(2H, br), 5.01–5.20(1H, m), 7.03–7.17 (3H, m), 7.24–7.32(1H, m)

FAB-MS (M+H)⁺: 478

[α]_D²⁰ –30.4(c=0.5, CHCl₃) (as hydrochloride)

Example 96
Production of 5-bromo-1-[(3RS,4RS)-1-cyclooctylmethyl-3-hydroxymethyl-4-piperidyl]-3-ethyl-1,3-dihydro-2H-benzimidazol-2-one (1) Production of 5-bromo-1-[(3RS,4RS)-1-cyclooctylmethyl-3-ethoxycarbonyl-4-piperidyl]-1,3-dihydro-2H-benzimidazol-2-one 5-Bromo-2-fluoronitrobenzene was used to obtain the captioned compound by the same methods as those of Example 37 (2) and then Example 35 (3).

(2) Production of 5-bromo-1-[(3RS,4RS)-1-cyclooctylmethyl-3-ethoxycarbonyl-4-piperidyl]-3-ethyl-1,3-dihydro-2H-benzimidazol-2-one 5-Bromo-1-[(3RS,4RS)-1-cyclooctylmethyl-3-ethoxycarbonyl-4-piperidyl]-1,3-dihydro-2H-benzimidazol-2-one and ethyl iodide were used to obtain the captioned compound by the same method as that of Example 13.

(3) Production of 5-bromo-1-[(3RS,4RS)-1-cyclooctylmethyl-3-hydroxymethyl-4-piperidyl]-3-ethyl-1,3-dihydro-2H-benzimidazol-2-one 5-bromo-1-[(3RS,4RS)-1-cyclooctylmethyl-3-ethoxycarbonyl-4-piperidyl]-3-ethyl-1,3-dihydro-2H-benzimidazol-2-one was used to obtain the captioned compound by the same method as that of Example 39.

¹H-NMR (CDCl₃) δ: 1.26(2H, m), 1.35(3H, t, J=7.2 Hz), 1.41–1.95(12H, m), 2.02–2.40(6H, m), 2.54(2H, m), 3.03 (2H, m), 3.34(2H, m), 3.94(2H, m), 4.38(1H, m), 7.19(3H, m)

FAB-MS (M+H)⁺: 478/480

Example 97
Production of 1-[(3RS,4RS)-3-aminomethyl-1-cyclooctylmethyl-4-piperidyl]-3-(2-dimethylaminoethyl)-1,3-dihydro-2H-benzimidazol-2-one (1) Production of 1-[(3RS,4RS)-3-azidemethyl-1-cyclooctylmethyl-4-piperidyl]-1,3-dihydro-2H-benzimidazol-2-one 1-[(3RS,4RS)-1-cyclooctylmethyl-3-hydroxymethyl-4-piperidyl]-1,3-dihydro-2H-benzimidazol-2-one obtained in Example 39 was used to obtain the captioned compound by the same method as that of Example 60 (1).

(2) Production of 1-[(3RS,4RS)-3-azidomethyl-1-cyclooctylmethyl-4-piperidyl]-3-(2-dimethylaminoethyl)-1,3-dihydro-2H-benzimidazol-2-one 1-[(3RS,4RS)-3-azidomethyl-1-cyclooctylmethyl-4-piperidyl]-1,3-dihydro-2H-benzimidazol-2-one and dimethylaminoethyl chloride hydrochloride were used to obtain the captioned compound by the same method as that of Example 13.

(3) Production of 1-[(3RS,4RS)-3-aminomethyl-1-cyclooctylmethyl-4-piperidyl]-3-(2-dimethylaminoethyl)-1,3-dihydro-2H-benzimidazol-2-one 1-[(3RS,4RS)-3-azidomethyl-1-cyclooctylmethyl-4-piperidyl]-3-(2-dimethylaminoethyl)-1,3-dihydro-2H-benzimidazol-2-one was used to obtain the captioned compound by the same method as that of Example 60 (2).

¹H-NMR (CDCl₃) δ: 1.25(3H, m), 1.27–2.28(19H, m), 2.32(6H, s), 2.52(2H, m), 2.64(2H, m), 3.05(2H, m), 4.00 (2H, m), 4.24(1H, m), 7.07(3H, m), 7.32(1H, m)

FAB-MS (M+H)⁺: 442

Example 98
Production of 1-[(3RS,4RS)-1-cyclooctylmethyl-3-(methylsulfonylamino)methyl-4-piperidyl]-3-(2-dimethylaminoethyl)-1,3-dihydro-2H-benzimidazol-2-one 1-[(3RS,4RS)-3-aminomethyl-1-cyclooctylmethyl-4-piperidyl]-3-(2-dimethylaminoethyl)-1,3-dihydro-2H-benzimidazol-2-one obtained in Example 97 was used to obtain the captioned compound by the same method as that of Example 85.

¹H-NMR (CDCl₃) δ: 1.25(3H, m), 1.35–1.90(13H, m), 1.98–2.22(4H, m), 2.31(6H, s), 2.43–2.72(4H, m), 2.76(3H, s), 2.83(1H, m), 3.02(3H, m), 4.00(2H, m), 4.23(1H, m), 5.48(1H, br), 7.08(3H, m), 7.30(1H, m)

FAB-MS (M+H)⁺: 520

Example 99
Production of 1-[(3RS,4RS)-1-cyclooctylmethyl-3-(sulfamoylamino)methyl-4-niperidyl]-3-(2-dimethylaminoethyl)-1,3-dihydro-2H-benzimidazol-2-one 1-[(3RS,4RS)-3-aminomethyl-1-cyclooctylmethyl-4-piperidyl]-3-(2-dimethylaminoethyl)-1,3-dihydro-2H-benzimidazol-2-one obtained in Example 97 was used to obtain the captioned compound by the same method as that of Example 86.

¹H-NMR (CDCl₃) δ: 1.24(4H, m), 1.40–1.88(12H, m), 2.02–2.20(4H, m), 2.30(6H, s), 2.52(2H, m), 2.77–3.08(6H, m), 3.86(1H, m), 4.22(2H, m), 4.90(1H, br), 5.06(2H, br), 7.04(1H, m), 7.10(2H, m), 7.30(1H, m)
FAB-MS (M+H)⁺: 521

Example 100
Production of 1-[(3RS,4RS)-1-cyclooctylmethyl-3-(methylsulfonylamino)methyl-4-piperidyl]-3-(2-aminoethyl)-1,3-dihydro-2H-benzimidazol-2-one
(1) Production of 1-[(3RS,4RS)-3-azidomethyl-1-cyclooctylmethyl-4-piperidyl]-3-[2-[bis(tert-butoxycarbonyl)amino]ethyl]-1,3-dihydro-2H-benzimidazol-2-one 1-[(3RS,4RS)-3-azidomethyl-1-cyclooctylmethyl-4-piperidyl]-1,3-dihydro-2H-benzimidazol-2-one obtained in Example 97 (1) was used to obtain the captioned compound by the same method as that of Example 13.
(2) Production of 1-[(3RS,4RS)-3-aminomethyl-1-cyclooctylmethyl-4-piperidyl]-3-[2-[bis(tert-butoxycarbonyl)amino]ethyl]-1,3-dihydro-2H-benzimidazol-2-one Triphenylphosphine of 18 mg was added to a tetrahydrofuran-water (10: 1) 3.3 ml solution of 1-[(3RS,4RS)-3-azidomethyl-1-cyclooctylmethyl-4-piperidyl]-3-[2-[bis(tert-butoxycarbonyl)amino]-ethyl]-1,3-dihydro-2H-benzimidazol-2-one of 39 mg, and the solution was heated for refluxing for 2 hours. The reaction solution was condensed, and the resulting residue was separated and refined by means of silica gel column chromatography (chloroform/methanol=10/1), whereby the captioned compound of 25 mg was obtained.
(3) Production of 1-[(3RS,4RS)-1-cyclooctylmethyl-3-(methylsulfonylamino)methyl-4-piperidyl]-3-(2-aminoethyl)-1,3-dihydro-2H-benzimidazol-2-one Triethylamine of 18 μl and methanesulfonyl chloride of 3 μl were added to a methylene chloride 1 ml solution of 1-[(3RS,4RS)-3-aminomethyl-1-cyclooctylmethyl-4-piperidyl]-3-[2-[bis(tert-butoxycarbonyl)amino]ethyl]-1,3-dihydro-2H-benzimidazol-2-one of 13 mg, and the solution was stirred at a room temperature for 30 minutes. The reaction solution was condensed, and the resulting residue was dissolved in 10% hydrogen chloride-methanol, and the solution was further stirred at a room temperature for 2 hours. The reaction solution was diluted with ethyl acetate and washed with a 2N sodium hydroxide aqueous solution and saturated brine, followed by drying on anhydrous sodium sulfate. Then, the solvent was distilled off, and the resulting residue was separated and refined by means of silica gel column chromatography (chloroform/methanol=10/1, 0.1% aqueous ammonia), whereby the captioned compound of 2 mg was obtained in the form of colorless liquid.

¹H-NMR (CDCl₃) δ: 1.17–1.32(5H, m), 1.40–1.91(17H, m), 2.07–2.23(2H, m), 2.63(3H, s), 2.75–3.17(5H, m), 3.91–4.16(2H, m), 4.16–4.36(1H, m), 7.02–7.13(3H, m), 7.30–7.38(1H, m)
FAB-MS (M+H)⁺: 492

Example 101
Production of 1-[(3RS,4RS)-1-cyclooctylmethyl-3-hydroxymethyl-4-piperidyl]-3-(2-fluoroethyl)-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one obtained in Example 37 and 2-fluoroethyl bromide were used to obtain the captioned compound by the same methods as those of Example 13 and then Example 39.

¹H-NMR (CDCl₃) δ: 1.18–1.38(4H, m), 1.39–1.94(13H, m), 1.99–2.48(5H, m), 2.63(1H, br), 3.06(2H, br), 3.36(2H, d, J=2.8 Hz), 4.13–4.47(3H, m), 4.72(2H, dt, J=4.8 Hz, 47.1 Hz), 7.08–7.43(4H, m)
FAB-MS (M+H)⁺: 418

Example 102
Production of 1-[(3RS,4RS)-1-cyclooctylmethyl-3-hydroxymethyl-4-piperidyl]-3-(2,2-difluoroethyl)-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one obtained in Example 37 and 2,2-difluoroethyl bromide were used to obtain the captioned compound by the same methods as those of Example 13 and then Example 39.

¹H-NMR (CDCl₃) δ: 1.20–1.38(4H, m), 1.40–1.81(10H, m), 1.82–2.30(7H, m), 2.30–2.71(2H, m), 2.98–3.12(2H, m), 3.37(2H, s), 4.17–4.43(3H, m), 6.05(1H, tt, J=4.2 Hz, 55.2 Hz), 7.09–7.39(4H, m)
FAB-MS (M+H)⁺: 436

Example 103
Production of 1-[(3RS,4RS)-1-cyclooctylmethyl-3-hydroxymethyl-4-piperidyl]-3-(2,2,2-trifluoroethyl)-1,3-dihydro-2H-benzimidazol-2-one 1-[(3RS,4RS)-1-cyclooctylmethyl-3-ethoxycarbonyl-4-piperidyl]-1,3-dihydro-2H-benzimidazol-2-one obtained in Example 37 and 2,2,2-trifluoroethyl iodide were used to obtain the captioned compound by the same methods as those of Example 13 and then Example 39.

¹H-NMR (CDCl₃) δ: 1.18–1.38(5H, m), 1.40–1.94(12H, m), 1.94–2.28(7H, m), 2.30–2.71(2H, m), 2.98–3.12(2H, m), 3.38(2H, s), 4.33–4.60(3H, m), 7.08–7.40(4H, m)
FAB-MS (M+H)⁺: 454

Example 104
Production of 1-[1-(5,5-difluorocyclooctylmethyl)-4-piperidyl]-1,3-dihydro-2H-benzimidazol-2-one 4-(2-Keto-1-benzimidazolinyl)piperidine and 5,5-difluorocyclooctane-1-carbaldehyde were used to obtain the captioned compound by the same method as that of Example 3.

¹H-NMR (CDCl₃) δ: 1.10–1.38(3H, m), 1.51–1.93(10H, m), 1.93–2.24(6H, m), 2.37–2.53(2H, m), 2.89–3.13(2H, m), 4.23–4.46(1H, m), 6.98–7.33(4H, m), 9.37(1H, br)
FAB-MS (M+H)⁺: 378

Example 105
Production of 1-(1-cyclooctylmethyl-3-pyrrolidyl)-1,3-dihydro-2H-benzimidazol-2-one 1-(3-Pyrrolidyl)-1,3-dihydro-2H-benzimidazol-2-one and cyclooctanecarbaldehyde were used to obtain the captioned compound by the same method as that of Example 3.

¹H-NMR (CDCl₃) δ: 1.24–1.84(15H, m), 2.10–2.40(5H, m), 2.55(1H, m), 3.13(2H, m), 5.20(1H, m), 7.07(3H, m), 7.84(1H, brs), 8.93(1H, brs)
FAB-MS (M+H)⁺: 328

Example 106
Production of 1-(1-cyclooctylmethyl-3-piperidyl)-1,3-dihydro-2H-benzimidazol-2-one 1-(3-Piperidyl)-1,3-dihydro-2H-benzimidazol-2-one and cyclooctanecarbaldehyde were used to obtain the captioned compound by the same method as that of Example 3.

¹H-NMR (CDCl₃) δ: 1.21(2H, m), 1.38–2.23(20H, m), 2.65(1H, m), 2.91(2H, m), 4.45(1H, m), 7.06(3H, m), 7.20(1H, m), 8.96(1H, brs)
FAB-MS (M+H)⁺: 342

Example 107
Production of 3-(2-aminoethyl)-1-[(3RS,4RS)-1-cyclooctylmethyl-3-(sulfamoylamino)methyl-4-piperidyl]-1,3-dihydro-2H-benzimidazol-2-one 1-[(3RS,4RS)-3-aminomethyl-1-cyclooctylmethyl-4-piperidyl]-3-[2-[bis(tert-butoxycarbonyl)amino]ethyl]-1,3-dihydro-2H-benzimidazol-2-one obtained in Example 100 (2) was used to obtain the captioned compound by the same method as that of Example 86.

$^1$H-NMR (CDCl$_3$) δ: 1.20–1.38(6H, m), 1.40–2.60(21H, m), 2.90–3.09(3H, m), 3.15–3.23(1H, m), 3.93–4.38(3H, m), 7.05–7.36(4H, m)

FAB-MS (M+H)$^+$: 493

Example 108
Production of 3-carboxymethyl-1-(1-cyclooctylmethyl-4-piperidyl)-1, 3-dihydro-2H-benzimidazol-2-one
(1) Production of 1-(1-cyclooctylmethyl-4-piperidyl)-3-ethoxycarbonylmethyl-1,3-dihydro-2H-benzimidazol-2-one 1-(1-Cyclooctylmethyl-4-piperidyl)-1,3-dihydro-2H-benzimidazol-2-one obtained in Example 6 and ethyl bromoacetate were used to obtain the captioned compound by the same method as that of Example 13.

(2) Production of 3-carboxymethyl-1-(1-cyclooctylmethyl-4-piperidyl)-1,3-dihydro-2H-benzimidazol-2-one A $^1$N sodium hydroxide aqueous solution of 100 μl was added to a tetrahydrofuran 1 ml solution of 1-(1-cyclooctylmethyl-4-piperidyl)-3-ethoxycarbonylmethyl-1, 3-dihydro-2H-benzimidazol-2-one of 3 mg, and the solution was stirred at a room temperature for 12 hours. The reaction solution was condensed, and the resulting residue was separated and refined by means of silica gel column chromatography (chloroform/methanol=5/1), whereby the captioned compound of 2 mg was obtained in the form of a white solid.

$^1$H-NMR (CDCl$_3$) δ: 0.80–1.80(5H, m), 1.82–2.55(18H, m), 2.97(2H, m), 4.35(3H, m), 6.90(3H, m), 7.35(1H, m)

FAB-MS (M+H)$^+$: 400

Example 109
Production of 1-[(3RS,4RS)-3-amino-1-cyclooctylmethyl-4-piperidyl]-1,3-dihydro-2H-benzimidazol-2-one Triethylamine of 4 μl and diphenylphosphoryl azide of 6 μl were added to a benzene 1.5 ml solution of 1-[(3RS,4RS)-3-carboxyl-1-cyclooctylmethyl-4-piperidyl]-1,3-dihydro-2H-benzimidazol-2-one of 10 mg obtained in Example 77, and the solution was heated for refluxing for 4 hours. The reaction solution was allowed to come down to a room temperature and diluted with ethyl acetate. It was washed with water and saturated brine and dried on anhydrous sodium sulfate. Then, the solvent was distilled off, and the resulting residue was separated and refined by means of silica gel column chromatography (chloroform/methanol=10/1), whereby the captioned compound of 1 mg was obtained in the form of a colorless liquid.

1H-NMR (CDCl$_3$) δ: 1.17–1.40(4H, m), 1.40–1.94(15H, m), 2.01–2.48(2H, m), 2.94–3.22(2H, m), 3.48–3.70(1H, m), 3.93–4.11(1H, m), 7.03–7.41(4H, m), 8.30(1H, br)

FAB-MS (M+H)$^+$: 357

Example 110
Production of 1-(2-cyclooctylmethyl-2-azabicyclo-[2.2.2]oct-5-yl)-1,3-dihydro-2H-benzimidazol-2-one
(1) Production of 2-benzyl-5-(2-nitrophenylamino)-2-azabicyclo-[2.2.2]octane Lithium aluminum hydride of 100 mg was added to a tetrahydrofuran 10 ml solution of 2-benzyl-2-azabicyclo[2.2.2]octan-5-one oxime of 150 mg, and the solution was heated for refluxing for 2 hours. The reaction solution was allowed to come down to a room temperature, and sodium sulfate- decahydrate of 10 g was added thereto. The solution was stirred at a room temperature for 10 minutes and then filtered, and the solvent was distilled off. The resulting residue was dissolved in n-butanol of 4 ml, and 2-fluoronitrobenzene of 92 mg and sodium carbonate of 138 mg were added thereto, followed by heating for refluxing for 14 hours. The reaction solution was allowed to come down to a room temperature and diluted with ethyl acetate. It was washed with saturated brine and dried on anhydrous sodium sulfate. Then, the solvent was distilled off, and the resulting residue was separated and refined by means of silica gel column chromatography (ethyl acetate/hexane=1/4), whereby obtained were an axial body 40 mg of the captioned compound and an equatorial body 80 mg of the captioned compound.

(2) Production of 1-(2-cyclooctylmethyl-2-azabicyclo[2.2.2]oct-5-yl)-1,3-dihydro-2H-benzimidazol-2-one.

The equatorial body and axial body of 2-benzyl-5-(2-nitrophenylamino)-2-azabicyclo[2.2.2]octane were used to obtain the equatorial body and axial body of the captioned compound by the same methods as those of Example 35 (3), (4) and (5) respectively.

Equatorial Body:

1H-NMR (CDCl$_3$) δ: 1.05–1.34(8H, m), 1.34–2.20(13H, m), 2.40(2H, m), 3.34(2H, m), 3.40(2H, d, J=6.9 Hz), 4.78(1H, m), 7.15(4H, m), 8.88(1H, br)

FAB-MS (M+H)$^+$: 368

Axial Body:

$^1$H-NMR (CDCl$_3$) δ: 1.20–1.40(4H, m), 1.40–1.89(15H, m), 2.03(2H, m), 2.24(2H, m), 2.33(2H, m), 2.49(2H, m), 4.72(1H, m), 7.15(3H, m), 7.30(1H, m), 8,57(1H, br)

FAB-MS (M+H)$^+$: 368

Example 111
Production of 1-(8-cyclooctylmethyl-8-azabicyclo-[4.3.0]non-2-yl)-1,3-dihydro-2H-benzimidazol-2-one 2-Amino-8-benzyl-8-azabicyclo[4.3.0]nonane was used to obtain the captioned compound by the same methods as those of Example 35 (3), (4) and (5).

$^1$H-NMR (CDCl$_3$) δ: 1.18(2H, m), 1.34–2.00(20H, m), 2.18–3.26(7H, m), 4.57(1H, m), 7.04(3H, m), 7.12(1H, m), 8.70(1H, m)

FAB-MS (M+H)$^+$: 382

Example 112
Production of 1-[(3RS,4RS)-1-cyclooctylmethyl-3-(2-pyridylmethyl)oxymethyl-4-piperidyl]-3-ethyl-1,3-dihydro-2H-benzimidazol-2-one 2-Chloromethylpyridine hydrochloride was used to obtain the captioned compound by the same method as that of Example 50.

$^1$H-NMR (CDCl$_3$) δ: 1.21–1.32(5H, m), 1.40–1.83(14H, m), 1.94–2.19(4H, m), 2.41–2.96(2H, m), 2.97–3.25(2H, m), 3.28–3.38(2H, m), 3.85–3.92(2H, m), 4.20–4.43(3H, m), 6.93–7.30(6H, m), 7.49–7.57 (1H, m), 8.41–8.46(1H, m)

FAB-MS (M+H)$^+$: 491

Example 113
Production of 1-[(3RS, 4RS)-1-cyclooctylmethyl-3-(4-pyridylmethyl)oxymethyl-4-piperidyl]-3-ethyl-1,3-dihydro-2H-benzimidazol-2-one 4-Chloromethylpyridine hydrochloride was used to obtain the captioned compound by the same method as that of Example 50.

$^1$H-NMR (CDCl$_3$) δ: 1.19–1.32(5H, m), 1.40–1.67(6H, m), 1.67–1.88(8H, m), 1.92–2.20(4H, m), 2.42–2.92(2H, m), 2.95–3.22(2H, m), 3.22–3.35(2H, m), 3.80–3.90(2H, m), 4.19–4.32(3H, m), 6.90–7.30 (6H, m), 8.41(2H, d, J=6.0 Hz)
FAB-MS (M+H)⁺: 491

Example 114

Production of 1-[(3RS,4RS)-1-cyclooctylmethyl-3-(3-pyridylmethyl)oxymethyl-4-piperidyl]-3-ethyl-1,3-dihydro-2H-benzimidazol-2-one 3-Chloromethylpyridine hydrochloride was used to obtain the captioned compound by the same method as that of Example 50.

¹H-NMR (CDCl₃) δ: 1.19–1.31(6H, m), 1.34–1.88(13H, m), 1.91–2.18(4H, m), 2.42–2.60(1H, m), 2.76–3.17(3H, m), 3.20–3.32(2H, m), 3.83–4.32(5H, m), 6.96–7.42(6H, m), 8.33(1H, d, J=1.8 Hz), 8.46 (1H, dd, J=1.8 Hz, 4.8 Hz)
FAB-MS (M+H)⁺: 491

Example 115

Production of 1-[(3RS,4RS)-3-(carbamoylamino)-methyl-1-cyclooctylmethyl-4-piperidyl]-3-ethyl-1,3-dihydro-2H-benzimidazol-2-one Carbonyldiimidazole of 20 mg was added to a tetrahydrofuran solution of 1-[(3RS,4RS)-3-aminomethyl-1-cyclooctylmethyl-4-piperidyl]-3-ethyl-1,3-dihydro-2H-benzimidazol-2-one of 10 mg obtained in Example 60, and the solution was stirred at a room temperature for 2 hours. The reaction solution was diluted with ethyl acetate and washed with water and saturated brine, followed by drying on anhydrous sodium sulfate. Then, the solvent was distilled off, and the resulting residue was dissolved in 25% aqueous ammonia-tetrahydrofuran (5:1) of 2 ml, and the solution was stirred at a room temperature for 2 hours. The reaction solution was diluted with ethyl acetate and washed with aqueous ammonia, followed by drying on anhydrous sodium sulfate. Then, the solvent was distilled off, and the resulting residue was separated and refined by means of silica gel column chromatography (chloroform/methanol=10/1), whereby the captioned compound of 4 mg was obtained.

¹H-NMR(CDCl₃) δ: 1.16–1.30(3H, m), 1.35(3H, t, J=7.2 Hz), 1.39–1.78(11H, m), 1.78–2.21(7H, m), 2.38–2.63(2H, m), 2.96–3.12(2H, m), 3.43–3.54(1H, m), 3.86–4.07(2H, m), 4.26(1H, br), 4.43(2H, br), 5.55(1H, br), 7.03–7.38(4H, m)
FAB-MS(M+H)⁺: 442

Example 116

Production of 1-[(3RS,4RS)-3-carbamoyloxymethyl-1-cyclooctylmethyl-4-piperidyl]-3-ethyl-1,3-dihydro-2H-benzimidazol-2-one Chlorosulfonyl isocyanate of 9 µl was added to a toluene 1 ml solution of 1-[(3RS,4RS)-1cyclooctylmethyl-3-ethoxycarbonyl-4piperidyl]-3-ethyl-1,3-dihydro-2H-benzimidazol-2-one of 30 mg obtained in Example 41, and the solution was stirred at a room temperature for 30 minutes. Then, water of 1 ml was added thereto, and the solution was further stirred at a room temperature for 30 minutes. The reaction solution was diluted with ethyl acetate and washed with a sodium bicarbonate aqueous solution and saturated brine, followed by drying on anhydrous sodium sulfate. Then, the solvent was distilled off, and the resulting residue was separated and refined by means of silica gel column chromatography (chloroform/methanol=10/1), whereby the captioned compound of 18 mg was obtained in the form of a colorless solid.

1H-NMR(CDCl₃) δ: 1.30(3H, m), 1.25–1.76(15H, m), 1.88 (2H, br), 2.40–3.50(9H, m), 3.63–4.06(4H, m), 4.51eb;normal;j (1H, br), 7.06(3H, m), 7.43(1H, br)
FAB-MS(M+H)⁺: 443

Example 117

Production of 3-[2-(carbamoylamino)ethyl]-1-(1-cyclooctylmethyl-4-piperidyl)-1,3-dihydro-2H-benzimidazol-2-one 3-(2-Aminoethyl)-1-(1-cyclooctylmethyl-4-piperidyl)-1,3-dihydro-2H-benzimidazol-2-one obtained in Example 61 was used to obtain the captioned compound by the same method as that of Example 115.

¹H-NMR(CDCl₃) δ: 1.17–1.38(3H, m), 1.40–1.65(7H, m), 1.65–1.79(6H, m), 2.02–2.20(5H, m), 2.37–2.53(2H, m), 3.01(2H, m), 3.49–3.57(2H, m), 4.03(2H, m), 4.22–4.35 (1H, m), 4.62(2H, br), 5.56 (1H, br), 7.07–7.32(4H, m)
FAB-MS(M+H)⁺: 428

Example 118

Production of 1-(1-cyclooctylmethyl-3,3-dimethyl-4-piperidyl)-1,3-dihydro-2H-benzimidazol-2-one (1) Production of 1-cyclooctylmethyl-3,3-dimethyl-4-piperidone 60% Sodium hydride of 105 mg was added to a dimethylformamide 6 ml solution of 1-cyclooctylmethyl-4-piperidone of 300 mg, and the solution was stirred at a room temperature for 30 minutes. Then, methyl iodide of 160 µl was added thereto, and the solution was further stirred for 8 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/20), whereby the captioned compound of 45 mg was obtained in the form of colorless liquid. Further, 1-cyclooctylmethyl-3,5-dimethyl-4-piperidone of 42 mg was obtained in the form of colorless liquid.

(2) Production of 1-(1-cyclooctylmethyl-3,3-dimethyl-4-piperidyl)-1,3-dihydro-2H-benzimidazol-2-one 1-Cyclooctylmethyl-3,3-dimethyl-4-piperidone was used to obtain the captioned compound by the same methods as those of Example 35 (1), (2) and (3).

¹H-NMR (CDCl₃) δ: 0.85–0.95(6H, br), 1.10–1.88(10H, m), 1.90–2.19(6H, m), 2.51(1H, m), 2.75(2H, m), 3.00(2H, m), 3.50(1H, m), 4.28(2H, m), 7.05(3H, m), 7.30(1H, m), 9.30(1H, br)
FAB-MS (M+H)⁺: 370

Example 119

Production of 1-(1-cyclooctylmethyl-r-3,c-5-dimethyl-t-4-piperidyl)-1,3-dihydro-2H-benzimidazol-2-one (1) Production of 1-cyclooctylmethyl-r-3,c-5-dimethyl-t-4-(2-nitrophenylamino)piperidine 1-Cyclooctylmethyl-3,5-dimethyl-4-piperidone obtained in Example 118 (1) was used to obtain the captioned compound by the same methods as those of Example 35 (1) and (2). Further, 1-cyclooctylmethyl-r-3,c-5-dimethyl-c-4-(2-nitrophenylamino)piperidine was obtained as well.

(2) Production of 1-(1-cyclooctylmethyl-r-3,c-5-dimethyl-t-4-piperidyl)-1,3-dihydro-2H-benzimidazol-2-one 1-Cyclooctylmethyl-r-3,c-5-dimethyl-t-4-(2-nitrophenylamino)piperidine was used to obtain the captioned compound by the same method as that of Example 35 (3).

¹H-NMR (CDCl₃) δ: 0.85(6H, d, J=6.9 Hz), 1.20–1.95 (15H, m), 2.90(2H, m), 3.24(2H, m), 3.33(2H, m), 3.74(2H, m), 4.28(1H, m), 6.98–7.20(4H, m), 7.77(1H, br)
FAB-MS (M+H)⁺: 370

Example 120

Production of 1-(1-cyclooctylmethyl-r-3,c-5-dimethyl-c-4-piperidyl)-1,3-dihydro-2H-benzimidazol-2-one 1-Cyclooctylmethyl-r-3,c-5-dimethyl-c-4-(2-nitrophenylamino)piperidine obtained in Example 119 (1) was used to obtain the captioned compound by the same method as that of Example 35 (3).

$^1$H-NMR (CDCl$_3$) δ: 0.75(6H, m), 1.16–1.91(17H, m), 2.12(2H, m), 2.49(2H, m), 2.98(2H, m), 3.75(1H, m), 7.06 (4H, m), 8.98(1H, br)

FAB-MS (M+H)$^+$: 370

Example 121

Production of 1-[1-(5,5-difluorocyclooctylmethyl)-4-piperidyl]-3-[2-(dimethylamino)ethyl]-1,3-dihydro-2H-benzimidazol-2-one 1-[1-(5,5-Difluorocyclooctylmethyl)-4-piperidyl]-1,3-dihydro-2H-benzimidazol-2-one obtained in Example 104 and dimethylaminoethyl chloride hydrochloride were used to obtain the captioned compound by the same method as that of Example 13.

$^1$H-NMR (CDCl$_3$) δ: 1.09–1.36(4H, m), 1.50–1.69(3H, m), 1.70–1.96(5H, m), 1.96–2.18(7H, m), 2.30–2.56(2H, m), 2.34(6H, s), 2.65(2H, t, J=7.5 Hz), 2.91–3.03(2H, m), 4.00(2H, t, J=7.5 Hz), 4.22–4.42(1H, m), 7.01–7.30(4H, m)

FAB-MS (M+H)$^+$: 449

Example 122

Production of 3-allyl-1-(1-cyclooctylmethyl-4-piperidyl)-1,3-dihydro-2H-benzimidazol-2-one 1-(1-Cyclooctylmethyl-4-piperidyl)-1,3-dihydro-2H-benzimidazol-2-one obtained in Example 6 and allyl bromide were used to obtain the captioned compound by the same method as that of Example 13.

$^1$H-NMR (CDCl$_3$) δ: 1.15–1.37(1H, m), 1.39–1.86(17H, m), 2.01–2.24(3H, m), 2.32–2.60(2H, m), 2.95–3.12(2H, m), 4.27–4.56(3H, m), 5.16–5.28(2H, m), 5.80–6.01(1H, m), 6.94–7.32(4H, m)

FAB-MS (M+H)$^+$: 382

Example 123

Production of 1-(1-cyclooctylmethyl-4-piperidyl)-3-cyclopentyl-1,3-dihydro-2H-benzimidazol-2-one 1-(1-Cyclooctylmethyl-4-piperidyl)-1,3-dihydro-2H-benzimidazol- 2-one obtained in Example 6 and cyclopentyl bromide were used to obtain the captioned compound by the same method as that of Example 13.

$^1$H-NMR (CDCl$_3$) δ: 1.18–1.36(2H, m), 1.39–1.87(18H, m), 1.88–2.27(9H, m), 2.31–2.60(2H, m), 2.90–3.11(2H, m), 4.23–4.43(1H, m), 4.79–4.93(1H, m), 6.96–7.34(4H, m)

FAB-MS (M+H)$^+$: 410

Example 124

Production of 1-(1-cyclooctylmethyl-4-piperidyl)-3-hydroxy-1,3-dihydro-2H-benzimidazol-2-one (1) Production of 4-(2-nitrophenylamino)-1-cyclooctylmethylpiperidine 1-Cyclooctylmethyl-4-piperidone was used to obtain the captioned compound by the same methods as those of Example 35 (1) and (2).

(2) Production of 4-[N-(cyanomethyl)-2-nitrophenylamino]-1-cyclooctylmethylpiperidine Potassium cyanide of 60 mg, zinc chloride of 100 mg and paraformaldehyde of 27 mg were added to an acetic acid 2 ml solution of 4-(2-nitrophenylamino)-1-cyclooctylmethylpiperidine of 100 mg, and the solution was stirred at 60° C. for 18 hours. The reaction solution was diluted with ethyl acetate and washed with a 2N potassium hydroxide aqueous solution and saturated brine, followed by drying on anhydrous sodium sulfate. Then, the solvent was distilled off, and the resulting residue was separated and refined by means of silica gel column chromatography (ethyl acetate/hexane=1/2), whereby the captioned compound of 13 mg was obtained.

(3) Production of 1-(1-cyclooctylmethyl-4-piperidyl)-3-hydroxy-1,3-dihydro-2H-benzimidazol-2-one 4-[N-(cyanomethyl)-2-nitrophenylamino]-1-cyclooctylmethylpiperidine of 13 mg was dissolved in a 90% ethanol aqueous solution of 1 ml, and sodium carbonate of 10 mg was added thereto, followed by stirring at 80° C. for 12 hours. The reaction solution was condensed, and the resulting residue was separated and refined by means of silica gel column chromatography (chloroform/methanol=10/1), whereby the captioned compound of 6 mg was obtained in the form of a colorless solid.

1H-NMR (CDCl$_3$) δ: 1.24(2H, m), 1.36–1.81(15H, m), 1.94–2.28(4H, m), 2.37(2H, m), 2.99(2H, m), 3.18(1H, br), 4.22(1H, m), 7.11(2H, m), 7.31(2H, m)

FAB-MS (M+H)$^+$: 358

Example 125

Production of 1-(1-cyclooctylmethyl-4-piperidyl)-3-methoxy-1,3-dihydro-2H-benzimidazol-2-one 1-(1-Cyclooctylmethyl-4-piperidyl)-3-hydroxy-1,3-dihydro-2H-benzimidazol-2-one of 4 mg obtained in Example 124 was dissolved in chloroform of 1 ml, and a diazomethane-diethyl ether solution of 0.5 ml was added thereto, followed by stirring at a room temperature for 15 hours. The reaction solution was condensed, and the resulting residue was separated and refined by means of silica gel column chromatography (chloroform/methanol=40/1), whereby the captioned compound of 3 mg was obtained in the form of a colorless solid.

1H-NMR(CDCl$_3$) δ: 1.28(4H, m), 1.40–1.87(13H, m), 2.11(4H, m), 2.43(2H, m), 3.02(2H, m), 4.10(3H, s), 4.35 (1H, m), 7.12(3H, m), 7.30(1H, m)

FAB-MS (M+H)$^+$: 372

Example 126

Production of 1-[1-[1-(cyclohexylmethyl)cyclooctyl]-methyl-4-piperidyl]-1,3-dihydro-2H-benzimidazol-2-one 1-Cyclohexylmethyl-1-cyclooctanecarboxylic acid of 125 mg was dissolved in thionyl chloride of 6 ml, and pyridine of 6 mlwas added thereto, followed by stirring at a room temperature for 5 hours. The reaction solution was diluted with ethyl acetate and washed with water and saturated brine, followed by drying on anhydrous sodium sulfate. Then, the solvent was distilled off, and the resulting residue was dissolved in tetrahydrofuran of 1.5 ml. Lithium aluminum hydride of 5 mg was added thereto, and the solution was stirred at 50° C. for 30 minutes. The reaction solution was allowed to come down to a room temperature and diluted with ethyl acetate. It was washed with a 1N sodium hydroxide aqueous solution and dried on anhydrous sodium sulfate. Then, the solvent was distilled off, and the resulting residue was separated and refined by means of silica gel column chromatography (ethyl acetate/hexane=1/4), whereby the captioned compound of 10 mg was obtained in the form of a colorless oily substance.

$^1$H-NMR (CDCl$_3$) δ: 0.86–1.02(2H, m), 1.10–1.41(8H, m), 1.41–1.93(18H, m), 2.17–2.27(3H, m), 2.33–2.52(4H, m), 2.87–3.00(2H, m), 4.25–4.38(1H, m), 7.02–7.30(4H, m), 9.09(1H, br)

FAB-MS (M+H)$^+$: 438

Example 127

Production of 1-[1-(1-benzylcyclooctyl)methyl-4-piperidyl]-1,3-dihydro-2H-benzimidazol-2-one 1-Benzyl-1-cyclooctanecarboxylic acid was used to obtain the captioned compound by the same method as that of Example 126.

¹H-NMR (CDCl₃) δ: 1.38–1.80(14H, m), 2.09–2.18(4H, m), 2.26–2.57(4H, m), 2.68(2H, s), 2.92–3.01(2H, m), 4.25–4.39(1H, m), 7.02–7.36(9H, m), 9.33(1H, br)

FAB-MS (M+H)⁺: 432

Example 128

Production of 1-[1-(tricyclo[3.2.1.1³,⁷]non-1-yl-methyl)-4-piperidyl]-1,3-dihydro-2H-benzimidazol-2-one 3-Noradamantanecarboxylic acid was used to obtain the captioned compound by the same method as that of Example 126.

¹H-NMR (CDCl₃) δ: 1.45–1.98(12H, m), 1.99–2.08(1H, m), 2.10–2.38(4H, m), 2.38–2.60(4H, m), 2.98–3.19(2H, m), 4.26–4.41(1H, m), 7.00–7.33(4H, m), 9.68(1H, br)

FAB-MS (M+H)⁺: 352

Example 129

Production of 1-(1-cyclooctylmethyl-4-methoxycarbonyl-4-piperidyl)-1,3-dihydro-2H-benzimidazol-2-one (1) Production of 1-(4-cyano-1-cyclooctylmethyl-4-piperidyl)-1,3-dihydro-2H-benzimidazol-2-one 1,2-Phenylenediamine of 620 mg, 1-cyclooctylmethyl-4-piperidone of 1.3 g and potassium cyanide of 370 mg were dissolved in 50% methanol hydrate of 4 ml, and 10% hydrogen chloride-methanol of 1 ml was added thereto, followed by stirring at a room temperature for 20 hours. The reaction solution was diluted with ethyl acetate and washed with a 1N sodium hydroxide aqueous solution and saturated brine, followed by drying on anhydrous sodium sulfate. Then, the solvent was distilled off, and the resulting residue was dissolved in chloroform of 8 ml. Triethylamine of 390 μl and carbonyldiimidazole of 690 mg were added thereto, and the solution was stirred at a room temperature for 2 hours. The reaction solution was diluted with ethyl acetate and washed with a 1N sodium hydroxide aqueous solution, followed by drying on anhydrous sodium sulfate. Then, the solvent was distilled off, and the resulting residue was separated and refined by means of an optical resolution column (CHIRALPAK AD column manufactured by Daicel Co., Ltd.; 0.1% diethylamine, hexane/isopropyl alcohol= 400/100), whereby the captioned compound of 352 mg was obtained.

(2) Production of 1-(1-cyclooctylmethyl-4-methoxycarbonyl-4-piperidyl)-1,3-dihydro-2H-benzimidazol-2-one 1-(4-Cyano-1-cyclooctylmethyl-4-piperidyl)-1,3-dihydro-2H-benzimidazol-2-one of 9 mg was dissolved in methanol of 1 ml, and a 6N sodium hydroxide aqueous solution of 300 μl was added thereto, followed by heating for refluxing for 3 days. The reaction solution was cooled down to a room temperature, and 10% hydrogen chloride-methanol was added thereto. pH was adjusted to about 8, and then insoluble matters were filtered off. The solvent was distilled off, and the resulting residue was dissolved in thionyl chloride of 1 ml, followed by stirring at a room temperature for 5 minutes. Thionyl chloride was distilled off, and methanol of 5 ml was added to the resulting residue, followed by stirring at a room temperature for 10 minutes. Then, the solvent was distilled off, and the resulting residue was diluted with ethyl acetate and washed with a 1N sodium hydroxide aqueous solution and saturated brine, followed by drying on anhydrous sodium sulfate. Then, the solvent was distilled off, and the resulting residue was separated and refined by means of silica gel column hromatography (ethyl acetate/hexane=1/2), whereby the captioned compound of 3 mg was obtained.

¹H-NMR (CDCl₃) δ: 1.21(2H, m), 1.37–1.80(13H, m), 2.10(2H, d, J=7.5 Hz), 2.48–2.65(6H, m), 2.84(2H, m), 3.70(3H, s), 7.04(3H, m), 7.17(1H, d, J=7.2 Hz), 8.87(1H, br)

FAB-MS (M+H)⁺: 400

Example 130

Production of 3-cyclobutyl-1-(1-cyclooctylmethyl-4-piperidyl)-1,3-dihydro-2H-benzimidazol-2-one Cyclobutyl bromide was used to obtain the captioned compound by the same method as that of Example 13.

¹H-NMR (CDCl₃) δ: 1.07–1.31(4H, m), 1.32–1.79(16H, m), 1.79–2.18(4H, m), 2.30–2.50(3H, m), 2.80–3.07(4H, m), 4.26–4.39(1H, m), 4.91(1H, m), 7.01–7.32(4H, m)

FAB-MS (M+H)+: 396

Example 131

Production of 1-(1-cyclooctylmethyl-4-methoxycarbonyl-4-piperidyl)-3-ethyl-1,3-dihydro-2H-benzimidazol-2-one 1-(1-Cyclooctylmethyl-4-methoxycarbonyl-4-piperidyl)-1,3-dihydro-2H-benzimidazol-2-one obtained in Example 129 and ethyl iodide were used to obtain the captioned compound by the same method as that of Example 13.

¹H-NMR (CDCl₃) δ: 1.26(2H, m), 1.32(3H, t, J=7.2 Hz), 1.37–1.78(13H, m), 2.10(2H, m), 2.45–2.66(6H, m), 2.84 (2H, m), 3.70(3H, s), 3.90(2H, q, J=7.2 Hz), 6.97–7.12(3H, m), 7.19(1H, m)

FAB-MS (M+H)⁺: 428

Example 132

Production of 1-(1-cyclooctylmethyl-4-hydroxymethyl-4-piperidyl)-1,3-dihydro-2H-benzimidazol-2-one 1-(1-Cyclooctylmethyl-4-methoxycarbonyl-4-piperidyl)-1,3-dihydro-2H-benzimidazol-2-one obtained in Example 129 was used to obtain the captioned compound by the same method as that of Example 39.

¹H-NMR (CDCl₃) δ: 1.20–1.32(4H, m), 1.40–1.79(111H, m), 1.99(2H, m), 2.13(2H, m), 2.30(2H, m), 2.79(4H, m), 4.15(2H, s), 7.06(3H, m), 7.64(1H, m), 8.41(1H, br)

FAB-MS (M+H)⁺: 372

Example 133

Production of 1-(1-cyclooctylmethyl-4-hydroxymethyl-4-piperidyl)-3-ethyl-1,3-dihydro-2H-benzimidazol-2-one 1-(1-Cyclooctylmethyl-4-methoxycarbonyl-4-piperidyl)-3-ethyl-1,3-dihydro-2H-benzimidazol-2-one obtained in Example 131 was used to obtain the captioned compound by the same method as that of Example 39.

¹H-NMR (CDCl₃) δ: 1.21–1.30(2H, m), 1.33(3H, t, J=7.2 Hz), 1.40–1.79(13H, m), 1.98(2H, m), 2.11(2H, m), 2.27 (2H, m), 2.79(4H, m), 3.91(2H, q, J=7.2 Hz), 4.16(2H, s), 7.00–7.13(3H, m), 7.66(1H, m)

FAB-MS (M+H)⁺: 400

Example 134

Production of 1-(1-cyclooctylmethyl-4-piperidyl)-3-dimethylamino-1,3-dihydro-2H-benzimidazol-2-one A dimethylformamide 0.5 ml solution of 4-bromo-1-cyclooctylmethylpiperidine of 36.8 mg was added to a dimethylformamide 1.0 ml suspension of 1-dimethylamino-1,3-dihydro-2H-benzimidazol-2-one of 11.2 mg, 60% sodium hydride of 7.6 mg and potassium iodide of 108 mg at a room temperature, and the solution was stirred at 150° C. for 2 hours. The reaction solution was diluted with ethyl acetate and washed with a 1N sodium hydroxide aqueous solution, followed by drying on anhydrous sodium sulfate. Then, the solvent was distilled off, and the resulting residue was separated and refined by means of preparative thin layer chromatography [Kiselgel™60F₂₅₄, Art 5744 (manufactured by Merck Co., Ltd.); ethyl acetate/hexane=

1/2], whereby the captioned compound of 0.7 mg was obtained in the form of colorless liquid.

$^1$H-NMR (CDCl$_3$) δ: 1.26(2H, m), 1.38–1.81(15H, m), 2.00–2.14(4H, m), 2.27–2.50(2H, m), 2.96–3.00(2H, m), 3.01(6H, s), 4.30(1H, m), 7.05(2H, m), 7.18(1H, m), 7.23 (1H, m)

FAB-MS (M+H)$^+$: 385

Example 135

Production of 1-[(3RS 4RS)-1-cyclooctylmethyl-3-(5-tetrazolylmethyl)-4-piperidyl]-3-ethyl-1,3-dihydro-2H-benzimidazol-2-one (1) Production of 1-[(3RS,4RS)-3-cyanomethyl-1-cyclooctylmethyl-4-piperidyl]-3-ethyl-1,3-dihydro-2H-benzimidazol-2-one Triethylamine of 0.26 ml and methanesulfonyl chloride of 87 tl were added to an ethyl acetate 10 ml solution of 1-[(3RS,4RS)-1-cyclooctylmethyl-3-hydroxymethyl-4-piperidyl]-3-ethyl-1,3-dihydro-2H-benzimidazol-2-one of 0.3 g obtained in Example 42, and the solution was stirred at a room temperature for 30 minutes. Insoluble matters were filtered off from the reaction solution, and the solvent was distilled off. The resulting residue was dissolved in dimethylformamide of 6 ml, and sodium cyanide of 0.11 g was added thereto, followed by stirring at 60° C. for 13 hours. The reaction solution was allowed to come down to a room temperature and diluted with ethyl acetate. It was washed with water and saturated brine and dried on anhydrous sodium sulfate. Then, the solvent was distilled off, and the resulting residue was separated and refined by means of silica gel column chromatography (chloroform/methanol= 30/1), whereby the captioned compound of 301 mg was obtained.

(2) Production of 1-[(3RS, 4RS)-1-cyclooctylmethyl-3-(5-tetrazolylmethyl)-4-piperidyl]-3-ethyl-1,3-dihydro-2H-benzimidazol-2-one Aluminum chloride of 32 mg and sodium azide of 70 mg were added to a tetrahydrofuran 2 ml solution of 1-[(3RS, 4RS)-3-cyanomethyl-1-cyclooctylmethyl-4-piperidyl]-3-ethyl-1,3-dihydro-2H-benzimidazol-2-one of 49 mg, and the solution was heated for refluxing for 10 hours. The reaction solution was cooled down to a room temperature and diluted with ethyl acetate. It was washed with water and saturated brine and dried on anhydrous sodium sulfate. Then, the solvent was distilled off, and the resulting residue was separated and refined by means of silica gel column chromatography (chloroform/methanol=50/1), whereby the captioned compound of 5 mg was obtained in the form of a colorless solid.

$^1$H-NMR (CDCl$_3$) δ: 0.83–1.75(19H, m), 1.80–1.96(2H, m), 2.05(2H, d, J=6.9 Hz), 2.52–2.69(2H, m), 2.72–3.02(2H, m), 3.06–3.21 (2H, m), 3.94–4.26(3H, m), 7.12–7.25(3H, m), 7.41(1H, d, J=6.9 Hz)

FAB-MS (M+H)$^+$: 452

Example 136

Production of 1-(1-cyclooctylmethyl-4-piperidyl)-3-ethoxycarbonyl-1,3-dihydro-2H-benzimidazol-2-one Ethyl chloroformate was used to obtain the captioned compound by the same method as that of Example 13.

1H-NMR (CDCl$_3$) δ: 1.25(2H, m), 1.48(3H, t, J=7.5 Hz), 1.50–1.79(15H, m), 2.10(4H, m), 2.47(2H, m), 3.00(2H, m), 4.32(1H, m), 4.51(2H, q, J=7.5 Hz), 7.09–7.21(2H, m), 7.28(1H, m), 7.92(1H, m)

FAB-MS (M+H)$^+$: 414

Example 137

Production of 3-(2-carbamoyloxyethyl)-1-(1-cyclooctylmethyl-4-piperidyl)-1,3-dihydro-2H-benzimidazol-2-one 1-(1-Cyclooctylmethyl-4-piperidyl)-3-(2-hydroxyethyl)-1,3-dihydro-2H-benzimidazol-2-one obtained in Example 30 was used to obtain the captioned compound by the same method as that of Example 116.

$^1$H-NMR (CDCl$_3$) δ: 0.88(2H, m), 1.15–1.80(15H, m), 2.05–2.20(4H, m), 2.42(2H, m), 3.01(2H, m), 4.14(2H, m), 4.36(2H, m), 4.60(1H, m), 7.15(3H, m), 7.29(1H, m)

FAB-MS (M+H)+: 429

Reference Example 1

Production of 4-(2-keto-1-benzimidazolinyl)-piperidine (1) Production of 4-(2-nitrophenylamino)-1-benzylpiperidine Sodium carbonate of 1.4 g and potassium iodide of 20 mg were added to a cyclohexanol 10 ml solution of 4-amino-1-benzylpiperidine of 2.0 g and 2-chloronitrobenzene of 2.4 g, and the solution was stirred at 150° C. for 24 hours. The reaction solution was allowed to come down to a room temperature and diluted with ethyl acetate. It was washed with water and saturated brine and dried on anhydrous sodium sulfate. Then, the solvent was distilled off, and the resulting residue was separated and refined by means of silica gel column chromatography (ethyl acetate/hexane=1/10), whereby the captioned compound of 2.77 g was obtained in the form of a yellow oily substance.

(2) Production of 1-(1-benzyl-4-piperidyl)-1,3-dihydro-2H-benzimidazol-2-one 4-(2-Nitrophenylamino)-1-benzylpiperidine of 2.77 g was dissolved in methanol of 60 ml, and 10% palladium-carbon of 500 mg was added thereto, followed by stirring at an atmospheric pressure and a room temperature under hydrogen atmosphere for 3 hours. The reaction solution was filtered through celite, and then the filtrate was condensed. Subsequently, the resulting residue was dissolved in chloroform of 50 ml, and carbonyldiimidazole of 2.2 g was added thereto, followed by stirring at a room temperature for one hour. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/3), whereby the captioned compound of 1.29 g was obtained in the form of a white solid.

(3) Production of 4-(2-keto-1-benzimidazolinyl)piperidine 1-(1-Benzyl-4-piperidyl)-1,3-dihydro-2H-benzimidazol-2-one of 1.2 g was dissolved in methanol of 50 ml, and 20% palladium hydroxide of 400 mg was added thereto, followed by stirring at a room temperature under hydrogen atmosphere of 3 atm for 12 hours. The reaction solution was filtered through celite, and then the solvent was distilled off from the filtrate to obtain the captioned compound of 1.0 g in the form of a white solid.

$^1$H-NMR (DMSO-d$_6$) δ: 1.80(2H, m), 2.64(2H, m), 3.08 (2H, m), 3.37(2H, m), 3.80(1H, br), 4.52(1H, m), 6.98(3H, m), 7.48(1H, m), 10.93(1H, brs)

Reference Example 2

Production of 4-(2-keto-5-methyl-1-benzimidazolinyl) piperidine (1) Production of 4-(2-nitro-4-methylphenylamino)-1-benzylpiperidine Sodium carbonate of 6.2 g and potassium iodide of 50 mg were added to a cyclohexanol 50 ml solution of 4-amino-1-benzylpiperidine of 11.0 g and 4-chloro-3-nitrotoluene of 10.0 g, and the solution was heated and stirred at 150° C. for 41 hours. The reaction solution was allowed to come down to a room temperature and diluted with ethyl acetate. It was washed with water and saturated brine and dried on anhydrous sodium sulfate. Then, the solvent was distilled off, and the resulting residue was separated and refined by means of silica gel column chromatography (ethyl acetate/hexane=1/3), whereby the captioned compound of 6.2 g was obtained in the form of a yellow oily substance.

(2) Production of 1-(1-benzyl-4-piperidyl)-5-methyl-1,3-dihydro-2H-benzimidazol-2-one 4-(2-Nitro-4-methylphenylamino)-1-benzylpiperidine of 6.2 g was dissolved in a mixed solvent of methanol 60 ml and tetrahydrofuran 15 ml, and 10% palladium-carbon of 1.5 g was added thereto, followed by stirring at an atmospheric pressure and a room temperature under hydrogen atmosphere for 3 hours. The reaction solution was filtered through celite, and then the filtrate was condensed. Subsequently, the resulting residue was dissolved in chloroform of 100 ml, and carbonyldiimidazole of 4.6 g was added thereto, followed by stirring at a room temperature for 12 hours. The reaction solution was diluted with ethyl acetate and washed with water and saturated brine, followed by drying on anhydrous sodium sulfate. Then, the solvent was distilled off, and the resulting residue was separated and refined by means of silica gel column chromatography (ethyl acetate/hexane=1/3), whereby the captioned compound of 3.6 g was obtained in the form of a white solid.

(3) Production of 4-(2-keto-5-methyl-1-benzimidazolinyl) piperidine 1-(1-Benzyl-4-piperidyl)-5-methyl-1,3-dihydro-2H-benzimidazol-2-one of 2.5 g was dissolved in ethanol of 100 ml, and 20% palladium hydroxide of 800 mg was added thereto, followed by stirring at a room temperature under hydrogen atmosphere of 3 atm for 12 hours. The reaction solution was filtered through celite, and then the solvent was distilled off from the filtrate to obtain the captioned compound of 1.6 g in the form of a white solid.

$^1$H-NMR (DMSO-$d_6$) δ: 1.54(2H, m), 2.15(2H, m), 2.28 (3H, s), 2.54(2H, m), 3.04(2H, m), 3.28(1H, br), 4.18(1H, m), 6.77(2H, m), 7.14(1H, m), 10.69(1H, br)

Reference Example 3
Production of 1-dimethylamino-1,3-dihydro-2H-benzimidazol-2-one
(1) Production of 1-acetamido-1,3-dihydro-2H-benzimidazol-2-one Ethyl chloroformate of 286 μl was dropwise added to a pyridine 5 ml solution of N'-(2-aminophenyl)acetohydrazide of 450 mg, and the solution was stirred at a room temperature for one hour and then heated for refluxing for 14 hours. The solvent was distilled off, and the resulting residue was diluted with chloroform and water. The aqueous layer was washed with chloroform, and crystals obtained from the aqueous layer were filtered, followed by drying under reduced pressure, whereby the captioned compound of 167 mg was obtained in the form of a white solid.

(2) Production of 1-amino-1,3-dihydro-2H-benzimidazol-2-one hydrochloride

1-Acetamido-1,3-dihydro-2H-benzimidazol-2-one of 200 mg was suspended in conc. hydrochloric acid of 5 ml, and the solution was stirred at 120° C. for 30 minutes. The reaction solution was condensed to obtain the captioned compound of 167 mg in the form of a white solid.

(3) Production of 1-dimethylamino-1,3-dihydro-2H-benzimidazol-2-one

An acetic acid 1 ml suspension of 1-amino-1,3-dihydro-2H-benzimidazol-2-one hydrochloride of 10 mg, 35% formalin of 20 μl and 10% palladium-carbon was stirred at an atmospheric pressure and a room temperature for 30 minutes under hydrogen atmosphere. The reaction solution was filtered through celite and then diluted with ethyl acetate. It was washed with a 2N sodium hydroxide aqueous solution and dried on anhydrous sodium sulfate. Then, the solvent was distilled off to obtain the captioned compound of 11.2 mg in the form of a white solid.

$^1$H-NMR (CD$_3$OD) δ: 2.98(6H, s), 6.98–7.21(4H, m)

Industrial Applicability

The compound of the present invention specifically prevents nociceptin from binding to a nociceptin receptor ORL1 and therefore is useful as an analgesic against diseases accompanied with pains such as cancerous pain, postoperative pain, migraine, gout, chronic rheumatism, chronic pain and neuralgia, a reliever against tolerance to a narcotic analgesic represented by morphine, a reliever against dependence on a narcotic analgesic represented by morphine, an analgesic enhancer, an antiobestic, a drug for ameliorating brain function, a remedy for schizophrenia, a remedy for Parkinsonism, a remedy for chorea, an antidepressant, a remedy for diabetes insipidus, a remedy for polyuria, or a remedy for hypotension.

What is claimed is:

1. A compound represented by Formula (I)

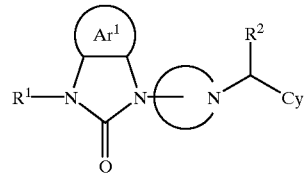

[I]

wherein

represents a benzene ring which may have a substituent selected from the group consisting of a halogen atom, a lower alkyl group, an amino group, a lower alkylamino group, a di(lower alkyl)amino group, a hydroxyl group, a lower alkoxy group and a carboxyl group; Ar$^2$ represents an aromatic carbo- or heterocyclic group which may have a substituent selected from the group consisting of a halogen atom, a lower alkyl group, an amino group, a lower alkylamino group, a di(lower alkyl)amino group, a hydroxyl group, a lower alkoxy group and a carboxyl group; Cy represents a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, an amino group, a lower alkylamino group, a di(lower alkyl)amino group, a lower alkoxy group and a group represented by —R$^4$;

represents a piperidinyl group, which may have a substituent selected from the group consisting of a halogen atom, a lower alkylidene group, a lower alkenyl group, a lower alkynyl group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group, a di(lower alkyl)carbamoyl group and a group represented by —R³; R¹ represents a hydrogen atom, a lower alkenyl group, a lower alkynyl group, a cyclo(lower alkyl) group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group or a di(lower alkyl)carbamoyl group, or a lower alkyl group which may have a substituent selected from the group consisting of a halogen atom, a cyclo(lower alkyl) group, an amino group, a lower alkylamino group, a di(lower alkyl)amino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group and a group represented by —Ar²; R²represents a hydrogen atom or a lower alkyl group; R³ represents a lower alkyl group which may have a substituent selected from the group consisting of an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group, an aromatic heterocyclic group and a group represented by —R⁵; R⁴ represents a lower alkyl group which may have a substituent selected from the group consisting of a cycloalkyl group having 3 to 10 carbon atoms and an aromatic carbo- or heterocyclic group; and R⁵ represents a lower alkyl)amino group, a di(lower alkyl)amino group or a lower alkoxy group, which may have an aromatic carbo- or heterocyclic group, a salt or ester thereof.

2. The compound as described in claim 1, which is a compound represented by Formula (I-a)

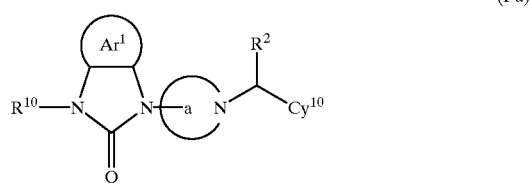

(I-a)

wherein

represents a benzene ring which may have a substituent selected from the group consisting of a halogen atom, a lower alkyl group, an amino group, a lower alkylamino group, a di(lower alkyl)amino group, a hydroxyl group, a lower alkoxy group and a carboxyl group; Ar² represents an aromatic carbo- or heterocyclic group which may have a substituent selected from the group consisting of a halogen atom, a lower alkyl group, an amino group, a lower alkylamino group, a di(lower alkyl)amino group, a hydroxyl group, a lower alkoxy group and a carboxyl group; Cy¹⁰ represents a mono-, bit or tricyclic aliphatic carbocyclic group having 3 to 20 carbon atoms, which may have a substituent selected from the group consisting of a halogen atom, a lower alkyl group, a lower alkylidene group, a lower alkenyl group, a lower alkynyl group, an amino group, a lower alkylamino group, a di(lower alkyl)amino group and a lower alkoxy group;

represents a piperidinyl group, which may have a substituent selected from the group consisting of a halogen atoms a lower alkenyl group, a lower alkynyl group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group, a di(lower alkyl)-carbamoyl group and a group represented by —R³⁰, R¹⁰ represents a hydrogen atom, a lower alkenyl group, a lower alkynyl group, a cyclo(lower alkyl) group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group or a di(lower allyl)carbamoyl group, or a lower alkyl group which may have a substituent selected from the group consisting of a cyclo(lower allyl) group, an amino group, a (lower alkyl)amino group, a di(lower alkyl) amino group, a hydroxyl group, a lower alkoxy group, a carboxyl group, a lower alkoxycarbonyl group, a carbamoyl group, a lower alkylcarbamoyl group, a di(lower alkyl) carbamoyl group and a group represented by —Ar², R² represents a hydrogen atom or a lower alkyl group; and R³⁰ represents a lower alkyl group which may have a substituent selected from the group consisting of an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group and a di(lower alkyl)carbamoyl group.

3. The compound as described in claim 1, wherein the mono-, bi or tricyclic aliphatic carbocyclic group of Cy has 6 to 20 carbon atoms.

4. The compound as described in claim 2, wherein the mono-, bi or tricyclic aliphatic carbocyclic group of Cy has 8 to 12 carbon atoms.

5. The compound as described in claim 1, wherein the mono-, bi- or tricyclic aliphatic carbocyclic group having 3 to 20 carbon atoms of Cy is cyclohexyl.

6. The compound as described in claim 1, wherein the mono-, bi- or tricyclic aliphatic carbocyclic group having 3 to 20 carbon atoms of Cy is cycloheptyl, cyclooctyl, cyclononyl, cyclodecyl, 1-cyclooctenyl, 1-cyclononenyl, 1-cyclodecenyl, bicyclo[3.2.1]oct-3-yl, bicyclo[4.4.0]dec-2-yl, bicyclo[4.4.0]dec-3-yl, tricyclo[3.2.1.1³·⁷]non-1-yl or tricyclo[3.3.1.1³·⁷]dec-1-yl.

7. The compound as described in claim 1, wherein the mono-, bi or tricyclic aliphatic carbocyclic group having 3 to 20 carbon atoms of Cy is cyclooctyl.

8. The compound as described in claim 1, wherein

is 1,4-piperidinediyl, 4-methoxycarbonyl-1,4-piperidinediyl, 3-methyl-1,4-piperidinediyl, 3-(methylsulfonylamino)methyl-1,4-piperidinediyl, 3-(aminosulfonylamino)-methyl-1,4-piperidinediyl, 3-(carbamoylamino)methyl-1,4-piperidine diyl, 2-hydroxymethyl-1,4-piperidinediyl, 3-hydroxymethyl-1,4-piperidinediyl, 3-(1-hydroxyethyl)-1,4-piperidinediyl, 3-(1-hydroxypropyl)-1,4-piperidinediyl or 3-(3-pyridylmethyloxy)methyl-1,4-piperidinediyl.

9. The compound as described in claim 1, wherein

is 1,4-piperidinediyl.

10. The compound as described in claim 1, wherein

is 3-methyl-1,4-piperidinediyl or 3-hydroxymethyl-1,4-piperidinediyl.

11. The compound as described in claim 1, wherein $R^1$ is a hydrogen atom or a lower alkyl group which may have a substituent selected from the group consisting of a halogen atom, a cyclo(lower alkyl) group, an amino group, a lower alkylamino group, a di(lower alkyl)amino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)-amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl) carbamoyl group and a group represented by —$Ar^2$.

12. The compound as described in claim 1, wherein $R^2$ is a hydrogen atom or methyl.

13. A process for preparing a compound represented by Formula (II)

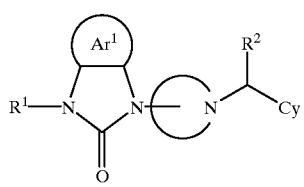

(II)

wherein

represents a benzene ring which may have a substituent selected from the group consisting of a halogen atom, a lower alkyl group, an amino group, a lower alkylamino group, a di(lower allyl)amino group, a hydroxyl group, a lower alkoxy group and a carboxyl group; $Ar^2$ represents an aromatic carbo- or heterocyclic group which may have a substituent selected from the group consisting, of a halogen atom, a lower alkyl group, an amino group, a lower alkylamino group, a di(lower allyl)amino group, a hydroxyl group, a lower alkoxy group and a carboxyl group; Cy represents a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, an amino group, a lower alkylamino group, a di(lower alkyl)amino group, a lower alkoxy group and a group represented by —$R^4$;

represents a piperidinyl group, which may have a substituent selected from the group consisting of a halogen atom, a lower alkylidene group, a lower alkenyl group, a lower alkynyl group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group, a di(lower alkyl) carbamoyl group and a group represented by —$R^3$; $R^1$ represents a hydrogen atom, a lower alkenyl group, a lower alkynyl group, a cyclo(lower alkyl) group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group or a di(lower alkyl)carbamoyl group, or a lower alkyl group which may have a substituent selected from the group consisting of a halogen atom, a cyclo(lower alkyl) group, an amino group, a lower alkylamino group, a di(lower alkyl)amino group, a (lower alkyl) sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxy group, a carbamoyloxy group, a lower alkylcarbamoyloxy group, a di(lower alkyl) carbamoyloxy group, a carboxyl group, a lower alkoxycarbonyl group, a carbamoyl group, a lower alkylcarbamoyl group, a di(lower alkyl)carbamoyl group and a group represented by —$Ar^2$; $R^3$ represents a lower alkyl group which may have a substituent selected from the group consisting of an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group, an aromatic heterocyclic group and a group represented by —$R^5$; and $R^5$ represents a lower alkylamino group, a di(lower alkyl)amino group or a lower alkoxy group, which may have an aromatic carbo- or a heterocyclic group, and $R^2$ and $R^4$ are synonymous with those described below; a salt or ester thereof, wherein a compound represented by Formula (II)

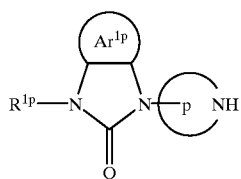

wherein

represents a benzene ring which may have a substituent selected from the group consisting of a halogen atom, a lower allyl group, a di(lower alkyl)amino group and a lower alkoxy group, and an amino group, a lower alkylamino group, a hydroxyl group and a carboxyl group, which may be protected; $Ar^{2p}$ represents an aromatic carbo- or heterocyclic group which may have a substituent selected from the group consisting of a halogen atom, a lower alkyl group, a di(lower alkyl)amino group and a lower alkoxy group, and an amino group, a lower alkylamino group, a hydroxyl group and a carboxyl group, which may be protected;

represents a piperdinyl group, which may have a substituent selected from the group consisting of a halogen atom, a lower alkylidene group, a lower alkenyl group, a lower alkynyl group, a di(lower alkyl)amino group, a lower alkoxy group, a lower alkoxycarbonyl group, a di(lower allyl) carbamoyl group and a group represented by —$R^{3p}$, and an amino group, a lower alkylamino group, a hydroxyl group, a carboxyl group, a carbamoyl group and a lower alkylcarbamoyl group, which may be protected; $R^{1p}$ represents a hydrogen atom, a lower alkenyl group, a lower alkynyl group, a cyclo(lower alkyl) group, a di(lower alkyl)amino group, a lower alkoxy group, a lower alkoxycarbonyl group or a di(lower alkyl)carbamoyl group, or an amino group, a lower alkylamino group, a hydroxyl group, a carboxyl group, a carbamoyl group or a lower alkylcarbamoyl group, which may be protected, or a lower alkyl group which may have a substituent selected from the group consisting of a halogen atom, a cyclo(lower alkyl) group, a di(lower alkyl) amino group, a lower alkoxy group, a di(lower alkyl) carbamoyloxy group, a lower alkoxycarbonyl group, a di(lower alkyl)carbamoyl group and a group represented by —$Ar^{2p}$, and an amino group, a lower alkylamino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a carboxyl group, a carbamoyl group and a lower alkylcarbamoyl group, which may be protected; $R^{3p}$ represents a lower alkyl group which may have a substituent selected from the group consisting of a di(lower alkyl)carbamoyloxy group, a lower alkoxycarbonyl group, a di(lower alkyl)carbamoyl group, an aromatic heterocyclic group and a group represented by —$R^{5p}$, and an amino group, a lower alkylsulfonylamino group, an aminosulfonylamino group, a (lower alkylamino) sulfonylamino group, a (di-lower alkylamino)sulfonylamino group, a carbamoylamino group, a (lower alkylcarbamoyl) amino group, a (di-lower alkylcarbamoyl)amino group, a hydroxyl group, a carbamoyloxy group, a lower alkylcarbamoyloxy group, a carboxyl group, a carbamoyl group and a lower alkylcarbamoyl group, which may be protected; and $R^{5p}$ represents a lower alkylamino group which may be protected, a di(lower alkyl)amino group or a lower alkoxy group, which may have an aromatic carbo- or heterocyclic group; is reacted with a compound represented by Formula (III)

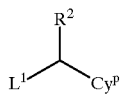

wherein $Cy^p$ represents a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, a di(lower alkyl)amino group, a lower alkoxy group and a group represented by —$R^4$, and an amino group and a lower alkylamino group, which may be protected; $L^1$ represents a leaving group; $R^2$ represents a hydrogen atom or a lower alkyl group; and $R^4$ represents a lower alkyl group which may have a substituent selected from the group consisting of a cycloalkyl group having 3 to 10 carbon atoms and an aromatic carbo- or heterocyclic group, to prepare a compound represented by Formula (IV)

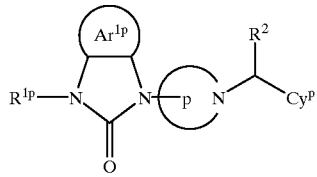

wherein

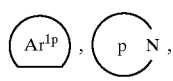

$Cy^p$, $R^{1p}$ and $R^2$ are synonymous with those described above, and the protective groups are op ally removed.

14. A process for preparing a compound represented by Formula (I)

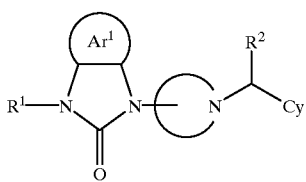
(I)

wherein

represents a benzene ring which may have a substituent selected from the group consisting of a halogen atom, a lower alkyl group, an amino group, a lower alkylamino group, a di(lower alkyl)amino group, a hydroxyl group, a lower alkoxy group and a carboxyl group; $Ar^2$ represents an aromatic carbo- or heterocyclic group which may have a substituent selected from the group consisting of a halogen atom, a lower alkyl group, an amino group, a lower alkylamino group, a di(lower allyl)amino group, a hydroxyl group, a lower alkoxy group and a carboxyl group; Cy represents a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, an amino group, a lower alkylamino group, a di(lower alkyl)amino group, a lower alkoxy group and a group represented by $—R^4$;

represents a piperidinyl group, which may have a substituent selected from the group consisting of a halogen atom, a lower alkylidene group, a lower alkenyl group, a lower alkynyl group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group, a di(lower alkyl)carbamoyl group and a group represented by $—R^3$; $R^1$ represents a hydrogen atom, a lower alkenyl group, a lower alkynyl group, a cyclo(lower alkyl) group, an amino group, a lower alkylamino group, a di(lower alkyl)amino group, a hydroxyl group, a lower alkoxy group, a carboxyl group, a lower alkoxycarbonyl group, a carbamoyl group, a lower alkylcarbamoyl group or a di(lower alkyl)carbamoyl group, or a lower alkyl group which may have a substituent selected from the group consisting of a halogen atom, a cyclo(lower alkyl) group, an amino group, a lower alkylamino group, a di(lower alkyl)amino group, a (lower alkyl)sulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a lower alkoxy group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group and a group represented by $—Ar^2$; $R^3$ represents a lower alkyl group which may have a substituent selected from the group consisting of an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a di(lower alkyl)carbamoyloxy group, a carboxyl group, a lower alkoxycarbonyl group, a carbamoyl group, a lower alkylcarbamoyl group, a di(lower alkyl)carbamoyl group, an aromatic heterocyclic group and a group represented by $—R^5$ and $R^6$ represents a lower alkylamino group, a di(lower alkyl)amino group or a lower alkoxy group, which may have an aromatic carbo- or heterocyclic group, and $R^2$ and $R^3$ are synonymous with those described below, a salt or ester thereof, wherein a compound represented by Formula (XVII)

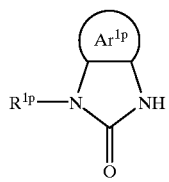
(XVII)

wherein

represents a benzene ring which may have a substituent selected from the group consisting of a halogen atom, a lower alkyl group, a di(lower alkyl)amino group and a lower alkoxy group, and an amino group, a lower alkylamino group, a hydroxyl group and a carboxyl group, which may be protected; $Ar^{2p}$ represents an aromatic carbo- or heterocyclic group which may have a substituent selected from the group consisting of a halogen atom, a lower alkyl group, a di(lower allyl)amino group and a lower alkoxy group, and an amino group, a lower alkylamino group, a hydroxyl group and a carboxyl group, which may be projected; $R^{1p}$ represents a hydrogen atom, a lower alkenyl group, a lower alkynyl group, a cyclo(lower alkyl) group, a di(lower alkyl) amino group, a lower alkoxy group, a lower alkoxycarbonyl group or a di(lower alkyl)carbamoyl group, or an amino group, a lower alkylamino group, a hydroxyl group, a carboxyl group, a carbamoyl group or a lower alkylcarbamoyl group, which may be protected, or a lower alkyl group which may have a substituent selected from the group consisting of a halogen atom, a cyclo(lower alkyl) group, a di(lower alkyl)amino group, a lower alkoxy group, a di(lower alkyl)carbamoyloxy group, a lower alkoxycarbonyl group, a di(lower alkyl)carbamoyl group and a group represented by $—Ar^{2p}$, and an amino group, a lower alkylamino group, a (lower alkyl)sulfonylamino group, an aminosulfonylamino group, a (lower alkylamino)sulfonylamino group, a (dilower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a carboxyl group, a carbamoyl group and a lower alkylcarbamoyl group, which may be protected, is reacted with a compound represented by Formula (XVIII)

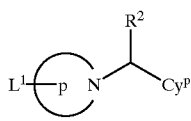

(XVIII)

wherein $Cy^p$ represents a mono-, bi- or tricyclic aliphatic carbocyclic group having 3 to 20 carbon atoms, which may have a substituent selected from the group consisting of a halogen atom, a lower alkylidene group, a lower alkenyl group, a lower alkynyl group, a di(lower alkyl)amino group, a lower alkoxy group and a group represented by —$R^4$, and an amino group and a lower alkylamino group, which may be protected; $L^1$ represents a leaving group;

represents a piperidinyl group, which may have a substituent selected from the group consisting of a halogen atom, a lower alkylidene group, a lower alkenyl group, a lower alkynyl group, a di(lower alkyl)amino group, a lower alkoxy group, a lower alkoxycarbonyl group, a di(lower alkyl) carbamoyl group and a group represented by —$R^{3p}$, and an amino group, a lower alkylamino group, a hydroxyl group, a carboxyl group, a carbamoyl group and a lower alkylcarbamoyl group, which may be protected; $R^2$ represents a hydrogen atom or a lower alkyl group; $R^{3p}$ represents a lower alkyl group which may have a substituent selected from the group consisting of a di(lower alkyl)carbamoyloxy group, a lower alkoxycarbonyl group, a di(lower alkyl) carbamoyl group, an aromatic heterocyclic group and a group represented by —$R^{5p}$, and an amino group, a lower alkylsulfonylamino group, an aminosulfonylamino group, a (lower alkylamino)sulfonylamino group, a (di-lower alkylamino)sulfonylamino group, a carbamoylamino group, a (lower alkylcarbamoyl)amino group, a (di-lower alkylcarbamoyl)amino group, a hydroxyl group, a carbamoyloxy group, a lower alkylcarbamoyloxy group, a carboxyl group, a carbamoyl group and a lower alkylcarbamoyl group, which may be protected; $R^4$ represents a lower alkyl group which may have a substituent selected from the group consisting of a cycloalkyl group having 3 to 10 carbon atoms and an aromatic carbo- or heterocyclic group; and $R^{5p}$ represents a lower alkylamino group which may be protected, a di(lower alkyl)amino group or a lower alkoxy group, which may have an aromatic carbo- or heterocyclic group, to prepare a compound represented by Formula (IV)

(IV)

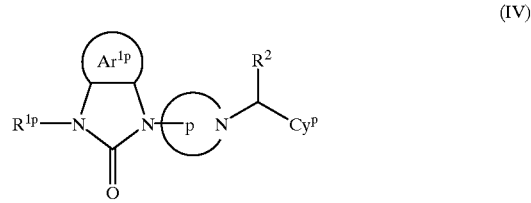

wherein

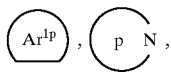

$Cy^p$, $R^{1p}$, and $^2$ are synonymous with those defined above, and the protective groups are optionally removed.

15. A pharmaceutical composition comprising a nociceptin receptor antagonistic effective amount of a compound of formula (I) as set forth in claim 1, a salt or ester thereof and at least one pharmaceutically acceptable adjuvant.

16. The composition of claim 15 comprising from about 1.0 to 60 percent by weight of the compound of formula (I), a salt or ester thereof.

17. A method for the treatment of pain, obesity, schizophrenia, Parkinsonism, chorea, depression, diabetes insipidus, polyuria or hypotension, the relief against tolerance to or dependency on a narcotic analgesic represented by morphine, the enhancement of an analgesic, or the amelioration of reduced cognitive brain function, comprising administering to a patient in need thereof, a nociceptin receptor antagonistic effective amount of a compound of formula (I) as set forth in claim 1, a salt or ester thereof.

* * * * *